United States Patent [19]

Goto et al.

[11] Patent Number: 5,527,800
[45] Date of Patent: Jun. 18, 1996

[54] TRICYCLIC CONDENSED HETEROCYCLIC COMPOUNDS, THEIR PRODUCTION AND USE

[75] Inventors: Giichi Goto, Toyono-gun; Yuji Ishihara, Itami; Keisuke Hirai, Habikino, all of Japan

[73] Assignee: Takeda Chemical Industries, Ltd., Osaka, Japan

[21] Appl. No.: 182,239

[22] Filed: Jan. 18, 1994

[30] Foreign Application Priority Data

| Jan. 18, 1993 | [JP] | Japan | 5-005535 |
| Jul. 13, 1993 | [JP] | Japan | 5-173287 |
| Sep. 27, 1993 | [JP] | Japan | 5-239672 |
| Nov. 30, 1993 | [JP] | Japan | 5-299827 |

[51] Int. Cl.$^6$ ............ A61K 31/495; A61K 31/50; A61K 31/55; A61K 31/44;C07D 401/00; C07D 451/00;c07D 487/00; C07D 319/06

[52] U.S. Cl. ............ 514/253; 514/217; 514/254; 514/294; 514/411; 544/361; 546/94; 546/95; 540/587; 548/428; 548/436; 549/375

[58] Field of Search ............ 546/94; 514/294, 514/253; 544/361

[56] References Cited

U.S. PATENT DOCUMENTS

| 3,716,539 | 2/1973 | Hopps et al. | 260/268 T R |
| 3,906,007 | 9/1975 | Albrecht et al. | 260/268 T R |
| 4,017,621 | 4/1977 | Tahashima et al. | 540/576 |
| 4,285,961 | 8/1981 | Prücher et al. | 548/265 |
| 4,559,371 | 12/1985 | Hüsler et al. | 204/158 R |
| 4,895,841 | 1/1990 | Sugimoto et al. | 514/212 |
| 5,106,856 | 4/1992 | Kosley, Jr. et al. | 514/321 |
| 5,202,321 | 4/1993 | Hutchinson et al. | 548/436 |
| 5,302,612 | 4/1994 | Flaugh et al. | 548/436 |
| 5,397,799 | 3/1995 | Kress et al. | 548/436 |

FOREIGN PATENT DOCUMENTS

| 0117233 | 8/1984 | European Pat. Off. . |
| 0296560 | 12/1988 | European Pat. Off. . |
| 0441517 | 8/1991 | European Pat. Off. . |
| 0487071 | 5/1992 | European Pat. Off. . |
| 0517221 | 12/1992 | European Pat. Off. . |
| 2106515 | 5/1972 | France . |

OTHER PUBLICATIONS

Chem. Abstracts, vol. 101, No. 3, Jul. 16, 1984, Abstract No. 23414f, Kumar et al., "Phenothiazine Derivatives as Anti Parkinsonian Agents," p. 596, col. 2.

Chem. Abstracts, vol. 53, No. 22, Nov. 25, 1959, Brunaud "Adrenolytic Activity of Various Phenothiazine Derivatives", col. 22521A.

Chem. Abstracts, vol. 116, No. 9, Mar. 2, 1992, Abstract No. 83548x, Goto et al., "Preparation of Piperidine Derivatives Containing Aminoaphthyl Groups as Brain Function Improvers", p. 806, col. 2.

Current Neurology, vol. 6, Edited by Stanley H. Appel, M.D. Chapter 11, pp. 289 and 315. (1987).

*Primary Examiner*—Cecilia Tsang
*Attorney, Agent, or Firm*—Foley & Lardner

[57] ABSTRACT

A novel compound of the formula:

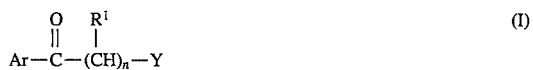

$$Ar-\overset{O}{\underset{\|}{C}}-(CH)_n-Y \qquad (I)$$

with $R^1$ on the CH, wherein Ar represents an optionally substituted tricyclic condensed benzene ring group which includes at least one heterocyclic ring as a component ring; n represents an integer from 2 to 10; $R^1$ represents H or an optionally substituted hydrocarbon group, which may be different from one another in the repetition of n; and Y represents an optionally substituted 4-piperidinyl, 1-piperazinyl or 4-benzyl-1-piperidinyl group, or a salt thereof, inhibiting excellent cholinesterase inhibitory activity and monoamine reuptake inhibitory activity, thus being useful as therapeutic and/or prophylactic medicaments of senile dementia.

6 Claims, No Drawings

TRICYCLIC CONDENSED HETEROCYCLIC COMPOUNDS, THEIR PRODUCTION AND USE

The present invention relates to a pharmaceutical, more specifically a cholinesterase inhibitor, particularly a therapeutic and/or prophylactic agent for senile dementia, Alzheimer's disease, etc., a novel tricyclic condensed benzene compound as an active ingredient thereof, a salt thereof, and a method of production thereof. Additionally, these compounds and compositions can be used in the diagnosis of such disease states.

To meet the demand from the aging society, there have been proposed various compounds exhibiting therapeutic and/or prophylactic action against senile dementia, including naturally occurring physostigmine, a cholinesterase inhibitor [e.g., International Journal of Clinical Pharmacology, Therapy and Toxicology, Vol. 29, No. 1, pp. 23–37 (1991)]. However, physostigmine has drawbacks such as short duration of action and strong toxicity.

On the other hand, synthetic tricyclic condensed ring compounds showing various modes of cholinesterase inhibition have been proposed (U.S. Pat. No. 4,895,841 corresponding to JP-A-2(1990)-169569, EP-A-0,441,517 corresponding to JP-A-4(1992)-234845, U.S. Pat. No. 5,106,856).

U.S. Pat. No. 4,895,841 discloses a cyclic amine derivative represented by the general formula:

$$J = B = T \overbrace{\underbrace{\phantom{XXXXXX}}_{(CH_2)_q}}^{} Q-K$$

wherein J represents (a) a substituted or unsubstituted ① phenyl group, ② pyridyl group, ③ pyrazyl group, ④ quinolyl group, ⑤ cyclohexyl group, ⑥ quinoxalyl group or ⑦ furyl group, (b) a monovalent or divalent group selected from the following groups optionally substituted with a phenyl group; ① indanyl, ② indanonyl, ③ indenyl, ④ indenonyl, ⑤ indandionyl, ⑥ tetralonyl, ⑦ benzosuberonyl, ⑧ indanolyl, ⑨ a group represented by the formula:

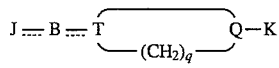

(c) a monovalent group derived from a cyclic amide compound, (d) a lower alkyl group, or (e) a group represented by the formula $R^1$—CH=CH— ($R^1$ represents a hydrogen atom or a lower alkoxycarbonyl group);

B represents a group represented by the formula —$(C(R^2)H)_n$—, a group represented by the formula —CO—$(C(R^2)H)_n$—, a group represented by the formula —$NR^2$—$(C(R^2)H)_n$— (in these formulas, $R^2$ represents a hydrogen atom, a lower alkyl group, an acyl group, a lower alkylsulfonyl group or an optionally substituted phenyl group or a benzyl group), a group represented by the formula —CO—$NR^4$—$(C(R^2)H)_n$— in which $R^4$ represents a hydrogen atom, a lower alkyl group or a phenyl group, a group represented by the formula —CH=CH—$(C(R^2)H)_n$—, a group represented by the formula —O—COO—$(C(R^2)H)_n$—, a group represented by the formula —O—CO—NH—$(C(R^2)H)_n$—, a group represented by the formula —NH—CO—$(C(R^2)H)_n$—, a group represented by the formula —$CH^2$—CO—NH—$(C(R^2)H)_n$—, a group represented by the formula —CO—NH—$(C(R^2)H)_n$—, a group represented by the formula —C(OH)H—$(C(R^2)H)_n$— (in the above formulas, n represents an integer from 0 to 10; $R^2$ represents a hydrogen atom or a methyl group in such way that the alkylene group represented by the formula —$(C(R^2)H)_n$— has no substituent or has one or more methyl groups), a group represented by the formula =(CH—CH=CH)$_b$— in which b represents an integer from 1 to 3, a group represented by the formula =CH—$(CH_2)_c$— in which c represents an integer from 0 to 9, a group represented by the formula =(CH—CH)$_d$= in which d represents an integer from 0 to 5, a group represented by the formula =CO—CH=CH—$CH_2$—, a group represented by the formula —CO—$CH_2$—C(OH)H—$CH_2$—, a group represented by the formula —C($CH_3$)H—CO—NH—$CH_2$—, a group represented by the formula —CH=CH—CO—NH—$(CH_2)_2$—, a group represented by the formula —NH—, a group represented by the formula —O—, a group represented by the formula —S—, a dialkylaminoalkylcarbonyl group or a lower alkoxycarbonyl group;

T represents an atom of nitrogen or carbon;

Q represents an atom of nitrogen or carbon or a group represented by the formula >N→O;

K represents a hydrogen atom, a substituted or unsubstituted phenyl group, an arylalkyl group optionally substituted with phenyl group, a cinnamyl group optionally substituted with phenyl group, a lower alkyl group, a pyridylmethyl group, a cycloalkylalkyl group, an adamantanemethyl group, a furylmethyl group, a cycloalkyl group, a lower alkoxycarbonyl group or an acyl group; q represents an integer from 1 to 3; ........ Represents a single bond or a double bond or a pharmaceutically acceptable salt thereof.

Specifically, the same publication describes the following tricyclic condensed ring compounds:

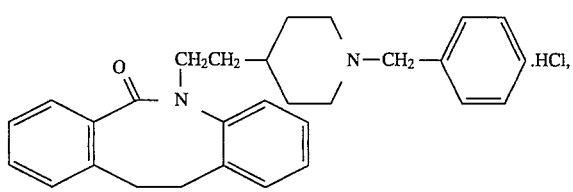

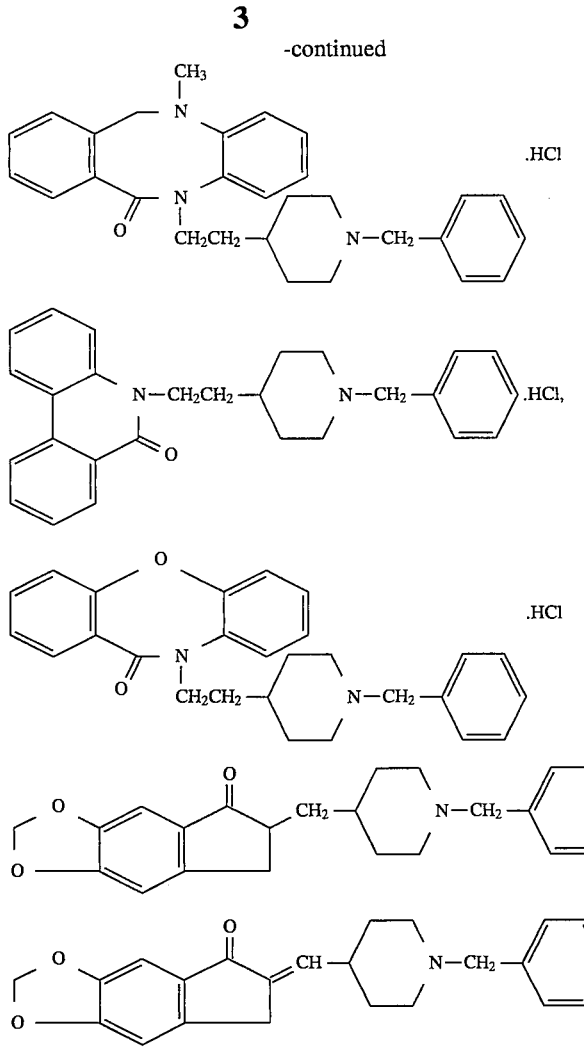

EP-A-0,441,517 describes a tricyclic amine compound represented by the formula:

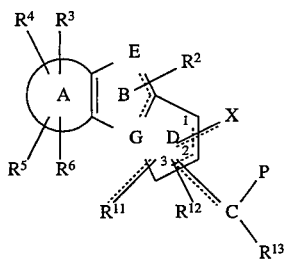

wherein P represents a group such as an N-substituted piperidino-1-yl-methyl group or an N-substituted piperazino-1-yl-methyl group; G represents carbon or nitrogen; E represents carbon, nitrogen, oxygen or sulfur; ring A is an aromatic ring such as of benzene, pyridine or thiophene, and a pharmaceutical composition containing it as an active ingredient.

The same publication describes that a compound of formula [I], having ring system ABD of 1H-pyrrolo[1,2-a]indol-1-one, cyclopento[d]indol-3-one, cyclopento[b](benzo[b]thieno)-1-one, 1H-pyrrolo[1,2-a](6-azaindol)-1-one or pyrrolo[1,2-a](thieno[2,3-b]pyrrol)-1-one, possesses cholinesterase inhibitory activity, and that a pharmaceutical composition containing it as an active ingredient enhances memory in patients with dementia or Alzheimer's disease.

Specifically, a compound represented by the following formula, for example, is described.

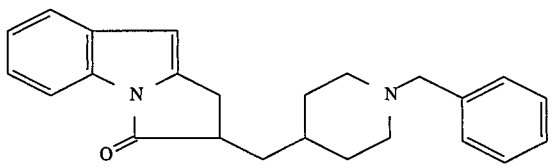

U.S. Pat. No. 5,106,856 describes a compound represented by the formula:

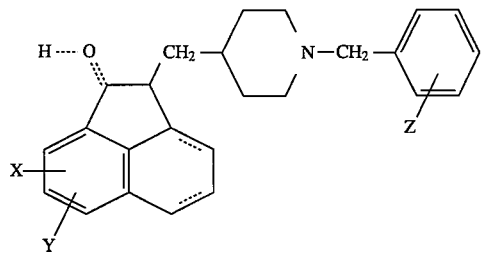

wherein X represents a hydrogen atom, a hydroxyl group, a nitro group, a lower alkyl group or a lower alkoxy group; Y represents a hydrogen atom or a lower alkoxy group; X and Y may bind together to form an OCH$_2$O group. Specifically, a compound represented by the following formula, for example, is described.

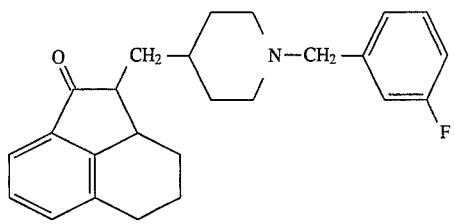

However, neither of U.S. Pat. No. 4,895,841, EP-A-0,441,517 or U.S. Pat. No. 5,106,856 disclose or suggest a tricyclic condensed ring compound wherein an N-substituted piperidino-1-yl-methyl or N-substituted piperidino-1-yl-ethyl group, as a substituent, is bound to a benzene ring thereof via a carbonyl group, though they disclose tricyclic condensed ring compounds wherein an N-substituted piperidino-1-yl-methyl or N-substituted piperidino-1-yl-ethyl group is bound directly to the heterocyclic ring or non-aromatic carbon ring thereof.

Also, U.S. Pat. No. 4,285,961 corresponding to JP-A-54(1979)-22333 discloses a compound represented by the formula:

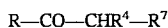
R—CO—CHR$^4$—R$^7$ wherein R represents a group such as a 2-dibenzothienyl group: R$^4$ represents an atom or group such as H; R$^7$ represents —(CH$_2$)$_n$—Z (n represents an integer from 1 to 3; Z represents —NR$^1$R$^2$ (R$^1$ and R$^2$ independently represent H or a C$_{1-4}$ alkyl group, and R$^1$ and R$^2$ may bind together to form a C$_{4-7}$ alkylene group or a 3-oxypentamethylene group), as an intermediate for the synthesis of a basic thioether compound possessing antifungal, antibacterial, antiinflammatory and other activities, but gives no disclosure concerning cholinesterase inhibitory action or therapeutic and/or prophylactic drug action against senile dementia.

EP-A-0,117,233 corresponding to JP-A-59(1984)-167546 describes a compound represented by the formula:

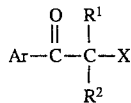

wherein Ar represents a structure such as the following:

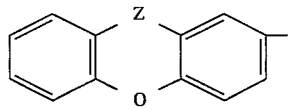

(Z represents a direct bond, a —CH$_2$— group, a —CH$_2$CH$_2$— group or an —O— group); X represents the amino group —N(R$^{11}$)(R$^{12}$) in which R$^{11}$ represents a hydrogen atom, an alkyl group having 1 to 12 carbon atoms, an alkyl group having 2 to 4 carbon atoms substituted with one or more groups selected from the group consisting of the OH, alkoxy groups having 1 to 4 carbon atoms, CN and —COO—C$_{1-4}$ alkyl groups, an alkenyl group having 3 to 5 carbon atoms, a cyclohexyl group, a phenylalkyl group having 7 to 9 carbon atoms, a phenyl group, or a phenyl group substituted with Cl, an alkyl group having 1 to 4 carbon atoms, OH, an alkoxy group having 1 to 4 carbon atoms or a —COO—C$_{1-4}$ alkyl group; R$^{11}$ and R$^1$ may bind together to form a —CH$_2$OCH$_2$— group;

R$^{12}$ represents one of the groups specified for R$^{11}$, or R$^{11}$ and R$^{12}$ may bind together to form an alkylene group having 5 to 7 carbon atoms or an alkylene group having 3 to 7 carbon atoms containing an —O— group, an —S— group or —N(R$^{14}$)—; R$^{12}$ and R$^2$ may bind together to form an alkylene group having 1 to 8 carbon atoms, a phenylalkylene group having 7 to 10 carbon atoms or an oxyalkylene group having 2 to 4 carbon atoms or an azaalkylene group;

R$^1$ and R$^2$ independently represent a group such as an alkyl group having 1 to 8 carbon atoms.

Specifically in this reference, a compound represented by the following formula, for example, is described as a photosetting coloring composition.

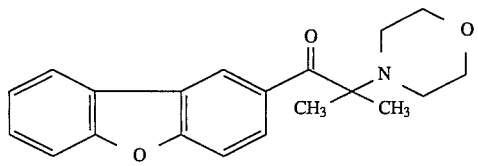

However, that publication gives no disclosure concerning cholinesterase inhibiting action or therapeutic and/or prophylactic drug action against senile dementia.

To cope with the increasing incidence of senile dementia, there is a need for the development of an excellent therapeutic and/or prophylactic agent for senile dementia which exhibits more potent action for a longer duration with lower toxicity, in comparison with conventional compounds known to possess therapeutic and/or prophylactic activity against senile dementia.

With this situation in mind, the present inventors investigated the bioactivities and pharmacologic actions of various heterocyclic compounds, including new ones, and stumbled upon the fact that a tricyclic condensed benzene derivative of unique chemical structure, which is characterized by an optionally substituted amino-alkyl or nitrogen-containing saturated heterocyclic-alkyl group being bound to the benzene of the tricyclic condensed benzene ring via a carbonyl group possesses unexpectedly excellent therapeutic and/or prophylactic activity against senile dementia based on its unique chemical structure.

The present inventors made further investigations based on this finding, and developed the present invention. Accordingly, the present invention relates to:

(1) a compound of the formula:

wherein Ar represents an optionally substituted tricyclic condensed benzene ring group which includes at least one heterocyclic ring as a component ring; n represents an integer from 2 to 10; R$^1$ represents a hydrogen atom or an optionally substituted hydrocarbon group, which may be different from one another in the repetition of n; and Y represents an optionally substituted 4-piperidinyl, 1-piperazinyl or 4-benzyl-1-piperidinyl group, or a salt thereof, (2) a method of producing the compound (I) or a salt thereof, which comprises reacting a compound of the formula:

Ar—H    (II)

wherein Ar has the same definition as above or a salt thereof, with a compound of the formula:

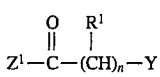 (III)

wherein $R^1$, Y and n have the same definitions as above; and $Z^1$ represents a leaving group or a salt thereof, (3) a method of producing a compound of the formula:

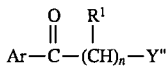 (VI)

wherein Y" represents an optionally substituted 1-piperazinyl or 4-benzyl-1-piperidinyl group, and the other symbols have the same definitions as above or a salt thereof, which comprises reacting a compound of the formula:

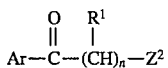 (IV)

or a salt thereof with a compound of the formula:

 (V)

wherein $Z^2$ and $Z^3$ are groups capable of reacting with each other to be removed; and the other symbols have the same definitions as above, or a salt thereof, (4) a cholinesterase inhibitor containing a compound of the formula:

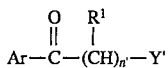 (I')

wherein n' represents an integer from 1 to 10; $R^1$ may be different from one another in the repetition of n'; Y' represents an optionally substituted amino group or an optionally substituted nitrogen-containing saturated heterocyclic group; and the other symbols have the same definitions as above, or a salt thereof, (5) a therapeutic and/or prophylactic agent for senile dementia which contains the compound (I') or a salt thereof and so on.

The compound (I) or salts thereof of the present invention are novel compounds having structural characteristics in that the substituent:

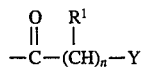

wherein the symbols are as defined above, is bound to a carbon atom of a benzene ring of a tricyclic condensed benzene ring including at least one heterocyclic ring as a component ring, and it exhibits excellent therapeutic and/or prophylactic actions for senile dementia based on these characteristics.

With respect to the above formulas, n represents an integer from 2 to 10; n' represents an integer from 1 to 10;

$R^1$ represents a hydrogen atom or an optionally substituted hydrocarbon group, which may be different from one another in the repetition of n or n'.

The "optionally substituted hydrocarbon group" for $R^1$ above is exemplified by chain or cyclic $C_{1-18}$ hydrocarbon groups and combinations thereof. Such chain hydrocarbon groups include linear or branched $C_{1-11}$ alkyl groups (e.g., methyl, ethyl, n-propyl, isopropyl, n-butyl, isobutyl, tert-butyl, n-pentyl, n-hexyl), linear or branched $C_{2-6}$ alkenyl groups (e.g., vinyl, allyl, 2-butenyl) and linear or branched $C_{2-6}$ alkynyl groups (e.g., propalgyl, 2-butynyl). Cyclic hydrocarbon groups include $C_{3-7}$ monocyclic cycloalkyl groups (e.g., cyclopropyl, cyclobutyl, cyclopentyl, cyclohexyl), $C_{8-14}$ bridged cyclic saturated hydrocarbon groups (e.g., bicyclo[3.2.1]octo-2-yl, bicyclo[3.3.1]non-2-yl, adamantan-1-yl) and $C_{6-14}$ aryl groups (e.g., phenyl group and naphthyl group).

Hydrocarbon groups consisting of a combination of a chain and a ring include $C_{7-8}$ aralkyl groups (e.g., phenyl-$CH_{1-2}$ alkyl groups or naphthyl-$C_{1-8}$ alkyl groups such as benzyl, phenylethyl, phenylpropyl, phenylbutyl, phenylpentyl, phenylhexyl and α-naphthylmethyl, and diphenyl-$C_{1-3}$ alkyl groups such as diphenylmethyl and diphenylethyl), $C_{6-14}$ aryl-$C_{2-12}$ alkenyl groups (e.g., phenyl-$C_{2-12}$ alkenyl groups such as styryl, cinnamyl, 4-phenyl-2-butenyl and 4-phenyl-3-butenyl), $C_{6-14}$ aryl-$C_{2-12}$ alkynyl groups (e.g., phenyl-$C_{2-12}$ alkynyl groups such as phenylethynyl, 3-phenyl-2-propynyl and 3-phenyl-1-propynyl), $C_{3-7}$ cycloalkyl-$C_{1-6}$ alkyl groups (e.g., cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl and cycloheptylhexyl).

The "hydrocarbon group" for $R^1$ is preferably a linear or branched $C_{1-11}$ alkyl group, more preferably a linear or branched $C_{1-7}$ alkyl group (e.g., methyl, ethyl, n-propyl, isopropyl, n-butyl, isobutyl, tert-butyl, n-pentyl, n-hexyl), or a $C_{7-18}$ aralkyl group, more preferably a $C_{7-10}$ aralkyl group (e.g., phenyl-$C_{1-4}$ alkyl such as benzyl, phenylethyl or phenylpropyl).

The "hydrocarbon group" for $R^1$ may have a substituent or substituents. This substituent may be chosen as appropriate from groups commonly used as substituents for the hydrocarbon group. Specifically, the above-described $C_{1-11}$ alkyl, $C_{2-6}$ alkenyl, $C_{2-6}$ alkynyl, $C_{3-7}$ monocyclic cycloalkyl or $C_{8-14}$ bridged cyclic saturated hydrocarbon group may have 1 to 5 substituents selected from the group comprising halogen atoms (e.g., fluorine, chlorine, bromine, iodine), nitro group, cyano group, hydroxyl group, $C_{1-4}$ alkoxy groups (e.g., methoxy, ethoxy, propyloxy, butyloxy, isopropyloxy), $C_{1-4}$ alkylthio groups (e.g., methylthio, ethylthio, propylthio), amino group, mono- or di-$C_{1-4}$ alkylamino groups (e.g., methylamino, ethylamino, propylamino, dimethylamino, diethylamino), 5- to 7-membered cyclic amino groups which may have 1 to 3 hetero atoms selected from atoms of nitrogen, oxygen and sulfur in addition to 1 nitrogen atom (e.g., pyrrolidino, piperidino, morpholino), $C_{1-4}$ alkyl-carbonylamino groups (e.g., acetylamino, propionylamino, butyrylamino), $C_{1-4}$ alkylsulfonylamino groups (e.g., methylsulfonylamino, ethylsulfonylamino), $C_{1-4}$ alkoxy-carbonyl groups (e.g., methoxycarbonyl, ethoxycarbonyl, propoxycarbonyl), carboxyl group, $C_{1-6}$ alkyl-carbonyl groups (e.g., methylcarbonyl, ethylcarbonyl, propylcarbonyl), carbamoyl group, mono- or di-$C_{1-4}$ alkyl-carbamoyl groups (e.g., methylcarbamoyl, ethylcarbamoyl) and $C_{1-6}$ alkylsulfonyl groups (e.g., methylsulfonyl, ethylsulfonyl, propylsulfonyl).

Substituents for the above-described $C_{6-14}$ aryl group, $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl may have include $C_{1-4}$ alkyl groups (e.g., methyl, ethyl, propyl, butyl), halogen atoms (e.g., fluorine, chlorine, bromine, iodine), nitro group, cyano group, hydroxyl group, $C_{1-4}$ alkoxy groups (e.g., methoxy, ethoxy, propyloxy, butyloxy, isopropyloxy), $C_{1-4}$ alkylthio groups (e.g., methylthio, ethylthio, propylthio, isopropylthio, butylthio), amino group, mono- or di-$C_{1-4}$ alkylamino groups (e.g., methylamino, ethylamino, propylamino, dimethylamino, diethylamino), 5- to 7-membered cyclic amino groups which may have 1 to 3 hetero atoms selected from atoms of nitrogen, oxygen and sulfur in addition to 1 nitrogen atom (e.g., pyrrolidino, piperidino, morpholino), $C_{1-4}$ alkyl-carbonylamino groups (e.g., acetylamino, propionylamino, butyrylamino), aminocarbonyloxy group, mono- or di-$C_{1-4}$ alkylamino-carbonyloxy groups (e.g., methylaminocarbonyloxy, ethylaminocarbonyloxy, dimethylaminocarbonyloxy, diethylaminocarbonyloxy), $C_{1-4}$ alkylsulfonylamino groups (e.g., methylsulfonylamino, ethylsulfonylamino, propylsulfonylamino), $C_{1-4}$ alkoxycarbonyl groups (e.g., methoxycarbonyl, ethoxycarbonyl, propoxycarbonyl, isobutoxycarbonyl), carboxyl group, $C_{1-6}$ alkyl-carbonyl groups (e.g., methylcarbonyl, ethylcarbonyl, butylcarbonyl), $C_{3-7}$ cycloalkyl-carbonyl groups (e.g., cyclohexylcarbonyl), carbamoyl group, mono- or di-$C_{1-4}$ alkyl-carbamoyl groups (e.g., methylcarbamoyl, ethylcarbamoyl, propylcarbamoyl, butylcarbamoyl, diethylcarbamoyl, dibutylcarbamoyl), $C_{1-6}$ alkylsulfonyl groups (e.g., methylsulfonyl, ethylsulfonyl, propylsulfonyl), $C_{3-7}$ cycloalkylsulfonyl groups (e.g., cyclopentylsulfonyl, cyclohexylsulfonyl), and phenyl, naphthyl, mono- or di-phenyl-$C_{1-3}$ alkyl (e.g., benzyl, diphenylmethyl), phenoxy, benzoyl, phenoxycarbonyl, benzylcarbonyl, phenyl-$C_{1-4}$ alkyl-carbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino and phenylsulfonylamino groups each of which may have 1 to 4 substituents (substituents for each phenyl group or naphthyl group include $C_{1-4}$ alkyl groups such as methyl, ethyl, propyl, butyl and isopropyl, $C_{1-4}$ alkoxy groups such as methoxy, ethoxy, n-propyloxy, isopropyloxy and n-butyloxy, halogen atoms such as atoms of chlorine, bromine and iodine, hydroxyl group, benzyloxy group, amino group, the above-mentioned mono- or di-$C_{1-4}$ alkylamino groups, nitro group, the above-mentioned $C_{1-6}$ alkylcarbonyl groups, and benzoyl group). The number of substituents for these $C_{6-14}$ aryl groups, $C_{7-18}$ aralkyl groups, $C_{6-14}$ aryl-$C_{2-12}$ alkenyl groups, $C_{6-14}$ aryl-$C_{2-12}$ alkynyl groups and $C_{3-7}$ cycloalkyl-$C_{1-6}$ alkyl groups is appropriately about 1 to 5.

With respect to the above formulas, Ar is a tricyclic condensed benzene ring group including at least one heterocyclic ring as a component ring and having a binding site at a carbon atom of a benzene ring thereof, and it may have a substituent or substituents. As stated above, the compound of the present invention is characterized by a unique chemical structure in which the benzene ring of the tricyclic condensed benzene ring including at least one heterocyclic ring is bound to a group represented by the formula:

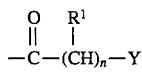

wherein the symbols are as defined above.

Since the compound of the present invention exhibits excellent cholinesterase inhibitory action based on this feature, the substituent for the tricyclic condensed benzene ring group for Ar is not subject to limitation.

The tricyclic condensed benzene ring group for Ar has a ring condensation pattern represented by one of the formulas:

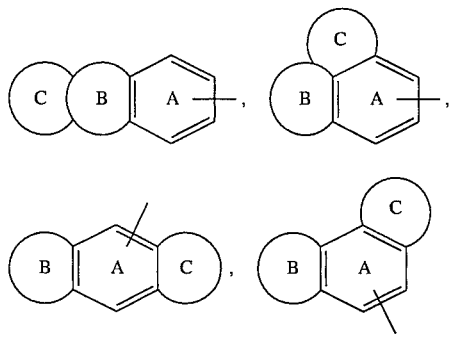

wherein ring A is an optionally substituted benzene ring; and one of rings B and C is an optionally substituted heterocyclic ring and the other is an optionally substituted 5- to 8-membered ring which may have a hetero atom or atoms as component atoms of the ring.

Benzene ring A may have an additional substituent or substituents in addition to one represented by the formula:

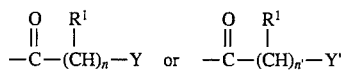

wherein the symbols are as defined above.

Such additional substituents include the same substituents as specified for the $C_{6-14}$ aryl, $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl group for $R^1$ above, the number thereof being preferably 1 to 3. Preferable substituents the benzene ring may have include halogen atoms such as fluorine and chlorine, halogeno-$C_{1-3}$ alkyl groups such as trifluoromethyl, $C_{1-3}$ alkyl groups such as methyl, $C_{1-3}$ alkoxy groups such as methoxy, and hydroxyl group, with greater preference given to halogen atoms such as fluorine.

The "optionally substituted heterocyclic ring" for ring B or C is exemplified by 4- to 14-membered rings, preferably 5- to 9-membered rings. As the hetero atom(s) of the heterocyclic ring, one to three hetero atoms are selected from nitrogen, oxygen, sulfur, etc. Specifically, such heterocyclic rings include pyridine, pyrazine, pyrimidine, imidazole, furan, thiophene, pyrrolidine, piperidine, hexamethyleneimine, tetrahydrofuran, piperazine, morpholine and thiomorpholine, with preference given to 5- to 9-membered non-aromatic heterocyclic rings having 1 hetero atom or two same or different hetero atoms (e.g., pyrrolidine, piperidine, hexamethyleneimine, tetrahydrofuran, piperazine, morpholine, thiomorpholine). For example, non-aromatic heterocyclic rings containing 1 hetero atom selected from nitrogen, oxygen and sulfur, and non-aromatic heterocyclic rings containing both 1 nitrogen atom and 1 hetero atom selected from nitrogen, oxygen and sulfur, in particular, are often used.

The "5- to 8-membered ring which may have hetero atoms" for ring B or C is a 5- to 8-membered heterocyclic ring or carbon ring which may have a substituent or substituents. This 5- to 8-membered carbon ring may be a benzene ring or a saturated or unsaturated ring, exemplified by benzene, cyclopentane, cyclopentene, cyclohexane, cyclohexene, cyclohexadiene, cycloheptane, cycloheptene and cycloheptadiene. When ring B or C has a hetero atoms (e.g., one to three hetero atoms selected from nitrogen, oxygen, sulfur, etc.) therein, i.e., when ring B or C is a heterocyclic ring, it may be aromatic or not. Such aromatic heterocyclic rings include pyridine, furan and thiophene. Preferable non-aromatic heterocyclic rings include the same non-aromatic heterocyclic rings as specified for ring B or C.

Accordingly, Ar is preferably a group having a binding site in a benzene ring of, e.g., a tricyclic condensed benzene ring represented by the formula:

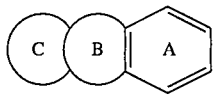

such as carbazole, 1,2,3,4,4a,9a-hexahydrocarbazol, 9,10-dihydroacridine, 1,2,3,4-tetrahydroacridine, 10,11-dihydro-5H-dibenz[b,f]azepine, 5,6,7,12-tetrahydrodibenz[b,g]azocine, 6,11-dihydro-5H-dibenz[b,e]azepine, 6,7-dihydro-5H-dibenz[c,e]azepine, 5,6,11,12-tetrahydrodibenz[b,f]azocine, dibenzofuran, 9H-xanthene, 10,11-dihydrobenz[b,f]oxepin, 6,11-dihydrobenz[b,e]oxepin, 6,7-dihydro-5H-dibenz[b,g] oxocin, dibenzothiophene, 9H-thioxanthene, 10,11-dihydrodibenzo[b,f]thiepin, 6,11-dihydrodibenzo[b,e]thiepin, 6,7-dihydro-5H-dibenzo[b,g]thiocin, 10H-phenothiazine, 10H-phenoxazine, 5,10-dihydrophenazine, 10,11-dibenzo[b,f][1,4]thiazepine, 10,11-dihydrodibenz[b,f][1,4]oxazepine, 2,3,5,6,11,11a-hexahydro-1H-pyrrolo[2,1-b][3]benzazepine, 10,11-dihydro-5H-dibenzo[b,e][1,4]diazepine, 5,11-dihydrodibenz[b,e][1,4]oxazepine, 5,11-dihydrodibenzo[b,f][1,4] thiazepine, 10,11-dihydro-5H-dibenzo[b,e][1,4]diazepine or 1,2,3,3a,8,8a-hexahydropyrrolo[2,3-b]indole, or a tricyclic condensed benzene ring represented by the formula:

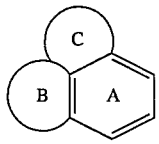

such as 1H,3H-naphth[1,8-cd][1,2]oxazine, naphth[1,8-de]-1,3-oxazine, naphth[1,8-de]-1,2-oxazine, 1,2,2a,3,4,5-hexahydrobenz[cd]indole, 2,3,3a,4,5,6-hexahydro-1H-benzo[de]quinoline, 4H-pyrrolo[3,2,1-ij]quinoline, 1,2,5,6-tetrahydro-4H-pyrrolo[3,2,1-ij]quinoline, 5,6-dihydro-4H-pyrrolo[3,2,1-ij]quinoline, 1H,5H-benzo[ij]quinolizine, 2,3,6,7-tetrahydro-1H,5H-benzo[ij]quinolizine, azepino[3,2,1-hi]indole, 1,2,4,5,6,7-hexahydroazepino[3,2,1-hi]indole, 1H-pyrido[3,2,1 -jk][1]benzazepine, 5,6,7,8-tetrahydro-1H-pyrido[3,2,1-jk][1]benzazepine, 1,2,5,6,7,8-hexahydro-3H-pyrido[3,2,1-jk][1]benzazepine, 2,3-dihydro-1H-benz[de] isoquinoline, 1,2,3,4,4a,5,6,7-octahydronaphth[1,8-bc]azepine or 2,3,5,6,7,8-hexahydro-1H-pyrido[3,2,1-jk][1] benzazepine, or a tricyclic condensed benzene ring represented by the formula:

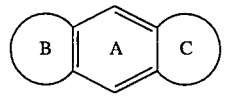

such as 1,2,3,5,6,7-hexahydrobenzo[1,2-b:4,5-b']dipyrrole, 1,2,3,5,6,7-hexahydrocyclopent[f]indole, 1,2,3,6,7,8-hexahydrocyclopent[e]indole or 2,3,4,7,8-hexahydro-1H-cyclopenta[f]quinoline, or a tricyclic condensed benzene ring represented by the formula:

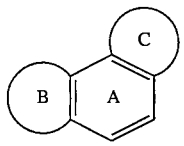

such as 1,2,3,6,7,8-hexahydrocyclopent[e]indole or 2,3,4,7, 8,9-hexahydro-1H-cyclopenta[f]quinoline. Groups having a binding site in a benzene ring of tricyclic condensed benzene ring represented by the following formulas:

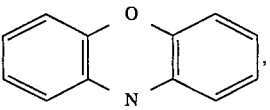

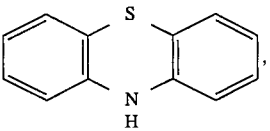

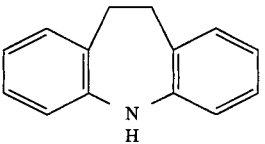

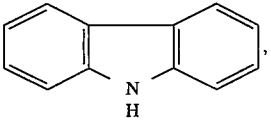

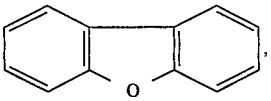

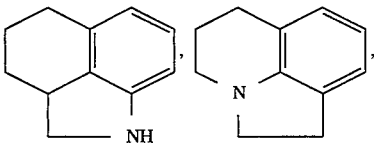

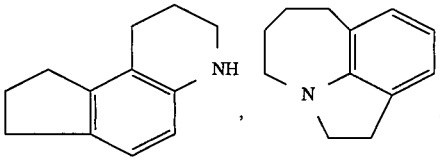

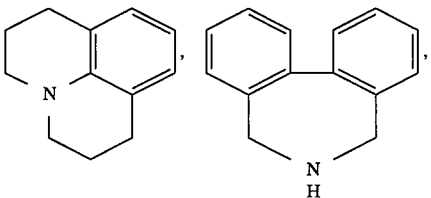

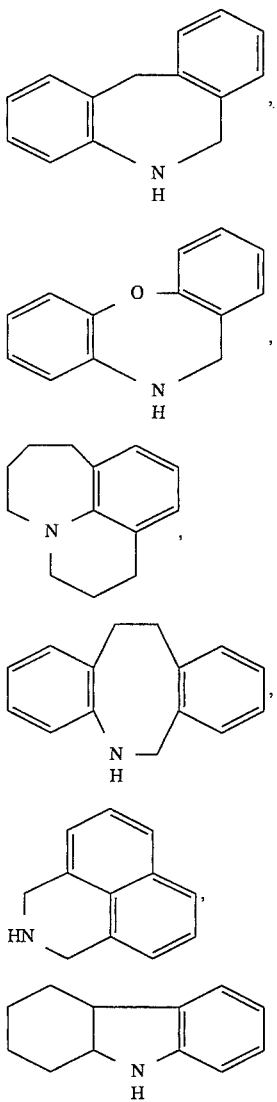

are often used.

Rings B and C may have a substituent or substituents on any carbon atom thereof. Such substituents include $C_{1-6}$ alkyl groups (e.g., methyl, ethyl), halogen atoms (e.g., fluorine, chlorine, bromine and iodine), nitro group, cyano group, oxo group, hydroxyl group, $C_{1-4}$ alkoxy groups (e.g., methoxy, ethoxy, propyloxy, butyloxy, isopropyloxy), $C_{1-4}$ alkylthio groups (e.g., methylthio, ethylthio, propylthio), amino group, mono- or di-$C_{1-4}$ alkylamino groups (e.g., methylamino, ethylamino, propylamino, dimethylamino, diethylamino), 5- to 7-membered cyclic amino groups which may have 1 to 3 hetero atoms selected from nitrogen, oxygen, sulfur etc. in addition to 1 nitrogen atom (e.g., pyrrolidino, piperidino, morpholino, thiomorpholino), $C_{1-4}$ alkyl-carbonylamino groups (e.g., acetylamino, propionylamino, butyrylamino), $C_{1-4}$ alkylsulfonylamino groups (e.g., methylsulfonylamino, ethylsulfonylamino), $C_{1-4}$ alkoxy-carbonyl groups (e.g., methoxycarbonyl, ethoxycarbonyl, propoxycarbonyl), carboxyl group, $C_{1-6}$ alkyl-carbonyl groups (e.g., methylcarbonyl, ethylcarbonyl, propylcarbonyl), carbamoyl group, mono- or di-$C_{1-4}$ alkyl-carbamoyl groups (e.g., methylcarbamoyl, ethylcarbamoyl) and $C_{1-6}$ alkylsulfonyl groups (e.g., methylsulfonyl, ethylsulfonyl, propylsulfonyl), the number of substituents being 1 to 5. As such substituents, oxo, $C_{1-6}$ alkyl such as methyl, etc. are often used.

As ring B or C, (1) a benzene ring which may be substituted with a $C_{1-6}$ alkyl (e.g., methyl) and/or a $C_{1-6}$ alkyl-carbonyl (e.g., acethyl), (2) a 5- to 7-membered saturated carbon ring such as cyclohexane, or (3) a 5- to 8-membered heterocyclic ring having 1 or 2 hetero atoms selected from oxygen, nitrogen and sulfur such as 5- to 8-membered nitrogen-containing saturated heterocyclic ring (e.g., pyrrolidine) are aften used.

When ring B or C has a nitrogen atom therein, it may have a substituent on that nitrogen atom. In other words, ring B or C may have therein $$>N-R^6$$

wherein $R^6$ represents a hydrogen atom, an optionally substituted hydrocarbon group or an optionally substituted acyl group.

The optionally substituted hydrocarbon group for $R^6$ is exemplified by the same optionally substituted hydrocarbon groups as specified for $R^1$, with preference, $C_{1-7}$ alkyl groups (e.g., methyl, ethyl, n-propyl) and $C_{7-10}$ aralkyl groups (e.g., phenylmethyl, phenylethyl), etc. These groups may be substituted with, for example, halogen atom (e.g., fluorine and chlorine, etc.), nitro, $C_{1-4}$ alkoxy group (e.g., methoxy, ethoxy), hydroxy group, etc. The unsubstituted benzyl group etc. are often used.

Y' represents an optionally substituted amino group or an optionally substituted nitrogen-containing saturated heterocyclic group.

The "optionally substituted amino group" for Y' is exemplified by a group represented by the formula:

 (VII)

wherein $R^{2'}$ and $R^{3'}$ represent, respectively, a hydrogen atom, an optionally substituted hydrocarbon group or an optionally substituted acyl group.

The optionally substituted hydrocarbon group for $R^{2'}$ or $R^{3'}$ is exemplified by the same optionally substituted hydrocarbon groups as specified for $R^1$ above.

Example preferable optionally substituted hydrocarbon groups for $R^{2'}$ or $R^{3'}$ include linear or branched $C_{1-11}$ alkyl groups (e.g., methyl, ethyl, n-propyl, isopropyl, n-butyl, isobutyl, tert-butyl, n-pentyl, n-hexyl) and $C_{7-18}$ aralkyl groups (e.g., phenyl-$C_{1-12}$ alkyl groups such as phenylmethyl, phenylethyl, phenylpropyl and phenylhexyl, and naphthyl-$C_{1-8}$ alkyl groups such as $\alpha$-naphthylmethyl), more preferably linear or branched $C_{1-7}$ alkyl groups (e.g., methyl, ethyl, propyl) and $C_{7-10}$ aralkyl groups (e.g., phenylmethyl, phenylethyl, phenylpropyl). These groups may have 1 to 3 substituents such as halogen atom (e.g., fluorine and chlorine), $C_{1-4}$ alkoxy (e.g., methoxy, ethoxy), hydroxy.

The acyl group of the "optionally substituted acyl group" for $R^6$, $R^{2'}$ or $R^{3'}$ is exemplified by carboxylic acid acyl groups (e.g., formyl, $C_{2-8}$ alkylcarbonyl or phenylcarbonyl groups such as acetyl, propionyl, butyryl and benzoyl), sulfonic acid acyl groups (e.g., $C_{1-7}$ alkylsulfonyl or phenylsulfonyl groups such as methanesulfonyl, ethanesulfonyl, propanesulfonyl, benzenesulfonyl and p-toluenesulfonyl), phosphonic acid acyl groups (e.g., $C_{1-7}$ alkylphosphonyl or phenylphosphonyl groups such as methanephosphonyl, ethanephosphonyl, propanephosphonyl, benzenephosphonyl and p-toluenephosphonyl), substituted oxycarbonyl groups (e.g., $C_{2-8}$ alkyloxycarbonyl or $C_{7-8}$ aralkyloxycarbonyl groups such as methyloxycarbonyl, tert-butyloxycarbonyl and benzyloxycarbonyl), with preference given to $C_{2-8}$ alkyloxycarbonyl groups.

Substituents for these acyl groups may have include halogen atoms (e.g., fluorine, chlorine, bromine and iodine), nitro group, hydroxyl group, amino group, mono- or di-$C_{1-6}$ alkylamino groups (e.g., methylamino, ethylamino, dimethylamino, diethylamino) and $C_{1-4}$ alkoxy groups (e.g., methoxy, ethoxy, propoxy), the number of substituents being 1 to 3, preferably 1 to 2.

Preferable groups for $R^{2'}$ and $R^{3'}$ include linear or branched $C_{1-7}$ alkyl groups (e.g., methyl, ethyl, n-propyl, isopropyl, n-butyl, isobutyl, tert-butyl, n-pentyl, n-hexyl) and $C_{7-10}$ aralkyl group (e.g., benzyl, phenylethyl, phenylpropyl), with preference given to $C_{1-3}$ alkyl groups such as methyl and ethyl and $C_{7-10}$ aralkyl groups such as phenylmethyl.

The "nitrogen-containing saturated heterocyclic group" for Y' is exemplified by 5- to 9-membered nitrogen-containing saturated heterocyclic groups which may have 1 to 3 hetero atoms selected from nitrogen, oxygen, sulfur, etc. in addition to carbon atoms and 1 nitrogen atom(s). These nitrogen-containing saturated heterocyclic groups may have a bond at a ring component nitrogen atom thereof or at a ring component carbon atom thereof. Groups having a bond at a ring component nitrogen atom include a group represented by the formula:

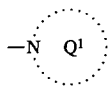

wherein ring $Q^1$ is a 5- to 9-membered nitrogen-containing saturated heterocyclic group which may have 1 or 2 hetero atoms selected from nitrogen, oxygen, sulfur, etc. in addition to carbon atoms and 1 nitrogen atom. More specifically, the following, for example, are often used.

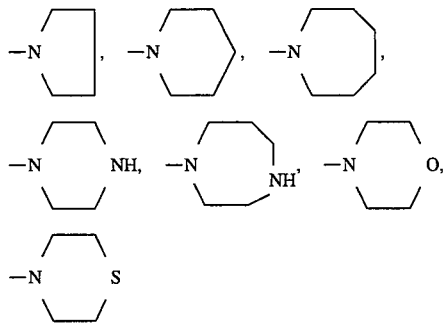

Groups having a bond at a ring component carbon atom include a group represented by the formula:

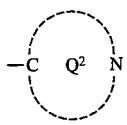

wherein ring $Q^2$ is a 5- to 9-membered nitrogen-containing saturated heterocyclic group which may have 1 or 2 hetero atoms selected from nitrogen, oxygen, sulfur, etc. in addition to carbon atoms and 1 nitrogen atom. More specifically, the following, for example, are often used.

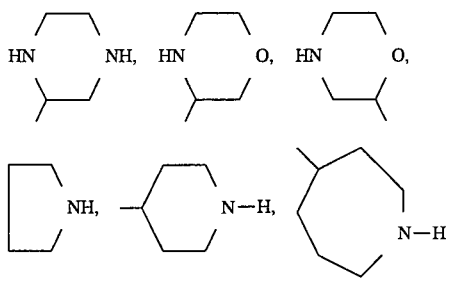

Y represents an "optionally substituted 4-piperidinyl, 1-piperazinyl or 4-benzyl-1-piperidinyl group" such as

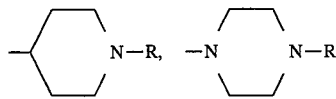

or

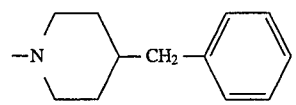

(R represents H or a substituent).

As examples of the substituents which the above-described "nitrogen-containing saturated heterocyclic group," "4-piperidinyl group" or "1-piperazinyl group" may have and the substituent of R, there may be described those of optionally substituted hydrocarbon groups as specified for $R^1$ above, optionally substituted acyl groups as specified for $R^{2'}$ or $R^{3'}$ above, halogen atoms (e.g., fluorine, chlorine, bromine and iodine), nitro group, cyano group, oxo group, hydroxyl group, $C_{1-4}$ alkoxy groups (e.g., methoxy, ethoxy, propyloxy, butyloxy, isopropyloxy), $C_{1-4}$ alkylthio groups (e.g., methylthio, ethylthio, propylthio, isopropylthio), amino group, mono- or di-$C_{1-4}$ alkylamino groups (e.g., methylamino, ethylamino, propylamino, dimethylamino, diethylamino), 5- to 7-membered cyclic amino groups which may have 1 to 3 hetero atoms selected from atoms of nitrogen, oxygen, sulfur etc. in addition to carbon atoms and 1 nitrogen atom (e.g., pyrrolidino, piperidino, morpholino, thiomorpholino), $C_{1-4}$ alkyl-carbonylamino groups (e.g., acetylamino, propionylamino, butyrylamino), $C_{1-4}$ alkylsulfonylamino groups (e.g., methylsulfonylamino, ethylsulfonylamino), $C_{1-4}$ alkoxy-carbonyl groups (e.g., methoxycarbonyl, ethoxycarbonyl, propoxycarbonyl), phenyl-$C_{1-4}$ alkyl-oxycarbonyl groups (e.g., benzyloxycarbonyl), carboxyl group, $C_{1-6}$ alkyl-carbonyl groups (e.g., methylcarbonyl, ethylcarbonyl, propylcarbonyl), benzoyl groups which may have a substituent (here, the substituent is exemplified by $C_{1-4}$ alkyl groups such as methyl and ethyl, halogens such as fluorine, chlorine and bromine, $C_{1-4}$ alkoxy groups such as methoxy and ethoxy, mono- or di-$C_{1-4}$ alkylamino group such as methylamino and dimethylamino, 5- to 7-membered cyclic amino groups such as piperidino and morpholino, nitro and hydroxy, the number of substituents being 1 to 3 such as 4-fluorobenzoyl and 3,4-dimethoxybenzoyl), carbamoyl group, mono- or di-$C_{1-4}$ alkyl-carbamoyl groups (e.g., methylcarbamoyl, ethylcarbamoyl) and $C_{1-6}$ alkylsulfonyl groups (e.g., methylsulfonyl, ethylsulfonyl, propylsulfonyl), the number of substituents being 1 to 5. Of these substituents, the same optionally substituted hydrocarbon groups as specified for $R^1$ above are preferred. For example, chain or branched $C_{1-11}$ alkyl groups, preferably linear or branched $C_{1-7}$ alkyl groups (e.g., methyl, ethyl, n-propyl, isopropyl, n-butyl, tert-butyl, n-pentyl, n-hexyl), which may be substituted with halogen atoms (e.g., fluorine, chlorine, bromine and iodine), nitro group, $C_{1-4}$ alkoxy groups (e.g., methoxy, ethoxy), hydroxyl group etc., $C_{7-18}$ aralkyl groups (e.g., phenyl-$C_{1-12}$ alkyl groups such as phenylmethyl, phenylethyl, phenylpropyl and phenylhexyl and naphthyl-$C_{1-8}$ alkyl groups such as α-naphthylmethyl), preferably $C_{7-10}$ aralkyl groups (e.g., phenylmethyl, phenylethyl, phenylpropyl), and diphenyl-$C_{1-3}$ alkyl groups (e.g., diphenylmethyl) are often used. The position of substitution may be on a carbon atom and/or nitrogen atom of the nitrogen-containing saturated heterocyclic ring.

As the substituents which the above-described "4-benzyl-1-piperidinyl group" for Y may have, use is made of, for example, those similar to the substituents which the above-described $C_{6-14}$ aryl, $C_{7-18}$ aralkyl, $C_{6-14}$ aryl-$C_{2-12}$ alkenyl, $C_{6-14}$ aryl-$C_{2-12}$ alkynyl, $C_{3-7}$ cycloalkyl-$C_{1-6}$ alkyl may have.

Compound (I') or a salt thereof wherein Y' represents an optionally substituted 4-piperidinyl, 1-piperazinyl or 4-benzyl-1-piperidinyl group and n' represents an integer from 2 to 10, is a novel compound, exhibiting more potent cholinesterase inhibitory action.

With respect to the above formulas, $R^1$ is preferably a hydrogen atom, for example.

Benzene ring A preferably has no substituent.

Preferable ring structures for Ar include the following:

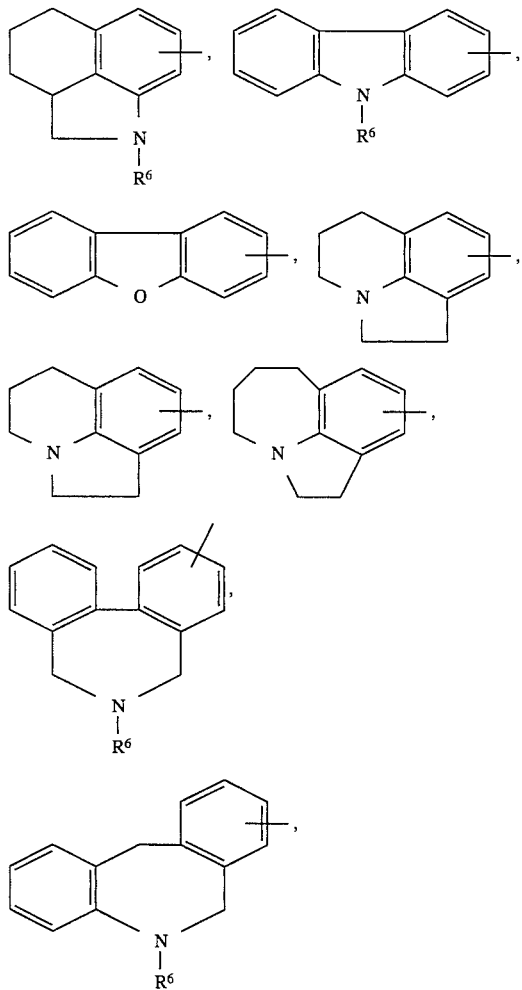

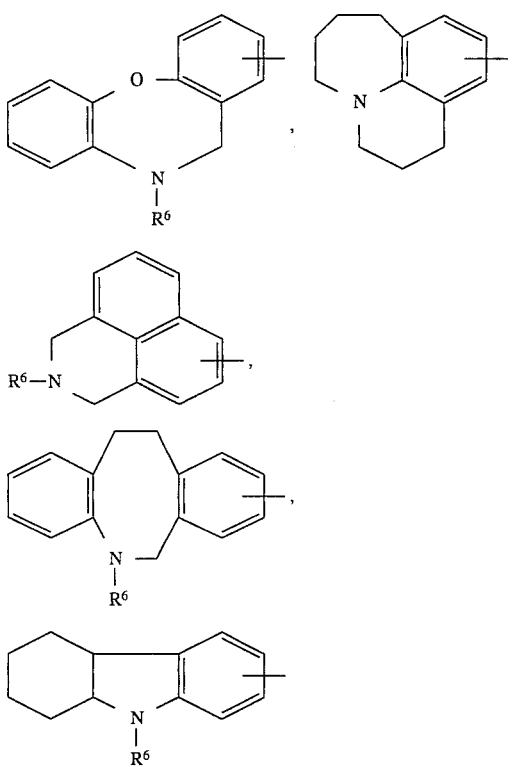

wherein $R^6$ has the same definition as above.

$R^6$ is (1) hydrogen, (2) a $C_{1-6}$ alkyl (e.g., methyl, ethyl), phenyl-$C_{1-4}$ alkyl (e.g., benzyl), $C_{1-6}$ alkyl-carbonyl (e.g., acethyl), benzoyl, $C_{1-6}$ alkoxy-carbonyl (e.g., methoxycarbonyl, ethoxycarbonyl) or mono- or di-$C_{1-4}$ alkyl-carbamoyl group (e.g., methylcarbamoyl) which may be substituted with 1 or 2 substituents such as halogen (e.g., fluorine, chlorine), nitro, $C_{1-4}$ alkoxy (e.g., methoxy, ethoxy) and hydroxy, (3) formyl or (4) carbamoyl, more preferably a hydrogen atom, a formyl group or methyl, etc.

Y' is preferably group (VII) (particularly group (VII) wherein one of $R^{2'}$ and $R^{3'}$ is a linear or branched $C_{1-7}$ alkyl group such as methyl, ethyl, n-propyl, isopropyl, n-butyl, isobutyl, tert-butyl, n-pentyl or n-hexyl and the other is a $C_{7-10}$ aralkyl group such as phenylmethyl, phenylethyl or phenylpropyl), or pyrrolidine, piperidine, piperazine, morpholine, 1,2,3,4-tetrahydroquinoline, 1,2,3,4-tetrahydroisoquinoline, 2,3,4,5-tetrahydro-1H-1-benzazepine, 2,3,4,5-tetrahydro-1H-2-benzazepine or 2,3,4,5-tetrahydro-1H-3-benzazepine substituted with an optionally substituted benzyl group, etc. Preference is given to groups such as pyrrolidine, piperidine, piperazine and morpholine substituted with a substituted or unsubstituted benzyl group. The substituents of the benzyl group are preferably halogen such as fluorine, chlorine, $C_{1-4}$ alkyl such as methyl, ethyl, $C_{1-4}$ alkoxy such as methoxy, hydroxy, nitro, amino, etc.

Y is preferably a 4-piperidinyl, 1-piperazinyl or substituted or unsubstituted 4-benzyl-piperidinyl group substituted with a substituted or unsubstituted benzyl group. The substituents of the benzyl group are preferably halogen such as fluorine, chlorine, $C_{1-4}$ alkyl such as methyl, ethyl, $C_{1-4}$ alkoxy such as methoxy, hydroxy, nitro, amino, etc.

n and n' are preferably integers from 2 to 6.

More specifically, the following compounds (and salts thereof) categorized under compounds (I) or (I') are preferred.

TABLE 1

$$\text{Ar} - \overset{\text{O}}{\underset{\|}{\text{C}}} - (\text{CH}_2)_n - \text{Y}$$

| No. | Ar | n | Y |
|---|---|---|---|
| 1 | tetrahydronaphthyl-CH2-NH | 2 | piperidine-NH |
| 2 | tetrahydronaphthyl-CH2-NH | 2 | piperidine-N-CH3 |
| 3 | tetrahydronaphthyl-CH2-NH | 2 | piperidine-N-CH2Ph |
| 4 | tetrahydronaphthyl-CH2-NH | 1 | piperidine-N-CH2Ph |
| 5 | tetrahydronaphthyl-CH2-NH | 3 | piperidine-N-CH2Ph |
| 6 | tetrahydronaphthyl-CH2-NH | 4 | piperidine-N-CH2Ph |
| 7 | tetrahydronaphthyl-CH2-NHCO | 2 | piperidine-N-Ac |
| 8 | tetrahydronaphthyl-CH2-NH | 2 | piperidine-N-CH2Ph |

TABLE 1-continued $$Ar-\overset{O}{\underset{\|}{C}}-(CH_2)_n-Y$$

| No. | Ar | n | Y |
|---|---|---|---|
| 9 | tetrahydronaphthalene with CH2-NAc substituent | 2 | piperidine N-CH2Ph |
| 10 | tetrahydronaphthalene with CH2-NCH2Ph substituent | 2 | piperidine N-CH2Ph |
| 11 | tetrahydronaphthalene with CH2-NCH3 substituent | 2 | piperidine N-CH2Ph |
| 12 | tetrahydronaphthalene with CH2-NH substituent | 2 | piperidine N-CH2-C6H4-F (meta) |
| 13 | tetrahydronaphthalene with CH2-NH substituent | 2 | piperidine N-CH2-C6H4-OCH3 (para) |

TABLE 2

| No. | Ar | n | Y |
|---|---|---|---|
| 14 | tetrahydronaphthalene with CH2-NH substituent | 2 | piperidine N-CH2-C6H4-OCH3 (meta) |
| 15 | tetrahydronaphthalene with CH2-NH substituent | 2 | piperidine N-CH2-C6H4-OH (meta) |

TABLE 2-continued

| No. | Ar | n | Y |
|---|---|---|---|
| 16 | tetrahydronaphthalene-CH₂-NCH₂-C₆H₄-OCH₃ | 2 | 4-(N-CH₂Ph)piperidinyl |
| 17 | tetrahydronaphthalene-CH₂-NCOPh | 2 | 4-(N-CH₂Ph)piperidinyl |
| 18 | tetrahydronaphthalene-CH₂-NCO₂Et | 2 | 4-(N-CH₂Ph)piperidinyl |
| 19 | tetrahydronaphthalene-CH₂-NHCO | 2 | 4-(N-CH₂Ph)piperazinyl |
| 20 | tetrahydronaphthalene-CH₂-NH | 2 | 4-(N-CH₂Ph)piperazinyl |
| 21 | tetrahydronaphthalene-CH₂-NAc | 2 | 4-(N-CH₂Ph)piperazinyl |
| 22 | tetrahydronaphthalene-CH₂-NCO₂Et | 2 | 4-(N-CH₂Ph)piperazinyl |
| 23 | tetrahydronaphthalene-CH₂-NH | 1 | 4-(N-CH₂Ph)piperazinyl |
| 24 | tetrahydronaphthalene-CH₂-NH | 3 | 4-(N-CH₂Ph)piperazinyl |

TABLE 2-continued
| No. | Ar | n | Y |
|---|---|---|---|
| 25 | 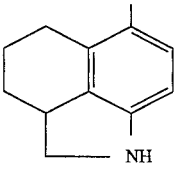 | 4 | 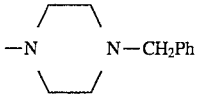 |
| 26 | 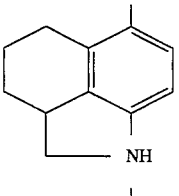 | 2 | 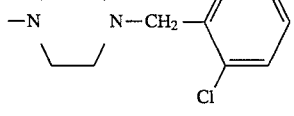 |
| 27 | 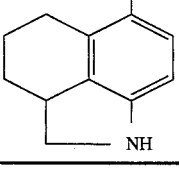 | 2 | 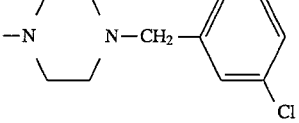 |
TABLE 3
| No. | Ar | n | Y |
|---|---|---|---|
| 28 | 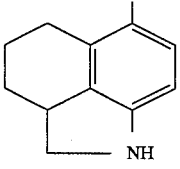 | 2 | 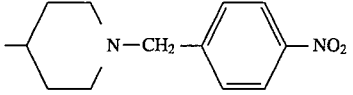 |
| 29 | 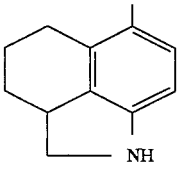 | 2 | 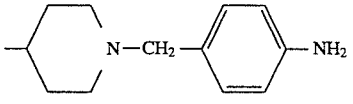 |
| 30 | 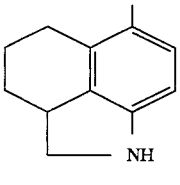 | 2 | 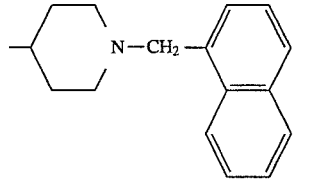 |
| 31 | 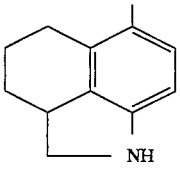 | 2 | 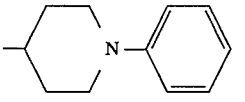 |
| 32 | 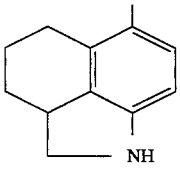 | 2 | 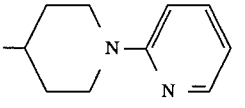 |

TABLE 3-continued

| No. | Ar | n | Y |
|---|---|---|---|
| 33 | tetrahydronaphthalene-CH₂-NH- | 2 | piperidinyl-pyrimidine (4-pyrimidin-2-yl-piperidin-1-yl) |
| 34 | tetrahydronaphthalene-CH₂-NH- | 2 | -N(piperazine)N-CHPh₂ |
| 35 | tetrahydronaphthalene-CH₂-NH- | 2 | -N(piperidine) |
| 36 | tetrahydronaphthalene-CH₂-NH- | 2 | -N(piperidin-4-yl)-C(=O)-C₆H₄-4-F |
| 37 | tetrahydronaphthalene-CH₂-NH- | 2 | -N(piperidin-4-yl)(OH)(4-Cl-C₆H₄) |
| 38 | tetrahydronaphthalene-CH₂-NH- | 2 | -N(morpholine) |
| 39 | tetrahydronaphthalene-CH₂-NH- | 2 | -N(thiomorpholine/thiazinane) S |
| 40 | tetrahydronaphthalene-CH₂-NH- | 2 | -N(CH₃)₂ |
| 41 | tetrahydronaphthalene-CH₂-NH- | 2 | -N(C₂H₅)₂ |

TABLE 3-continued

| No. | Ar | n | Y |
|---|---|---|---|
| 42 | tetrahydronaphthalene-CH₂-NH | 5 | −N(C₂H₅)(CH₂Ph) |
| 43 | tetrahydronaphthalene-CH₂-NHCO | 5 | −N(C₂H₅)(CH₂Ph) |

TABLE 4

| No. | Ar | n | Y |
|---|---|---|---|
| 44 | tetrahydronaphthalene-CH₂-NH | 6 | −N(C₂H₅)(CH₂Ph) |
| 45 | tetrahydronaphthalene-CH₂-NHCO | 6 | −N(C₂H₅)(CH₂Ph) |
| 46 | tetrahydronaphthalene-CH₂-NH | 2 | −N(piperazine)N−C₆H₄−CO₂H |
| 47 | tetrahydronaphthalene-CH₂-NH | 3 | −N(piperazine)N−(2-pyridyl) |
| 48 | tetrahydronaphthalene-CH₂-NH | 3 | −N(piperazine)N−(2-pyrimidinyl) |
| 49 | tetrahydronaphthalene-CH₂-NH | 3 | −N(piperazine)N−CHPh₂ |

TABLE 4-continued

| No. | Ar | n | Y |
|---|---|---|---|
| 50 | tetrahydronaphthalene-CH₂NH- | 3 | -N(piperidine) |
| 51 | tetrahydronaphthalene-CH₂NH- | 3 | -N(piperidine)-C(=O)-C₆H₄-4-F |
| 52 | tetrahydronaphthalene-CH₂NH- | 3 | -N(4-OH, 4-(4-Cl-C₆H₄)-piperidine) |
| 53 | tetrahydronaphthalene-CH₂NHCO- | 3 | -N(morpholine) |
| 54 | tetrahydronaphthalene-CH₂NCH₂Ph- | 3 | -N(thiazolidine) |
| 55 | tetrahydronaphthalene-CH₂NCOPh- | 3 | -N(CH₃)₂ |
| 56 | tetrahydronaphthalene-CH₂NH- | 3 | -N(C₂H₅)₂ |
| 57 | tetrahydronaphthalene-CH₂NCH₃- | 5 | -N(C₂H₅)(CH₂Ph) |
| 58 | tetrahydronaphthalene-CH₂NAc- | 5 | -N(C₂H₅)(CH₂Ph) |

TABLE 4-continued

| No. | Ar | n | Y |
|---|---|---|---|
| 59 | (tetrahydronaphthalene with CH₂—NAc substituent) | 6 | —N(C₂H₅)(CH₂Ph) |

TABLE 5

| No. | Ar | n | Y |
|---|---|---|---|
| 60 | (tetrahydronaphthalene with CH₂—NH substituent) | 6 | —N(C₂H₅)(CH₂-2-methoxyphenyl) |
| 61 | (tetrahydronaphthalene with CH₂—NH substituent) | 2 | —N(pyrrolidinyl) |
| 62 | (tetrahydronaphthalene with CH₂—NH substituent) | 2 | —N(4-oxopiperidinyl) |
| 63 | (tetrahydronaphthalene with CH₂—NH substituent) | 2 | —N(1,4-dioxa-8-azaspiro[4.5]decyl) |
| 64 | (tetrahydronaphthalene with CH₂—NH substituent) | 2 | —NH—(thiazol-2-yl) |
| 65 | (tetrahydronaphthalene with CH₂—NH substituent) | 2 | —N(hexamethyleneimino) |
| 66 | (tetrahydronaphthalene with CH₂—NH substituent) | 2 | —N(2,3,4,5-tetrahydro-1H-2-benzazepin-2-yl) |

TABLE 5-continued

| No. | Ar | n | Y |
|---|---|---|---|
| 67 | tetrahydronaphthyl-CH₂—NH | 2 | —N(1,2,3,4-tetrahydroisoquinolin-2-yl) |
| 68 | tetrahydronaphthyl-CH₂—NAc | 2 | —N(piperazinyl)NAc |
| 69 | tetrahydronaphthyl-CH₂—NHCO | 2 | —N(piperazinyl)N—CHO |
| 70 | tetrahydronaphthyl-CH₂—NCH₂Ph | 2 | —N(piperazinyl)N—CH₂CH₂OH |
| 71 | tetrahydronaphthyl-CH₂—NCH₂CH₂Ph | 1 | —N(piperazinyl)N—CHPh₂ |
| 72 | tetrahydronaphthyl-CH₂—NCONHCH₃ | 4 | —N(piperazinyl)N—CHPh₂ |
| 73 | tetrahydronaphthyl-CH₂—NCOPh | 4 | —N(piperazinyl)N—(pyrimidin-2-yl) |
| 74 | tetrahydronaphthyl-CH₂—NH | 5 | —N(piperazinyl)N—CHPh₂ |

TABLE 5-continued
| No. | Ar | n | Y |
|---|---|---|---|
| 75 | 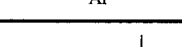 | 5 | 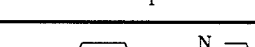 |
TABLE 6
| No. | Ar | n | Y |
|---|---|---|---|
| 76 | 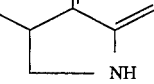 | 1 | 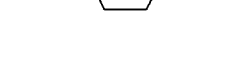 |
| 77 | 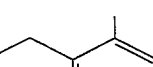 | 1 |  |
| 78 | 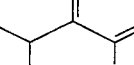 | 2 | 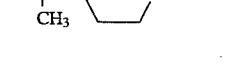 |
| 79 |  | 2 |  |
| 80 | 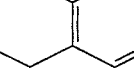 | 2 | 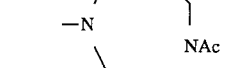 |
| 81 | 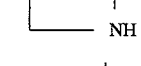 | 2 | 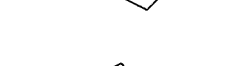 |
| 82 |  | 2 | 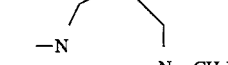 |

TABLE 6-continued

| No. | Ar | n | Y |
|---|---|---|---|
| 83 | tetrahydronaphthyl-CH₂-NHCO | 2 | 4-methylpiperidine-N-CH₂-C₆H₄-COCH₃ (para) |
| 84 | tetrahydronaphthyl-CH₂-NHCO | 2 | 4-methylpiperidine-N-CH₂-C₆H₄-OAc (meta) |
| 85 | tetrahydronaphthyl-CH₂-NAc | 2 | 4-methylpiperidine-N-CH₂-C₆H₄-Br (para) |
| 86 | tetrahydronaphthyl-CH₂-NAc | 2 | piperazine-N-CH₂-C₆H₄-OH (para) |
| 87 | tetrahydronaphthyl-CH₂-NAc | 2 | piperazine-N-CH(CH₃)-C₆H₄-OH (para) |
| 88 | tetrahydronaphthyl-CH₂-NAc | 2 | piperazine-N-CH₂-C₆H₄-OCH₃ (meta) |
| 89 | tetrahydronaphthyl-CH₂-NCH₂Ph | 2 | piperazine-N-CH₂-C₆H₃(OCH₃)₂ (3,4-dimethoxy) |
| 90 | tetrahydronaphthyl-CH₂-NCH₂Ph | 2 | piperazine-N-CH₂-C₆H₄-OCH₃ (meta) |

TABLE 7

| No. | Ar | n | Y |
|---|---|---|---|
| 91 | dibenzofuran | 2 | piperidine-N—CH₂Ph |
| 92 | Ac-dibenzofuran | 2 | piperidine-N—CH₂Ph |
| 93 | dibenzofuran | 2 | piperazine —N⟩⟨N—CH₂Ph |
| 94 | Ac-dibenzofuran | 2 | piperazine —N⟩⟨N—CH₂Ph |
| 95 | carbazole (N-H) | 2 | piperidine-N—CH₂Ph |
| 96 | carbazole (N-CHO) | 2 | piperidine-N—CH₂Ph |
| 97 | carbazole (N-Ac) | 2 | piperidine-N—CH₂Ph |
| 98 | carbazole (N-H) | 2 | piperazine —N⟩⟨N—CH₂Ph |
| 99 | carbazole (N-Ac) | 2 | piperazine —N⟩⟨N—CH₂Ph |
| 100 | carbazole (N-CH₂Ph) | 2 | piperazine —N⟩⟨N—CH₂Ph |
| 101 | phenoxazine (N-H) | 2 | piperidine-N—CH₂Ph |
| 102 | phenoxazine (N-Ac) | 2 | piperidine-N—CH₂Ph |

TABLE 7-continued

| No. | Ar | n | Y |
|---|---|---|---|
| 103 | 2-phenoxy-N-methylaniline linked to 4-methylphenyl | 2 | 4-piperidinyl-N—CH$_2$Ph |
| 104 | 2-phenoxy-NH-aniline linked to 4-methylphenyl | 2 | piperazinyl-N—CH$_2$Ph |
| 105 | 2-phenoxy-N-Ac-aniline linked to 4-methylphenyl | 2 | piperazinyl-N—CH$_2$Ph |

TABLE 8

| No. | Ar | n | Y |
|---|---|---|---|
| 106 | 2-phenyl-N-methylaniline linked via O to 4-methylphenyl | 2 | 4-piperidinyl-N—CH$_2$Ph |
| 107 | 2-phenyl-N-Ac-aniline linked via S to 4-methylphenyl | 2 | 4-piperidinyl-N—CH$_2$Ph |
| 108 | 2-phenyl-N-methylaniline linked via O to 4-methylphenyl | 2 | piperazinyl-N—CH$_2$Ph |
| 109 | 2-phenyl-N-Ac-aniline linked via S to 4-methylphenyl | 2 | piperazinyl-N—CH$_2$Ph |
| 110 | diphenyl dioxin, 4-methyl | 2 | 4-piperidinyl-N—CH$_2$Ph |
| 111 | 4,5-dimethylphenyl-dioxin-4'-methylphenyl | 2 | 4-piperidinyl-N—CH$_2$Ph |
| 112 | diphenyl dioxin, 4-methyl | 2 | piperazinyl-N—CH$_2$Ph |

TABLE 8-continued
| No. | Ar | n | Y |
|---|---|---|---|
| 113 | 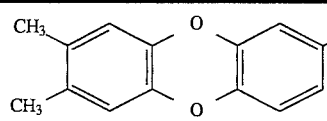 | 2 | 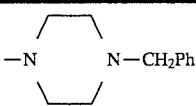 |
| 114 | 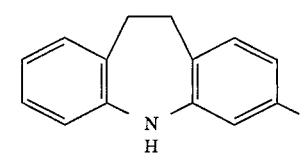 | 2 | 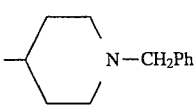 |
| 115 | 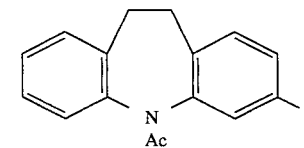 | 2 | 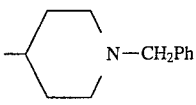 |
| 116 | 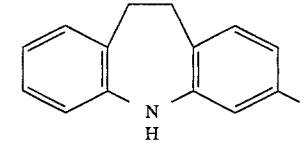 | 2 | 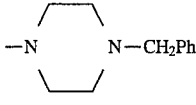 |
| 117 | 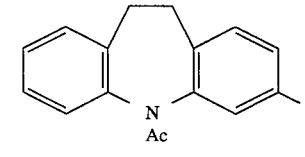 | 2 | 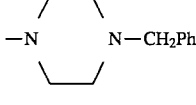 |
| 118 | 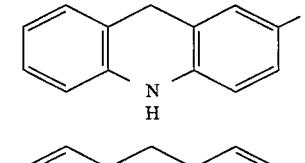 | 2 | 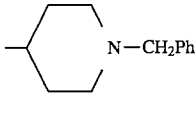 |
| 119 | 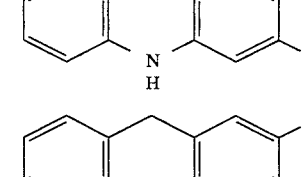 | 2 | 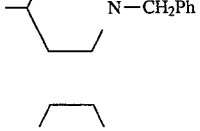 |
| 120 | 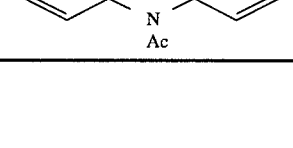 | 2 |  |
TABLE 9
| No. | Ar | n | Y |
|---|---|---|---|
| 121 | 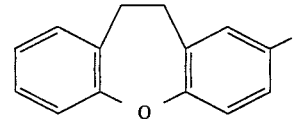 | 2 | 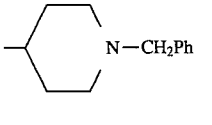 |
| 122 | 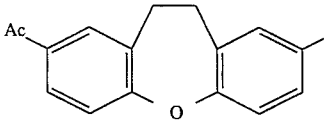 | 2 | 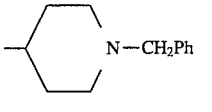 |

TABLE 9-continued
| No. | Ar | n | Y |
|-----|-----|---|---|
| 123 | 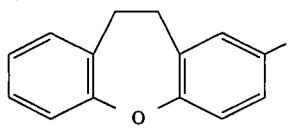 | 2 | 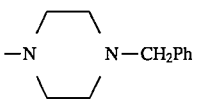 |
| 124 | 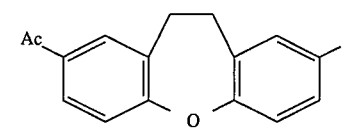 | 2 | 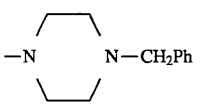 |
| 125 | 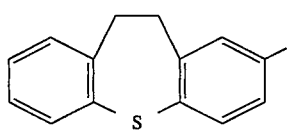 | 2 | 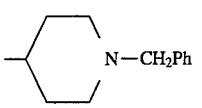 |
| 126 | 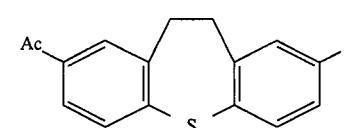 | 2 | 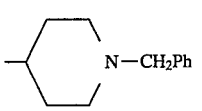 |
| 127 | 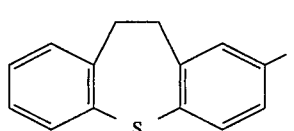 | 2 | 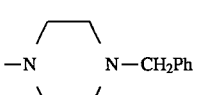 |
| 128 | 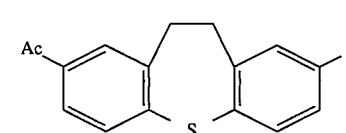 | 2 | 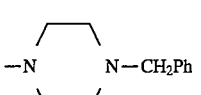 |
| 129 | 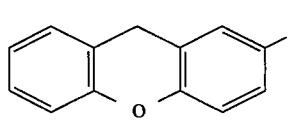 | 2 | 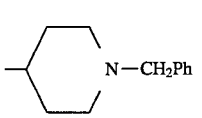 |
| 130 | 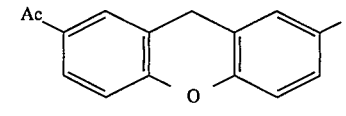 | 2 | 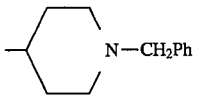 |
| 131 | 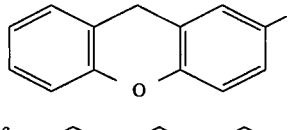 | 2 | 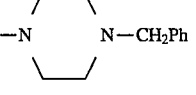 |
| 132 | 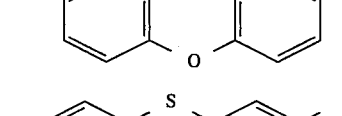 | 2 | 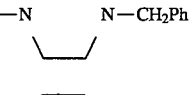 |
| 133 | 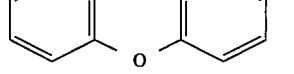 | 2 | 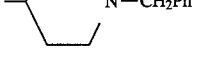 |

TABLE 10
| No. | Ar | n | Y |
|---|---|---|---|
| 134 | 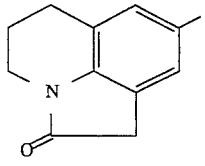 | 2 | 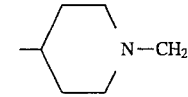 |
| 135 | 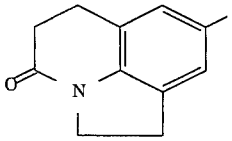 | 2 | 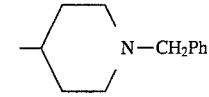 |
| 136 | 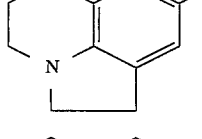 | 2 | 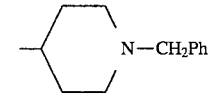 |
| 137 | 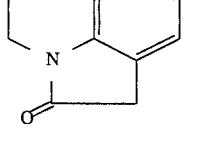 | 2 | 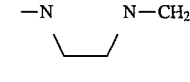 |
| 138 | 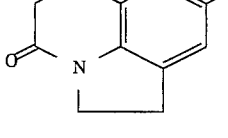 | 2 | 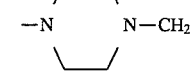 |
| 139 | 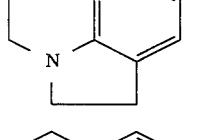 | 2 | 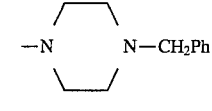 |
| 140 | 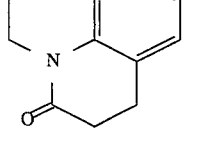 | 2 | 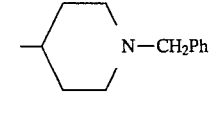 |
| 141 | 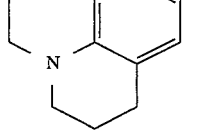 | 2 | 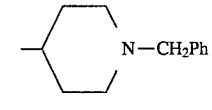 |
TABLE 10-continued
| No. | Ar | n | Y |
|---|---|---|---|
| 142 | 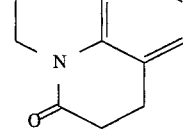 | 2 |  |
| 143 | 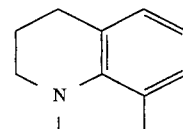 | 2 |  |
| 144 | 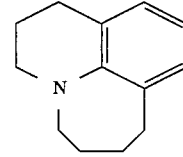 | 2 |  |
| 145 | 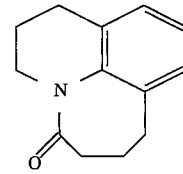 | 2 |  |
| 146 | 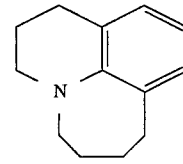 | 2 | 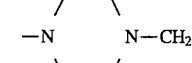 |
| 147 | 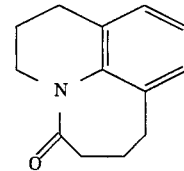 | 2 |  |
TABLE 11
| No. | Ar | n | Y |
|---|---|---|---|
| 148 |  | 2 |  |

TABLE 11-continued
| No. | Ar | n | Y |
|---|---|---|---|
| 149 | 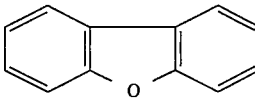 | 2 | 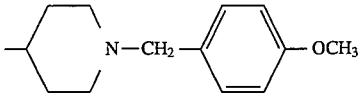 |
| 150 | 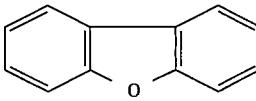 | 2 | 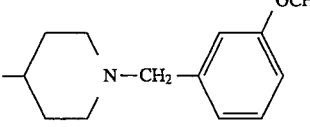 |
| 151 | 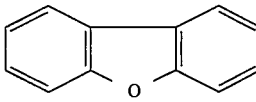 | 2 | 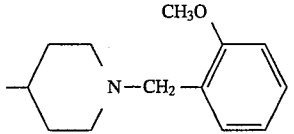 |
| 152 | 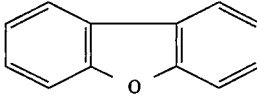 | 2 | 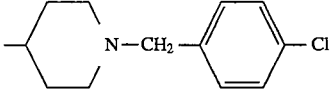 |
| 153 | 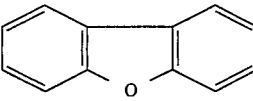 | 2 | 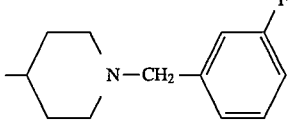 |
| 154 | 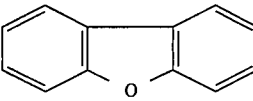 | 2 | 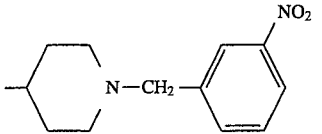 |
| 155 | 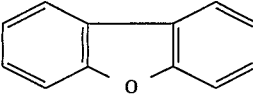 | 2 | 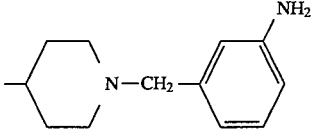 |
| 156 | 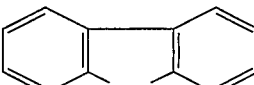 | 2 | 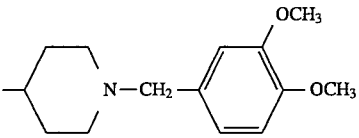 |
| 157 | 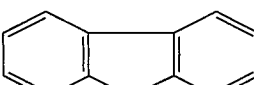 | 2 | 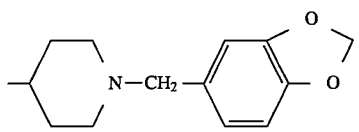 |
| 158 | 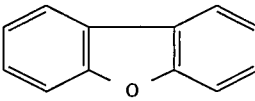 | 2 | 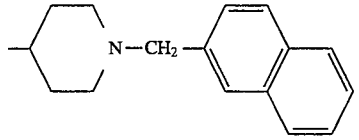 |
| 159 |  | 2 | 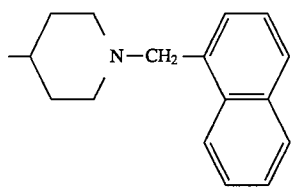 |

TABLE 12

| No. | Ar | n | Y |
| --- | --- | --- | --- |
| 160 | dibenzofuran | 2 | -N(piperazine)N-CH₂-C₆H₄-pyrrolidine |
| 161 | dibenzofuran | 2 | -N(piperazine)N-CH₂-indanyl |
| 162 | dibenzofuran | 2 | -N(piperazine)N-CH₂-C₆H₄-CN |
| 163 | dibenzofuran | 2 | -N(piperazine)N-CH₂-C₆H₄-CO₂CH₃ |
| 164 | dibenzofuran | 2 | -N(piperazine)N-C₆H₄-Cl |
| 165 | dibenzofuran | 2 | -N(piperazine)N-CHPh₂ |
| 166 | dibenzofuran | 2 | -N(piperazine)N-(2-pyridyl) |
| 167 | dibenzofuran | 2 | -N(piperazine)N-(pyrimidinyl) |
| 168 | dibenzofuran | 2 | -N(piperazine)N-CH₂-(4-pyridyl) |
| 169 | dibenzofuran | 2 | -N(piperazine)N-CH(CH₃)-Ph |
| 170 | dibenzofuran | 2 | -N(piperazine)N-CH₂-(furyl) |
| 171 | dibenzofuran | 2 | -N(piperazine)N-CH₂-(2-methylthiazolyl) |

TABLE 13

| No. | Ar | n | Y |
|---|---|---|---|
| 172 | (pyrrolidine fused to benzene, NH, H, NH) | 2 | piperidine-N—CH₂Ph |
| 173 | (pyrrolidine fused to benzene, CH₃, H, NH, NH) | 2 | piperidine-N—CH₂Ph |
| 174 | (pyrrolidine fused to benzene, H, N—CH₃, N—CH₃) | 2 | piperidine-N—CH₂Ph |
| 175 | (pyrrolidine fused to benzene, CH₃, H, N—CH₃, N—CH₃) | 2 | piperidine-N—CH₂Ph |
| 176 | (pyrrolidine fused to benzene, H, NH, NH) | 2 | —N-piperazine-N—CH₂Ph |
| 177 | (pyrrolidine fused to benzene, CH₃, H, NH, NH) | 2 | —N-piperazine-N—CH₂Ph |
| 178 | (pyrrolidine fused to benzene, H, N—CH₃, N—CH₃) | 2 | —N-piperazine-N—CH₂Ph |
| 179 | (pyrrolidine fused to benzene, CH₃, H, N—CH₃, N—CH₃) | 2 | —N-piperazine-N—CH₂Ph |
| 180 | (pyrrolidine fused to benzene, CH₃, H, N—CH₃, N—CH₃) | 2 | —N-piperazine-N—CH₂Ph |

TABLE 14
| No. | Ar | n | Y |
|---|---|---|---|
| 181 | 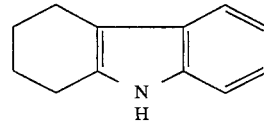 | 2 | 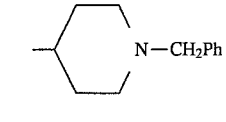 |
| 182 | 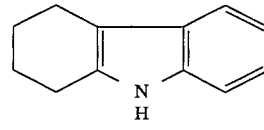 | 2 | 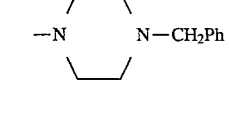 |
| 183 | 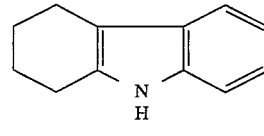 | 2 | 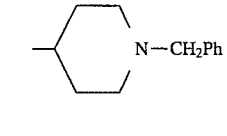 |
| 184 | 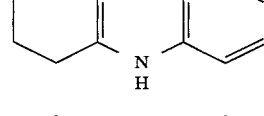 | 2 | 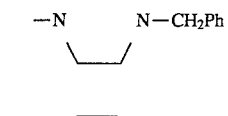 |
| 185 | 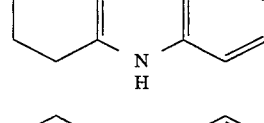 | 2 | 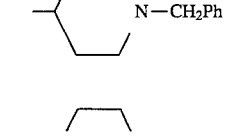 |
| 186 | 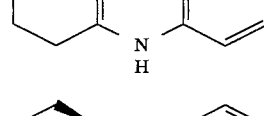 | 2 | 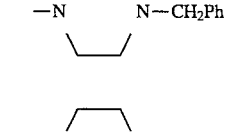 |
| 187 | 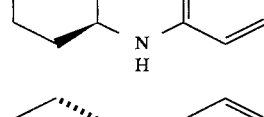 | 2 | 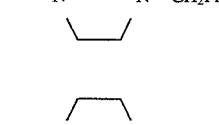 |
| 188 | 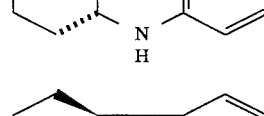 | 2 |  |
| 189 | 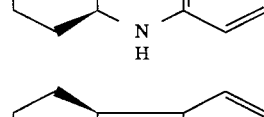 | 2 | 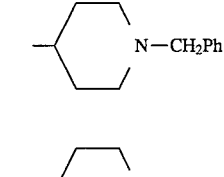 |
| 190 | 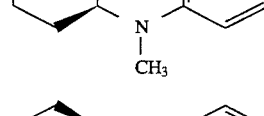 | 2 | 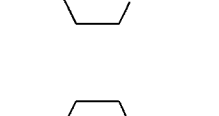 |
| 191 | 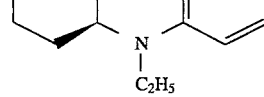 | 2 | 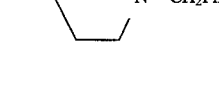 |

TABLE 14-continued

| No. | Ar | n | Y |
|---|---|---|---|
| 192 | (trans-hexahydrocarbazole, 6-methyl, N-C₃H₇) | 2 | 4-(N-CH₂Ph)piperidinyl |

TABLE 15

| No. | Ar | n | Y |
|---|---|---|---|
| 193 | (trans-hexahydrocarbazole, 6-methyl, N-CH(CH₃)₂) | 2 | 4-(N-CH₂Ph)piperidinyl |
| 194 | (trans-hexahydrocarbazole, 6-methyl, N-(CH₂)₃CH₃) | 2 | 4-(N-CH₂Ph)piperidinyl |
| 195 | (trans-hexahydrocarbazole, 6-methyl, N-CH₂CH(CH₃)₂) | 2 | 4-(N-CH₂Ph)piperidinyl |
| 196 | (trans-hexahydrocarbazole, 6-methyl, N-CH₂Ph) | 2 | 4-(N-CH₂Ph)piperidinyl |
| 197 | (trans-hexahydrocarbazole, 6-methyl, N-CH₂-C₆H₄-4-OCH₃) | 2 | 4-(N-CH₂Ph)piperidinyl |
| 198 | (trans-hexahydrocarbazole, 6-methyl, N-CH₂-C₆H₃-2,4-(OCH₃)₂) | 2 | 4-(N-CH₂Ph)piperidinyl |
| 199 | (trans-hexahydrocarbazole, 6-methyl, N-CHO) | 2 | 4-(N-CH₂Ph)piperidinyl |

TABLE 15-continued
| No. | Ar | n | Y |
|---|---|---|---|
| 200 | 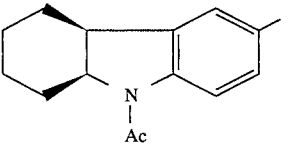 | 2 | 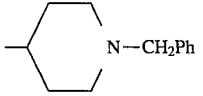 |
| 201 | 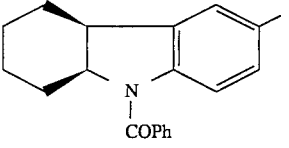 | 2 | 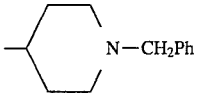 |
| 202 | 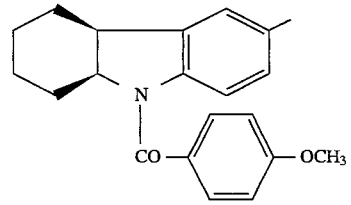 | 2 | 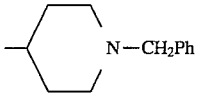 |
TABLE 16
| No. | Ar | n | Y |
|---|---|---|---|
| 203 | 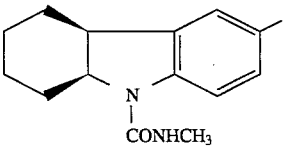 | 2 | 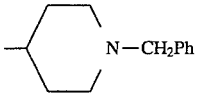 |
| 204 | 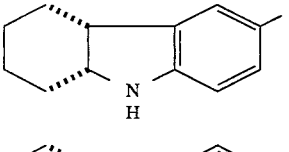 | 2 | 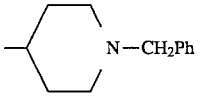 |
| 205 | 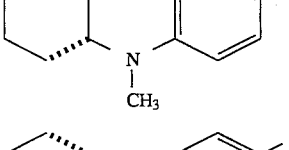 | 2 | 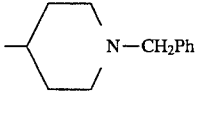 |
| 206 | 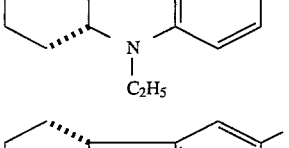 | 2 | 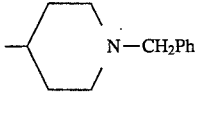 |
| 207 | 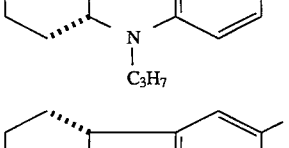 | 2 | 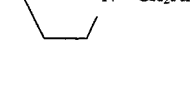 |
| 208 | 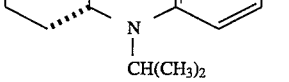 | 2 | 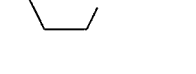 |

TABLE 16-continued

| No. | Ar | n | Y |
|---|---|---|---|
| 209 | hexahydrocarbazole, N-(CH2)3CH3, methyl on benzene ring | 2 | piperidine-N-CH2Ph |
| 210 | hexahydrocarbazole, N-CH2CH(CH3)2, methyl on benzene ring | 2 | piperidine-N-CH2Ph |
| 211 | hexahydrocarbazole, N-CH2Ph, methyl on benzene ring | 2 | piperidine-N-CH2Ph |
| 212 | hexahydrocarbazole, N-CH2-Ph, methyl on benzene ring | 2 | piperidine-N-CH2Ph |
| 213 | hexahydrocarbazole, N-CH2-(2,3-dimethoxyphenyl), methyl and OCH3 on benzene ring | 2 | piperidine-N-CH2Ph |

TABLE 17

| No. | Ar | n | Y |
|---|---|---|---|
| 214 | hexahydrocarbazole, N-CHO, methyl on benzene ring | 2 | piperidine-N-CH2Ph |
| 215 | hexahydrocarbazole, N-Ac, methyl on benzene ring | 2 | piperidine-N-CH2Ph |
| 216 | hexahydrocarbazole, N-COPh, methyl on benzene ring | 2 | piperidine-N-CH2Ph |

TABLE 17-continued

| No. | Ar | n | Y |
|---|---|---|---|
| 217 | hexahydrocarbazole with N-CO-C6H4-OCH3 | 2 | piperidine N—CH2Ph |
| 218 | hexahydrocarbazole with N-COHNCH3 | 2 | piperidine N—CH2Ph |
| 219 | hexahydrocarbazole with N-CO2CH3 | 2 | piperidine N—CH2Ph |
| 220 | hexahydrocarbazole with N-CO2CH3 | 2 | piperidine N—CH2Ph |
| 221 | tetrahydronaphthalene with CH2—N—C2H5 | 2 | piperidine N—CH2Ph |
| 222 | tetrahydronaphthalene with CH2—N—C3H7 | 2 | piperidine N—CH2Ph |
| 223 | tetrahydronaphthalene with CH2—N—CH(CH3)2 | 2 | piperidine N—CH2Ph |
| 224 | tetrahydronaphthalene with CH2—N—(CH2)3CH3 | 2 | piperidine N—CH2Ph |

TABLE 18

| No. | Ar | n | Y |
|---|---|---|---|
| 225 | tetrahydronaphthalene-CH2-N-CH2CH(CH3)2 | 2 | 4-(N-benzyl)piperidinyl |
| 226 | tetrahydronaphthalene-CH2-N-CO-CH2CH3 | 2 | 4-(N-benzyl)piperidinyl |
| 227 | tetrahydronaphthalene-CH2-N-CO-(CH2)2-CH3 | 2 | 4-(N-benzyl)piperidinyl |
| 228 | tetrahydronaphthalene-CH2-N-CO-CH2-CH(CH3)2 | 2 | 4-(N-benzyl)piperidinyl |
| 229 | tetrahydronaphthalene-CH2-N-CH2-(3,4-dimethoxyphenyl) | 2 | 4-(N-benzyl)piperidinyl |
| 230 | tetrahydronaphthalene-CH2-N-CH2-(3-methoxyphenyl) | 2 | 4-(N-benzyl)piperidinyl |
| 231 | tetrahydronaphthalene-CH2-N-CH2-(2-methoxyphenyl) | 2 | 4-(N-benzyl)piperidinyl |
| 232 | tetrahydronaphthalene-CH2-N-CH2-(4-chlorophenyl) | 2 | 4-(N-benzyl)piperidinyl |

TABLE 18-continued

| No. | Ar | n | Y |
|---|---|---|---|
| 233 | tetrahydronaphthalene-CH2-N-CH2-(3-Cl-phenyl) | 2 | piperidine-N-CH2Ph |
| 234 | tetrahydronaphthalene-CH2-N-CH2-(3-F-phenyl) | 2 | piperidine-N-CH2Ph |
| 235 | tetrahydronaphthalene-CH2-N-CO-(4-OCH3-phenyl) | 2 | piperidine-N-CH2Ph |

TABLE 19

| No. | Ar | n | Y |
|---|---|---|---|
| 236 | tetrahydronaphthalene-CH2-N-CO-(4-Cl-phenyl) | 2 | piperidine-N-CH2Ph |
| 237 | tetrahydronaphthalene-CH2-N-CO-(4-NO2-phenyl) | 2 | piperidine-N-CH2Ph |
| 238 | tetrahydronaphthalene-CH2-N-CONHCH3 | 2 | piperidine-N-CH2Ph |
| 239 | tetrahydronaphthalene-CH2-N-CO2CH3 | 2 | piperidine-N-CH2Ph |

TABLE 19-continued

| No. | Ar | n | Y |
|---|---|---|---|
| 240 | (tetrahydronaphthalene fused, N—CONHPh) | 2 | piperidine-N—CH$_2$Ph |
| 241 | (benzocycloheptane fused, NH) | 2 | piperidine-N—CH$_2$Ph |
| 242 | (benzocycloheptane fused, N—CH$_3$) | 2 | piperidine-N—CH$_2$Ph |
| 243 | (benzocycloheptane fused, N—C$_2$H$_5$) | 2 | piperidine-N—CH$_2$Ph |
| 244 | (benzocycloheptane fused, N—CHO) | 2 | piperidine-N—CH$_2$Ph |
| 245 | (benzocycloheptane fused, N—Ac) | 2 | piperidine-N—CH$_2$Ph |
| 246 | (benzocycloheptane fused, N—CH$_2$Ph) | 2 | piperidine-N—CH$_2$Ph |

TABLE 20

| No. | Ar | n | Y |
|---|---|---|---|
| 247 | (benzocycloheptane fused, N—CH$_3$—C$_6$H$_4$—OCH$_3$) | 2 | piperidine-N—CH$_2$Ph |

TABLE 20-continued

| No. | Ar | n | Y |
|---|---|---|---|
| 248 | (tricyclic Ar with CH2–N–COPh) | 2 | piperidine N–CH2Ph |
| 249 | (tricyclic Ar with CH2–N–CO–C6H4–OCH3) | 2 | piperidine N–CH2Ph |
| 250 | (tricyclic Ar with CH2–N–CO2C2H5) | 2 | piperidine N–CH2Ph |
| 251 | (benzazepinone Ar, methyl substituent) | 2 | piperidine N–CH2Ph |
| 252 | (benzazepinone Ar, methyl substituent) | 2 | piperidine N–CH2Ph |
| 253 | (benzazepinone Ar, methyl substituent) | 2 | –N(piperazine)N–CH2Ph |
| 254 | (benzazepinone Ar, methyl substituent) | 2 | –N(piperazine)N–CH2Ph |
| 255 | (benzazepinone Ar, methyl and Cl substituents) | 2 | piperidine N–CH2Ph |
| 256 | (benzazepinone Ar, Cl and methyl substituents) | 2 | piperidine N–CH2Ph |

TABLE 20-continued
| No. | Ar | n | Y |
|---|---|---|---|
| 257 |  | 2 | 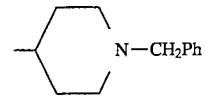 |
| 258 | 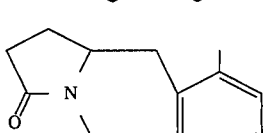 | 2 | 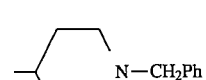 |
| 259 | 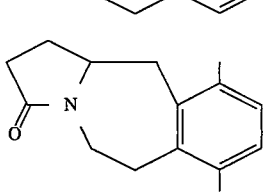 | 2 | 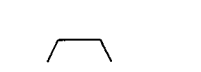 |
TABLE 21
| No. | Ar | n | Y |
|---|---|---|---|
| 260 | 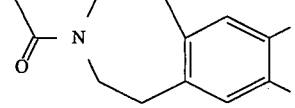 | 2 | 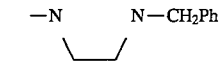 |
| 261 | 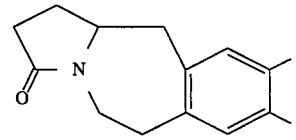 | 2 | 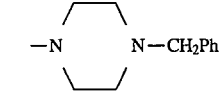 |
| 262 | 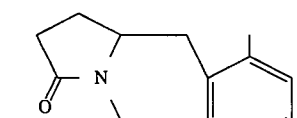 | 2 | 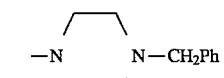 |
| 263 | 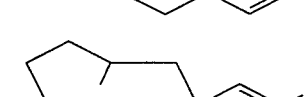 | 2 |  |
| 264 |  | 2 |  |
| 265 |  | 2 | 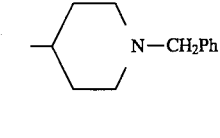 |

TABLE 21-continued

| No. | Ar | n | Y |
|---|---|---|---|
| 266 | (pyrrolidine-fused benzyl with methyl) | 2 | —N(piperazine)N—CH$_2$Ph |
| 267 | (biphenyl with CH$_2$OHCN and methyl) | 2 | —N(piperazine)N—CH$_2$Ph |
| 268 | (biphenyl with CH$_2$NH and methyl) | 2 | —N(piperazine)N—CH$_2$Ph |
| 269 | (dibenzazepine with N-CHO, methyl) | 2 | —N(piperazine)N—CH$_2$Ph |
| 270 | (dibenzazepine with NH, methyl) | 2 | —N(piperazine)N—CH$_2$Ph |
| 271 | (dibenzazepine with NH, methyl) | 2 | (piperidine)N—CH$_2$Ph |

TABLE 22

| No. | Ar | n | Y |
|---|---|---|---|
| 272 | (dibenzazepine with N-CHO, methyl) | 2 | (piperidine)N—CH$_2$Ph |
| 273 | (tetrahydronaphthalene with C(=O)NH, methyl) | 2 | (piperidine)N—CH$_2$Ph |

TABLE 22-continued

| No. | Ar | n | Y |
|---|---|---|---|
| 274 | (naphthalene with NH-C(=O)) | 2 | piperidine-N—CH₂Ph |
| 275 | (tetrahydronaphthalene with NH-C(=O)) | 2 | —N(piperazine)N—CH₂Ph |
| 276 | (naphthalene with NH-C(=O)) | 2 | —N(piperazine)N—CH₂Ph |
| 277 | (benzazepine with CH₃, C=O) | 2 | piperidine-N—CH₂Ph |
| 278 | (benzazepine with CH₃, C=O) | 2 | —N(piperazine)N—CH₂Ph |
| 279 | (benzazepine with C=O) | 2 | piperidine-N—CH₂Ph |
| 280 | (benzazepine with C=O) | 2 | —N(piperazine)N—CH₂Ph |
| 281 | (tricyclic benzazepine) | 2 | piperidine-N—CH₂Ph |
| 282 | (benzazepine with CH₃, C=O) | 2 | piperidine-N—CH₂Ph |
| 283 | (benzazepine with C=O) | 2 | —N(piperazine)N—CH₂Ph |

TABLE 23

| No. | Ar | n | Y |
|---|---|---|---|
| 284 | (tricyclic) | 2 | —N(piperidine)CH₂Ph |
| 285 | (tricyclic) | 2 | —N(piperidine)CH₂Ph |
| 286 | (tricyclic) | 2 | —N(piperidine)CH₂Ph |
| 287 | (tricyclic) | 2 | —N(piperidine)CH₂Ph |
| 288 | (tricyclic) | 2 | —N(piperidine)COPh |
| 289 | (tricyclic) | 2 | —N(piperidine)=CHPh |

TABLE 23-continued

| No. | Ar | n | Y |
|---|---|---|---|
| 290 | (tricyclic lactam structure with methyl) | 2 | —N(piperazine)N—COPh |
| 291 | (tricyclic lactam structure with methyl) | 2 | (piperidine)N—COPh |
| 292 | (tricyclic lactam structure with methyl) | 2 | —N(piperidine)—COPh |
| 293 | (tricyclic lactam structure with methyl) | 2 | —N(piperidine)=CHPh |
| 294 | (tricyclic lactam structure with methyl) | 2 | —N(piperazine)N—COPh |
| 295 | (tricyclic lactam structure with methyl) | 2 | (piperidine)N—COPh |

TABLE 24

| No. | Ar | n | Y |
|---|---|---|---|
| 296 | (tricyclic lactam structure with methyl, larger ring) | 2 | —N(piperidine)—COPh |
| 297 | (tricyclic lactam structure with methyl) | 2 | —N(piperidine)—COPh |
| 298 | (tricyclic lactam structure with methyl) | 2 | —N(piperazine)N—CH$_2$—(2-CH$_3$-phenyl) |
| 299 | (tricyclic lactam structure with methyl) | 2 | —N(piperazine)N—CH$_2$—(3-CH$_3$-phenyl) |
| 300 | (tricyclic lactam structure with methyl) | 2 | —N(piperazine)N—CH$_2$—(4-CH$_3$-phenyl) |

TABLE 24-continued
| No. | Ar | n | Y |
|---|---|---|---|
| 301 | 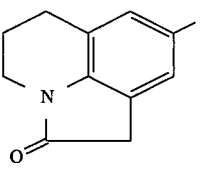 | 2 | 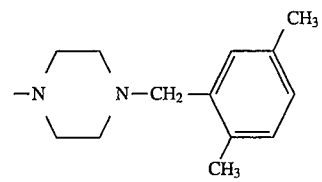 |
| 302 | 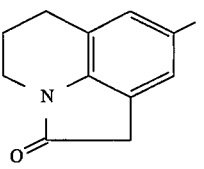 | 2 | 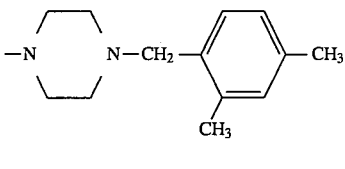 |
| 303 | 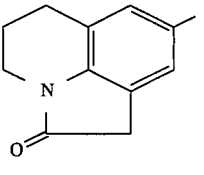 | 2 | 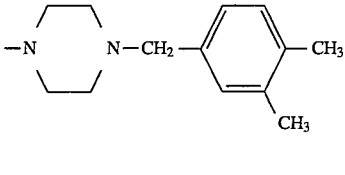 |
| 304 | 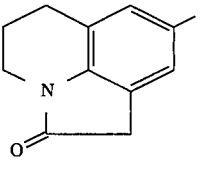 | 2 | 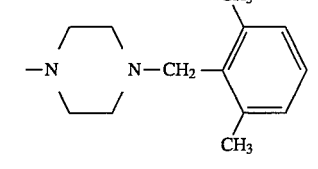 |
| 305 | 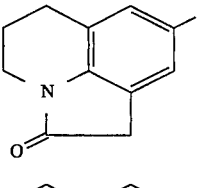 | 2 | 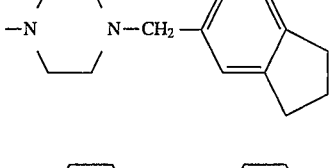 |
| 306 | 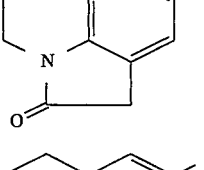 | 2 | 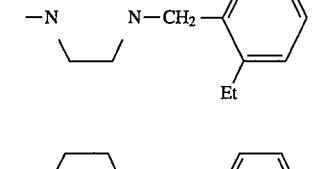 |
| 307 | 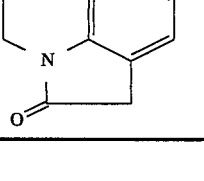 | 2 | 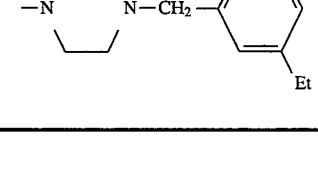 |
TABLE 25
| No. | Ar | n | Y |
|---|---|---|---|
| 308 | 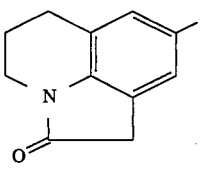 | 2 | 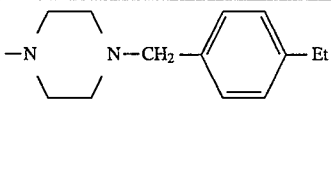 |

TABLE 25-continued
| No. | Ar | n | Y |
|---|---|---|---|
| 309 | 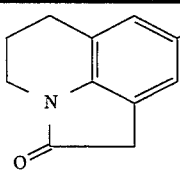 | 2 | 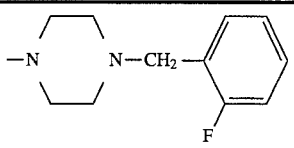 |
| 310 | 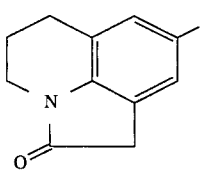 | 2 | 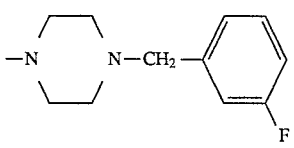 |
| 311 | 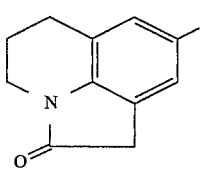 | 2 | 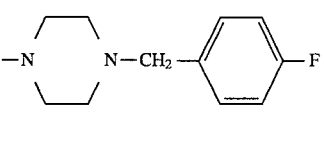 |
| 312 | 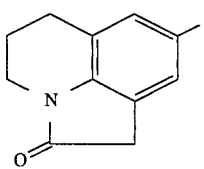 | 2 | 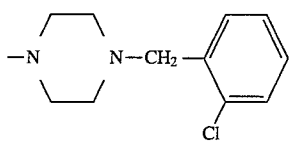 |
| 313 |  | 2 | 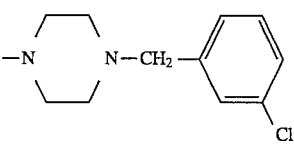 |
| 314 |  | 2 | 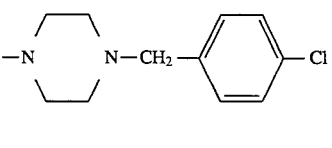 |
| 315 | 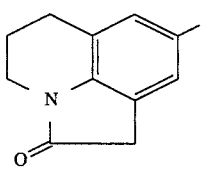 | 2 | 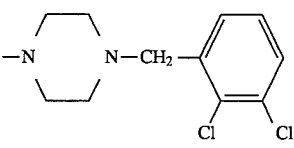 |
| 316 | 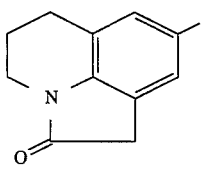 | 2 | 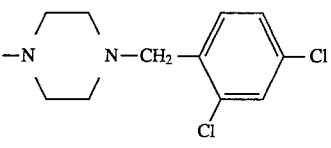 |
| 317 |  | 2 | 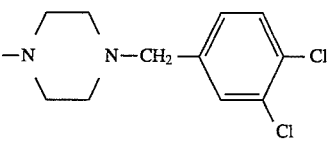 |

TABLE 25-continued

| No. | Ar | n | Y |
|---|---|---|---|
| 318 | (tricyclic lactam) | 2 | piperazine-N-CH₂-(2,6-dichlorophenyl) |
| 319 | (tricyclic lactam) | 2 | piperazine-N-CH₂-(2-hydroxyphenyl) |

TABLE 26

| No. | Ar | n | Y |
|---|---|---|---|
| 320 | (tricyclic lactam) | 2 | piperazine-N-CH₂-(3-hydroxyphenyl) |
| 321 | (tricyclic lactam) | 2 | piperazine-N-CH₂-(4-hydroxyphenyl) |
| 322 | (tricyclic lactam) | 2 | piperazine-N-CH₂-(2-methoxyphenyl) |
| 323 | (tricyclic lactam) | 2 | piperazine-N-CH₂-(3-methoxyphenyl) |
| 324 | (tricyclic lactam) | 2 | piperazine-N-CH₂-(4-methoxyphenyl) |
| 325 | (tricyclic lactam) | 2 | piperazine-N-CH₂-(3,4-dimethoxyphenyl) |

TABLE 26-continued
| No. | Ar | n | Y |
|---|---|---|---|
| 326 | 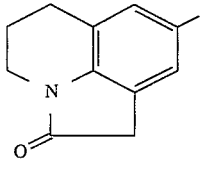 | 2 | 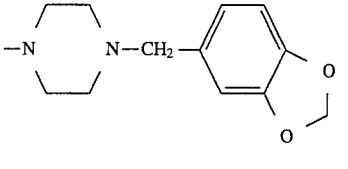 |
| 327 | 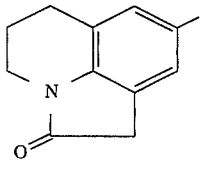 | 2 | 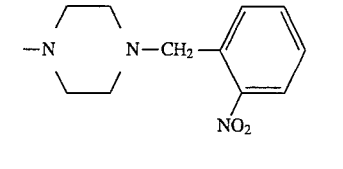 |
| 328 | 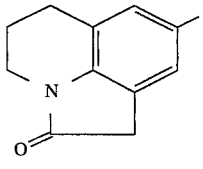 | 2 | 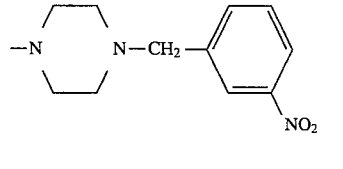 |
| 329 | 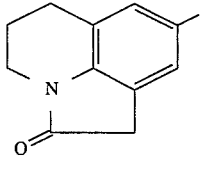 | 2 | 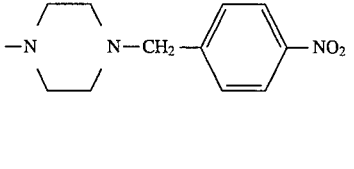 |
| 330 | 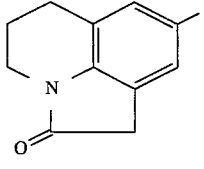 | 2 | 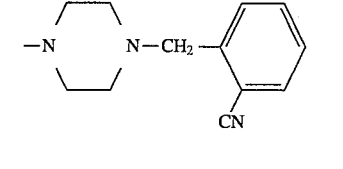 |
| 331 | 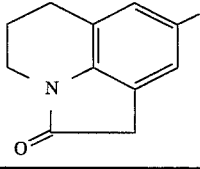 | 2 | 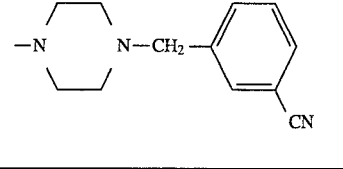 |
TABLE 27
| No. | Ar | n | Y |
|---|---|---|---|
| 332 | 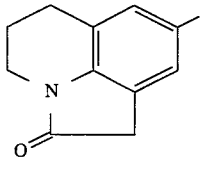 | 2 | 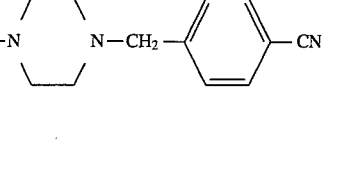 |
| 333 | 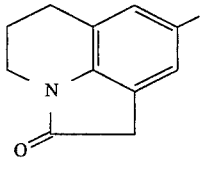 | 2 | 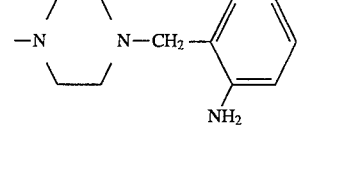 |

TABLE 27-continued
| No. | Ar | n | Y |
|---|---|---|---|
| 334 | 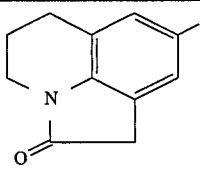 | 2 | 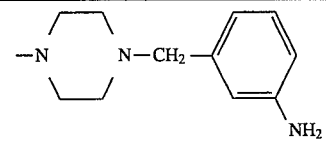 |
| 335 | 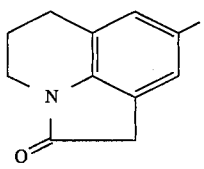 | 2 | 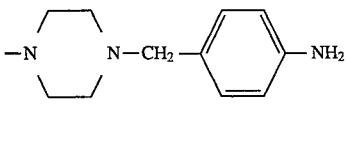 |
| 336 |  | 2 | 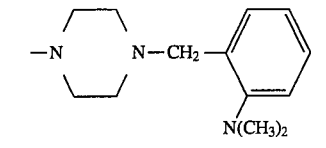 |
| 337 |  | 2 | 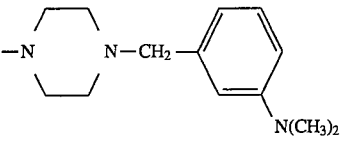 |
| 338 | 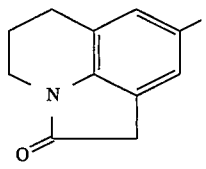 | 2 | 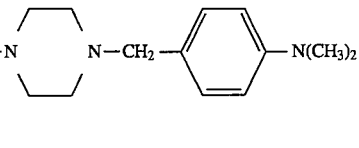 |
| 339 | 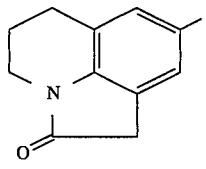 | 2 | 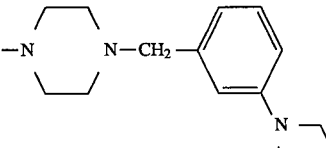 |
| 340 | 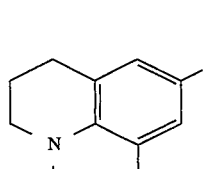 | 2 | 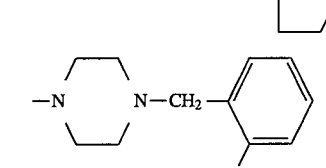 |
| 341 | 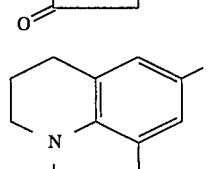 | 2 | 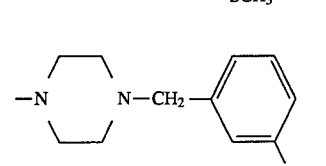 |
| 342 | 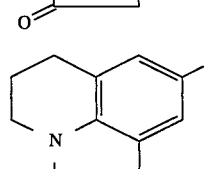 | 2 | 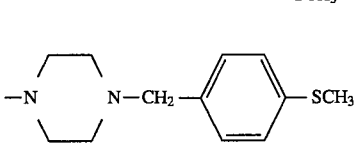 |

TABLE 27-continued
| No. | Ar | n | Y |
|-----|----|----|---|
| 343 | 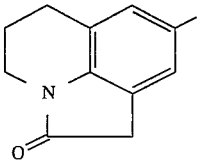 | 2 | 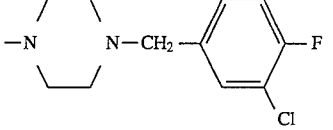 |
TABLE 28
| No. | Ar | n | Y |
|-----|----|----|---|
| 344 | 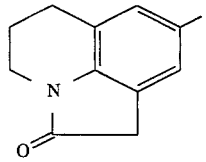 | 2 | 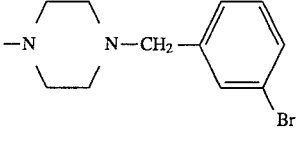 |
| 345 | 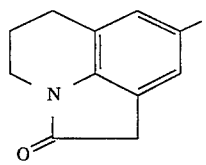 | 2 | 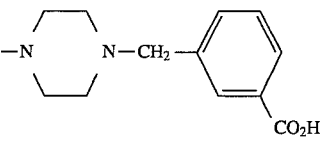 |
| 346 | 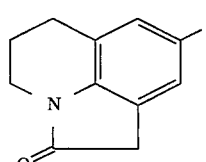 | 2 | 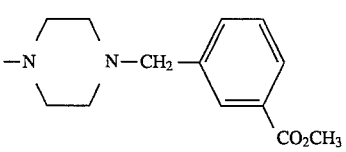 |
| 347 | 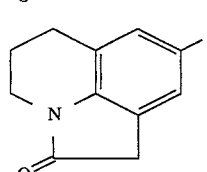 | 2 | 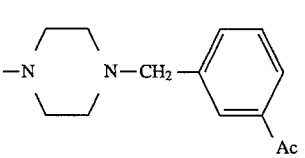 |
| 348 | 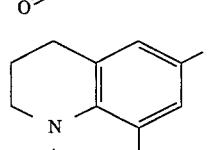 | 2 | 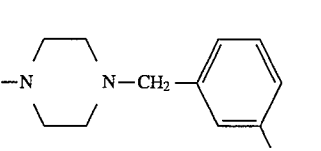 |
| 349 | 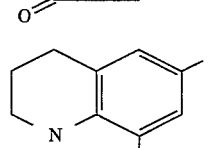 | 2 | 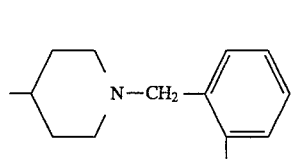 |
| 350 | 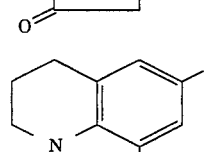 | 2 | 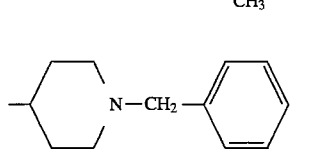 |

TABLE 28-continued

| No. | Ar | n | Y |
|---|---|---|---|
| 351 | (tricyclic lactam) | 2 | piperidine-N-CH₂-(4-methylphenyl) |
| 352 | (tricyclic lactam) | 2 | piperidine-N-CH₂-(2,5-dimethylphenyl) |
| 353 | (tricyclic lactam) | 2 | piperidine-N-CH₂-(2,4-dimethylphenyl) |
| 354 | (tricyclic lactam) | 2 | piperidine-N-CH₂-(3,4-dimethylphenyl) |
| 355 | (tricyclic lactam) | 2 | piperidine-N-CH₂-(2,6-dimethylphenyl) |

TABLE 29

| No. | Ar | n | Y |
|---|---|---|---|
| 356 | (tricyclic lactam) | 2 | piperidine-N-CH₂-(indanyl) |
| 357 | (tricyclic lactam) | 2 | piperidine-N-CH₂-(2-ethylphenyl) |
| 358 | (tricyclic lactam) | 2 | piperidine-N-CH₂-(3-ethylphenyl) |

TABLE 29-continued
| No. | Ar | n | Y |
|---|---|---|---|
| 359 | 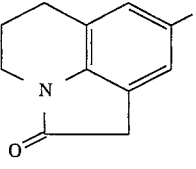 | 2 | 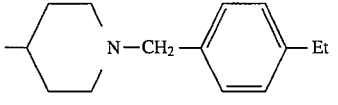 |
| 360 | 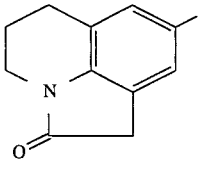 | 2 | 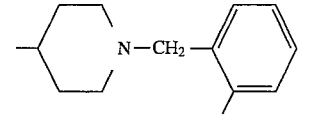 |
| 361 | 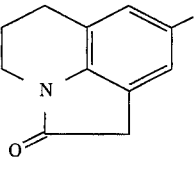 | 2 | 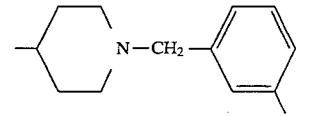 |
| 362 | 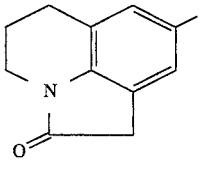 | 2 | 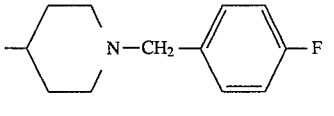 |
| 363 | 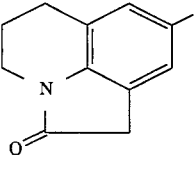 | 2 | 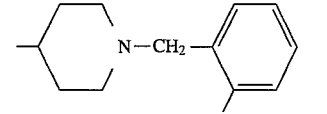 |
| 364 | 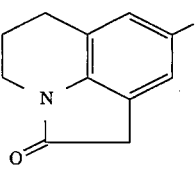 | 2 | 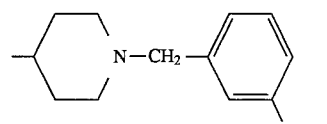 |
| 365 | 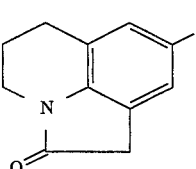 | 2 | 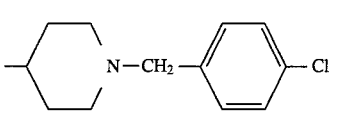 |
| 366 | 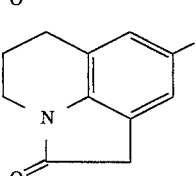 | 2 | 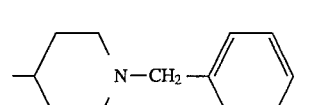 |
| 367 | 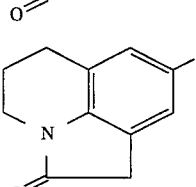 | 2 | 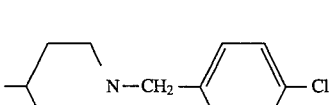 |

TABLE 30

| No. | Ar | n | Y |
|---|---|---|---|
| 368 | (tricyclic lactam) | 2 | piperidine-N-CH₂-(3,4-dichlorophenyl) |
| 369 | (tricyclic lactam) | 2 | piperidine-N-CH₂-(2,6-dichlorophenyl) |
| 370 | (tricyclic lactam) | 2 | piperidine-N-CH₂-(2-hydroxyphenyl) |
| 371 | (tricyclic lactam) | 2 | piperidine-N-CH₂-(3-hydroxyphenyl) |
| 372 | (tricyclic lactam) | 2 | piperidine-N-CH₂-(4-hydroxyphenyl) |
| 373 | (tricyclic lactam) | 2 | piperidine-N-CH₂-(2-methoxyphenyl) |
| 374 | (tricyclic lactam) | 2 | piperidine-N-CH₂-(3-methoxyphenyl) |
| 375 | (tricyclic lactam) | 2 | piperidine-N-CH₂-(4-methoxyphenyl) |
| 376 | (tricyclic lactam) | 2 | piperidine-N-CH₂-(3,4-dimethoxyphenyl) |

TABLE 30-continued

| No. | Ar | n | Y |
|-----|-----|---|---|
| 377 | tricyclic lactam | 2 | piperidine-N-CH₂-(3,4-methylenedioxyphenyl) |
| 378 | tricyclic lactam | 2 | piperidine-N-CH₂-(2-NO₂-phenyl) |
| 379 | tricyclic lactam | 2 | piperidine-N-CH₂-(3-NO₂-phenyl) |

TABLE 31

| No. | Ar | n | Y |
|-----|-----|---|---|
| 380 | tricyclic lactam | 2 | piperidine-N-CH₂-(4-NO₂-phenyl) |
| 381 | tricyclic lactam | 2 | piperidine-N-CH₂-(2-CN-phenyl) |
| 382 | tricyclic lactam | 2 | piperidine-N-CH₂-(3-CN-phenyl) |
| 383 | tricyclic lactam | 2 | piperidine-N-CH₂-(4-CN-phenyl) |
| 384 | tricyclic lactam | 2 | piperidine-N-CH₂-(2-NH₂-phenyl) |

TABLE 31-continued
| No. | Ar | n | Y |
|---|---|---|---|
| 385 | 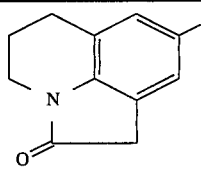 | 2 | 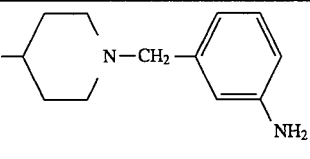 |
| 386 | 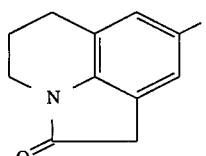 | 2 | 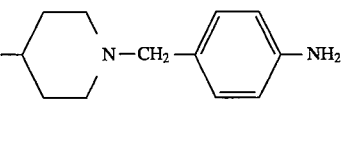 |
| 387 | 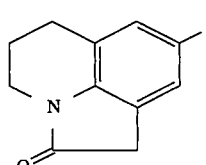 | 2 | 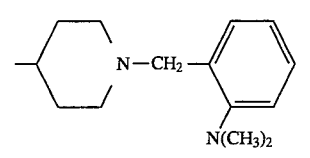 |
| 388 | 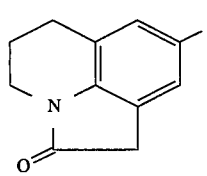 | 2 | 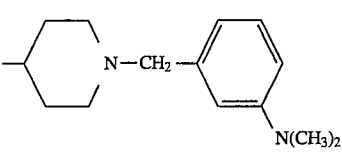 |
| 389 | 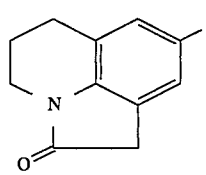 | 2 | 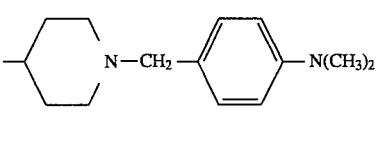 |
| 390 | 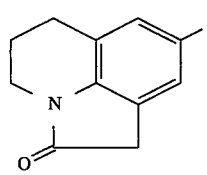 | 2 | 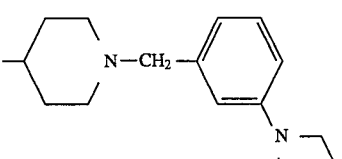 |
| 391 | 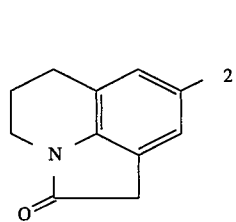 | 2 | 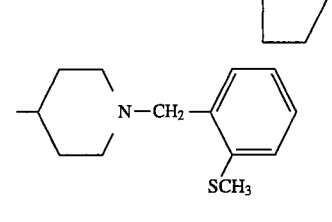 |
TABLE 32
| No. | Ar | n | Y |
|---|---|---|---|
| 392 | 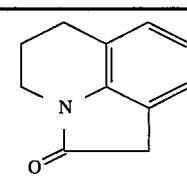 | 2 | 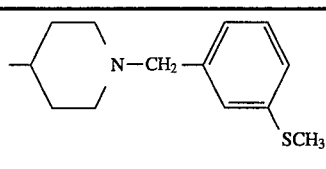 |

TABLE 32-continued

| No. | Ar | n | Y |
|---|---|---|---|
| 393 | (tricyclic lactam) | 2 | piperidine-N-CH₂-C₆H₄-SCH₃ |
| 394 | (tricyclic lactam) | 2 | piperidine-N-CH₂-C₆H₃(F)(Cl) |
| 395 | (tricyclic lactam) | 2 | piperidine-N-CH₂-C₆H₄-Br |
| 396 | (tricyclic lactam) | 2 | piperidine-N-CH₂-C₆H₄-CO₂H |
| 397 | (tricyclic lactam) | 2 | piperidine-N-CH₂-C₆H₄-CO₂CH₃ |
| 398 | (tricyclic lactam) | 2 | piperidine-N-CH₂-C₆H₄-Ac |
| 399 | (tricyclic lactam) | 2 | piperidine-N-CH₂-C₆H₄-NHAc |
| 400 | (tricyclic lactam) | 2 | piperazine-N-CH₂-C₆H₄-CH₃ |
| 401 | (tricyclic lactam) | 2 | piperazine-N-CH₂-C₆H₄-CH₃ |

TABLE 32-continued

| No. | Ar | n | Y |
|---|---|---|---|
| 402 | (tricyclic lactam) | 2 | −N(piperazine)N−CH₂−C₆H₄−CH₃ (para) |
| 403 | (tricyclic lactam) | 2 | −N(piperazine)N−CH₂−C₆H₃(CH₃)₂ (2,5-dimethyl) |

TABLE 33

| No. | Ar | n | Y |
|---|---|---|---|
| 404 | (tricyclic lactam) | 2 | −N(piperazine)N−CH₂−C₆H₃(CH₃)₂ (2,4-dimethyl) |
| 405 | (tricyclic lactam) | 2 | −N(piperazine)N−CH₂−C₆H₃(CH₃)₂ (3,4-dimethyl) |
| 406 | (tricyclic lactam) | 2 | −N(piperazine)N−CH₂−C₆H₃(CH₃)₂ (2,6-dimethyl) |
| 407 | (tricyclic lactam) | 2 | −N(piperazine)N−CH₂−(indanyl) |
| 408 | (tricyclic lactam) | 2 | −N(piperazine)N−CH₂−C₆H₄−Et (ortho) |
| 409 | (tricyclic lactam) | 2 | −N(piperazine)N−CH₂−C₆H₄−Et (meta) |

TABLE 33-continued

| No. | Ar | n | Y |
|---|---|---|---|
| 410 | (tricyclic lactam with methyl) | 2 | –N(piperazine)N–CH$_2$–C$_6$H$_4$–Et (4-) |
| 411 | (tricyclic lactam with methyl) | 2 | –N(piperazine)N–CH$_2$–C$_6$H$_4$–F (2-) |
| 412 | (tricyclic lactam with methyl) | 2 | –N(piperazine)N–CH$_2$–C$_6$H$_4$–F (3-) |
| 413 | (tricyclic lactam with methyl) | 2 | –N(piperazine)N–CH$_2$–C$_6$H$_4$–F (4-) |
| 414 | (tricyclic lactam with methyl) | 2 | –N(piperazine)N–CH$_2$–C$_6$H$_4$–Cl (2-) |
| 415 | (tricyclic lactam with methyl) | 2 | –N(piperazine)N–CH$_2$–C$_6$H$_4$–Cl (3-) |

TABLE 34

| No. | Ar | n | Y |
|---|---|---|---|
| 416 | (tricyclic lactam with methyl) | 2 | –N(piperazine)N–CH$_2$–C$_6$H$_4$–Cl (4-) |
| 417 | (tricyclic lactam with methyl) | 2 | –N(piperazine)N–CH$_2$–C$_6$H$_3$–Cl$_2$ (2,3-) |

TABLE 34-continued
| No. | Ar | n | Y |
|---|---|---|---|
| 418 | 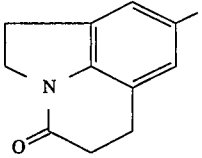 | 2 | 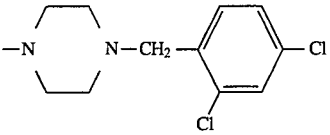 |
| 419 | 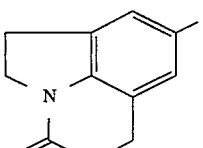 | 2 | 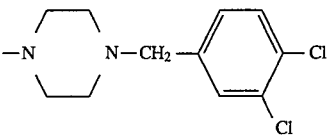 |
| 420 | 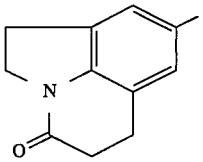 | 2 | 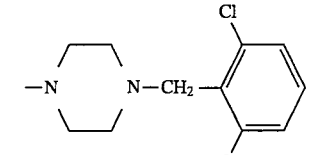 |
| 421 | 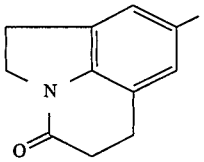 | 2 | 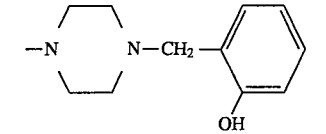 |
| 422 | 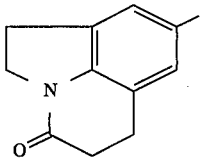 | 2 | 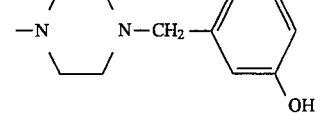 |
| 423 | 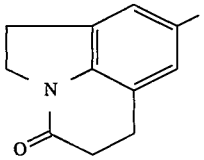 | 2 | 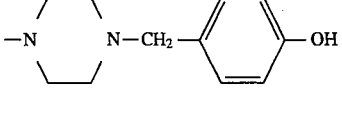 |
| 424 | 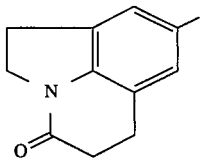 | 2 | 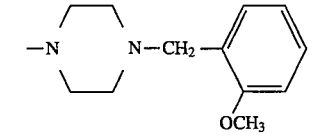 |
| 425 | 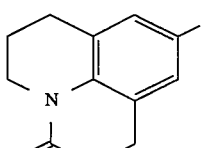 | 2 | 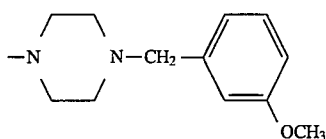 |
| 426 | 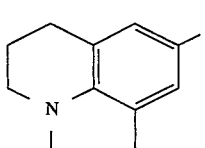 | 2 | 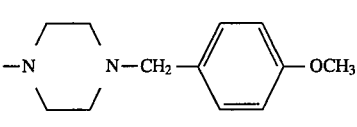 |

TABLE 34-continued

| No. | Ar | n | Y |
| --- | --- | --- | --- |
| 427 | (pyrrolizidinone-fused aromatic) | 2 | −N(piperazine)N−CH₂−(3,4-dimethoxyphenyl) |

TABLE 35

| No. | Ar | n | Y |
| --- | --- | --- | --- |
| 428 | (pyrrolizidinone-fused aromatic) | 2 | −N(piperazine)N−CH₂−(3,4-methylenedioxyphenyl) |
| 429 | (pyrrolizidinone-fused aromatic) | 2 | −N(piperazine)N−CH₂−(2-NO₂-phenyl) |
| 430 | (pyrrolizidinone-fused aromatic) | 2 | −N(piperazine)N−CH₂−(3-NO₂-phenyl) |
| 431 | (pyrrolizidinone-fused aromatic) | 2 | −N(piperazine)N−CH₂−(4-NO₂-phenyl) |
| 432 | (pyrrolizidinone-fused aromatic) | 2 | −N(piperazine)N−CH₂−(2-CN-phenyl) |
| 433 | (pyrrolizidinone-fused aromatic) | 2 | −N(piperazine)N−CH₂−(3-CN-phenyl) |
| 434 | (pyrrolizidinone-fused aromatic) | 2 | −N(piperazine)N−CH₂−(4-CN-phenyl) |

TABLE 35-continued

| No. | Ar | n | Y |
|---|---|---|---|
| 435 | (tricyclic lactam) | 2 | piperazine-CH₂-(2-aminophenyl), NH₂ |
| 436 | (tricyclic lactam) | 2 | piperazine-CH₂-(3-aminophenyl), NH₂ |
| 437 | (tricyclic lactam) | 2 | piperazine-CH₂-(4-aminophenyl), NH₂ |
| 438 | (tricyclic lactam) | 2 | piperazine-CH₂-(2-N(CH₃)₂-phenyl) |
| 439 | (tricyclic lactam) | 2 | piperazine-CH₂-(3-N(CH₃)₂-phenyl) |

TABLE 36

| No. | Ar | n | Y |
|---|---|---|---|
| 440 | (tricyclic lactam) | 2 | piperazine-CH₂-(4-N(CH₃)₂-phenyl) |
| 441 | (tricyclic lactam) | 2 | piperazine-CH₂-(3-piperidinyl-phenyl) |
| 442 | (tricyclic lactam) | 2 | piperazine-CH₂-(2-SCH₃-phenyl) |

TABLE 36-continued

| No. | Ar | n | Y |
|---|---|---|---|
| 443 | (tricyclic lactam) | 2 | piperazine-CH₂-phenyl-3-SCH₃ |
| 444 | (tricyclic lactam) | 2 | piperazine-CH₂-phenyl-4-SCH₃ |
| 445 | (tricyclic lactam) | 2 | piperazine-CH₂-phenyl-4-F, 3-Cl |
| 446 | (tricyclic lactam) | 2 | piperazine-CH₂-phenyl-3-Br |
| 447 | (tricyclic lactam) | 2 | piperazine-CH₂-phenyl-3-CO₂H |
| 448 | (tricyclic lactam) | 2 | piperazine-CH₂-phenyl-3-CO₂CH₃ |
| 449 | (tricyclic lactam) | 2 | piperazine-CH₂-phenyl-3-Ac |
| 450 | (tricyclic lactam) | 2 | piperazine-CH₂-phenyl-3-NHAc |
| 451 | (tricyclic lactam) | 2 | piperidine-CH₂-phenyl-2,3-diCl |

TABLE 37
| No. | Ar | n | Y |
|---|---|---|---|
| 452 | 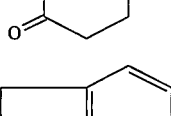 | 2 | 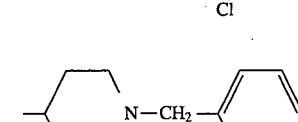 |
| 453 | 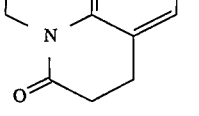 | 2 | 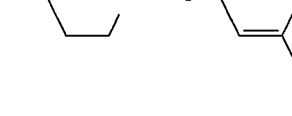 |
| 454 | 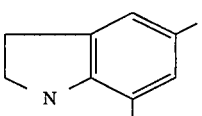 | 2 | 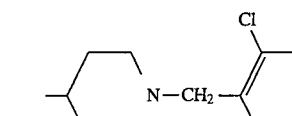 |
| 455 | 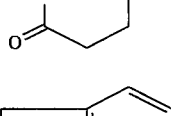 | 2 |  |
| 456 | 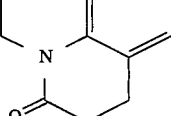 | 2 | 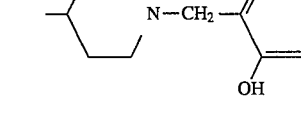 |
| 457 | 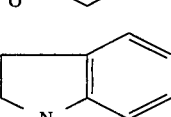 | 2 | 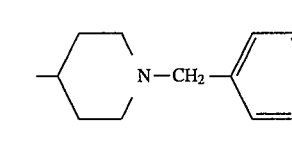 |
| 458 | 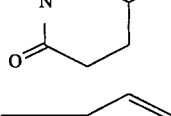 | 2 |  |
| 459 | 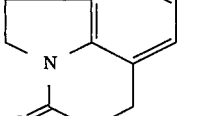 | 2 | 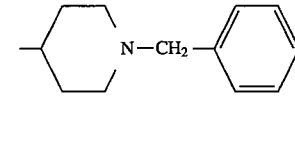 |
| 460 | 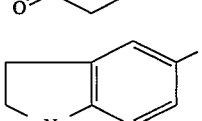 | 2 | 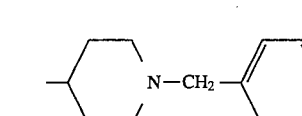 |

TABLE 37-continued

| No. | Ar | n | Y |
|---|---|---|---|
| 461 | (tricyclic lactam) | 2 | piperidine-N-CH$_2$-(3,4-dimethoxyphenyl) |
| 462 | (tricyclic lactam) | 2 | piperidine-N-CH$_2$-(3,4-methylenedioxyphenyl) |
| 463 | (tricyclic lactam) | 2 | piperidine-N-CH$_2$-(2-nitrophenyl) |

TABLE 38

| No. | Ar | n | Y |
|---|---|---|---|
| 464 | (tricyclic lactam) | 2 | piperidine-N-CH$_2$-(3-nitrophenyl) |
| 465 | (tricyclic lactam) | 2 | piperidine-N-CH$_2$-(4-nitrophenyl) |
| 466 | (tricyclic lactam) | 2 | piperidine-N-CH$_2$-(2-cyanophenyl) |
| 467 | (tricyclic lactam) | 2 | piperidine-N-CH$_2$-(3-cyanophenyl) |
| 468 | (tricyclic lactam) | 2 | piperidine-N-CH$_2$-(2-methylphenyl) |

TABLE 38-continued
| No. | Ar | n | Y |
|---|---|---|---|
| 469 | 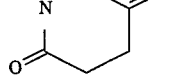 | 2 |  |
| 470 | 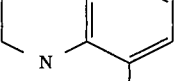 | 2 | 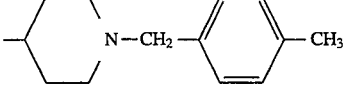 |
| 471 |  | 2 |  |
| 472 | 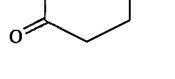 | 2 |  |
| 473 | 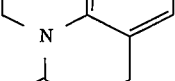 | 2 | 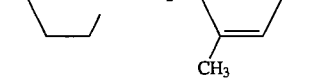 |
| 474 | 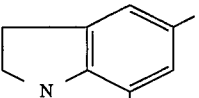 | 2 | 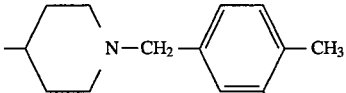 |
| 475 | 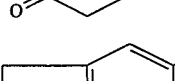 | 2 |  |
TABLE 39
| No. | Ar | n | Y |
|---|---|---|---|
| 476 | | 2 | |

TABLE 39-continued

| No. | Ar | n | Y |
|---|---|---|---|
| 477 | (tricyclic lactam) | 2 | 4-piperidinyl-N-CH₂-(3-Et-phenyl) |
| 478 | (tricyclic lactam) | 2 | 4-piperidinyl-N-CH₂-(4-Et-phenyl) |
| 479 | (tricyclic lactam) | 2 | 4-piperidinyl-N-CH₂-(2-F-phenyl) |
| 480 | (tricyclic lactam) | 2 | 4-piperidinyl-N-CH₂-(3-F-phenyl) |
| 481 | (tricyclic lactam) | 2 | 4-piperidinyl-N-CH₂-(4-F-phenyl) |
| 482 | (tricyclic lactam) | 2 | 4-piperidinyl-N-CH₂-(2-Cl-phenyl) |
| 483 | (tricyclic lactam) | 2 | 4-piperidinyl-N-CH₂-(3-Cl-phenyl) |
| 484 | (tricyclic lactam) | 2 | 4-piperidinyl-N-CH₂-(4-Cl-phenyl) |
| 485 | (tricyclic lactam) | 2 | 4-piperidinyl-N-CH₂-(4-CN-phenyl) |

TABLE 39-continued
| No. | Ar | n | Y |
|---|---|---|---|
| 486 | 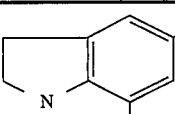 | 2 | 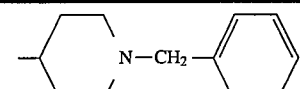 |
| 487 | 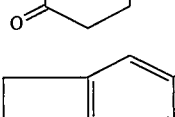 | 2 | 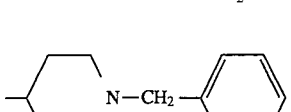 |
TABLE 40
| No. | Ar | n | Y |
|---|---|---|---|
| 488 | 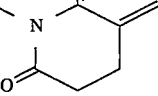 | 2 | 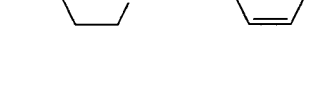 |
| 489 | 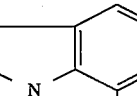 | 2 | 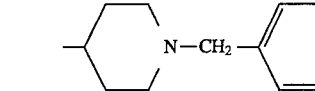 |
| 490 | 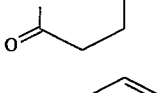 | 2 | 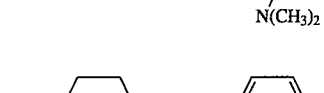 |
| 491 | 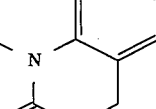 | 2 | 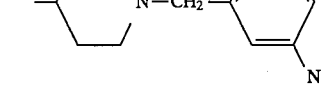 |
| 492 | 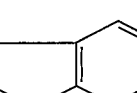 | 2 | 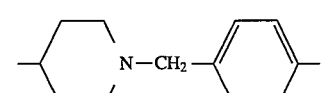 |
| 493 | 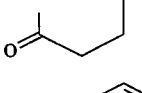 | 2 | 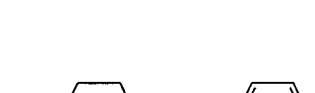 |

TABLE 40-continued

| No. | Ar | n | Y |
|---|---|---|---|
| 494 | (tricyclic lactam) | 2 | piperidine-N-CH₂-(3-SCH₃-phenyl) |
| 495 | (tricyclic lactam) | 2 | piperidine-N-CH₂-(4-SCH₃-phenyl) |
| 496 | (tricyclic lactam) | 2 | piperidine-N-CH₂-(3-Cl, 4-F-phenyl) |
| 497 | (tricyclic lactam) | 2 | piperidine-N-CH₂-(3-Br-phenyl) |
| 498 | (tricyclic lactam) | 2 | piperidine-N-CH₂-(3-CO₂H-phenyl) |
| 499 | (tricyclic lactam) | 2 | piperidine-N-CH₂-(3-CO₂CH₃-phenyl) |

TABLE 41

| No. | Ar | n | Y |
|---|---|---|---|
| 500 | (tricyclic lactam) | 2 | piperidine-N-CH₂-(3-Ac-phenyl) |
| 501 | (tricyclic lactam) | 2 | piperidine-N-CH₂-(3-NHAc-phenyl) |

TABLE 41-continued
| No. | Ar | n | Y |
|---|---|---|---|
| 502 | 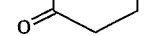 | 2 |  |
| 503 |  | 2 | 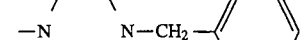 |
| 504 |  | 2 |  |
| 505 |  | 2 |  |
| 506 | 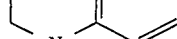 | 2 | 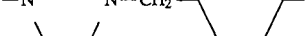 |
| 507 | 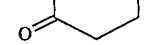 | 2 |  |
| 508 | 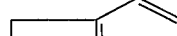 | 2 |  |
| 509 |  | 2 | 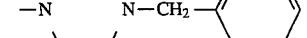 |
| 510 | 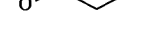 | 2 |  |

TABLE 41-continued

| No. | Ar | n | Y |
|-----|----|----|---|
| 511 | (2,3-dihydro-1H,5H-pyrrolo[3,2,1-ij]quinolin-6(4H)-one, substituted) | 2 | −N(piperazine)N−CH$_2$−(3-Et-phenyl) |

TABLE 42

| No. | Ar | n | Y |
|-----|----|----|---|
| 512 | (2,3-dihydro-1H,5H-pyrrolo[3,2,1-ij]quinolin-6(4H)-one) | 2 | −N(piperazine)N−CH$_2$−(4-Et-phenyl) |
| 513 | (2,3-dihydro-1H,5H-pyrrolo[3,2,1-ij]quinolin-6(4H)-one) | 2 | −N(piperazine)N−CH$_2$−(2-F-phenyl) |
| 514 | (2,3-dihydro-1H,5H-pyrrolo[3,2,1-ij]quinolin-6(4H)-one) | 2 | −N(piperazine)N−CH$_2$−(3-F-phenyl) |
| 515 | (2,3-dihydro-1H,5H-pyrrolo[3,2,1-ij]quinolin-6(4H)-one) | 2 | −N(piperazine)N−CH$_2$−(4-F-phenyl) |
| 516 | (2,3-dihydro-1H,5H-pyrrolo[3,2,1-ij]quinolin-6(4H)-one) | 2 | −N(piperazine)N−CH$_2$−(2-Cl-phenyl) |
| 517 | (2,3-dihydro-1H,5H-pyrrolo[3,2,1-ij]quinolin-6(4H)-one) | 2 | −N(piperazine)N−CH$_2$−(3-Cl-phenyl) |
| 518 | (2,3-dihydro-1H,5H-pyrrolo[3,2,1-ij]quinolin-6(4H)-one) | 2 | −N(piperazine)N−CH$_2$−(4-Cl-phenyl) |

TABLE 42-continued

| No. | Ar | n | Y |
|---|---|---|---|
| 519 | (tricyclic lactam) | 2 | −N(piperazine)N−CH$_2$−(2-methylphenyl) |
| 520 | (tricyclic lactam) | 2 | −N(piperazine)N−CH$_2$−(3-methylphenyl) |
| 521 | (tricyclic lactam) | 2 | −N(piperazine)N−CH$_2$−(4-methylphenyl) |
| 522 | (tricyclic lactam) | 2 | −N(piperazine)N−CH$_2$−(2,5-dimethylphenyl) |
| 523 | (tricyclic lactam) | 2 | −N(piperazine)N−CH$_2$−(2,4-dimethylphenyl) |

TABLE 43

| No. | Ar | n | Y |
|---|---|---|---|
| 524 | (tricyclic lactam) | 2 | −N(piperazine)N−CH$_2$−(3,4-dimethylphenyl) |
| 525 | (tricyclic lactam) | 2 | −N(piperazine)N−CH$_2$−(2,6-dimethylphenyl) |
| 526 | (tricyclic lactam) | 2 | −N(piperazine)N−CH$_2$−(indanyl) |

TABLE 43-continued
| No. | Ar | n | Y |
|---|---|---|---|
| 527 | 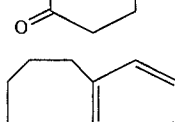 | 2 | 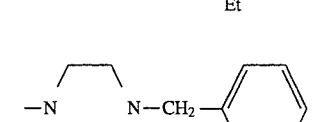 |
| 528 | 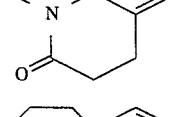 | 2 | 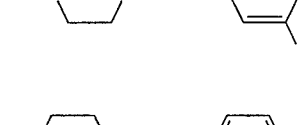 |
| 529 | 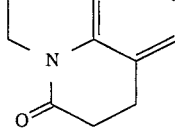 | 2 | 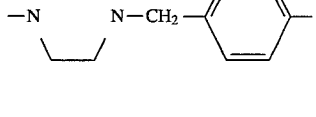 |
| 530 | 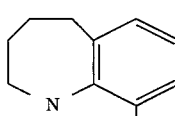 | 2 | 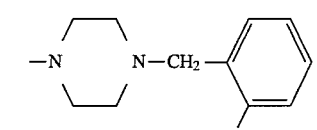 |
| 531 | 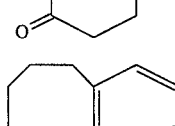 | 2 | 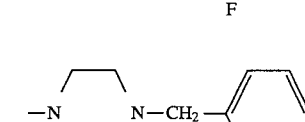 |
| 532 | 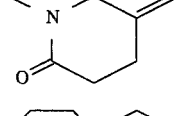 | 2 |  |
| 533 | 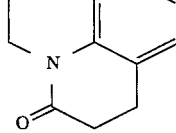 | 2 | 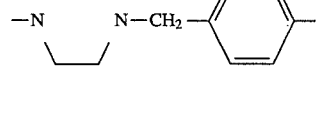 |
| 534 | 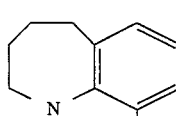 | 2 | 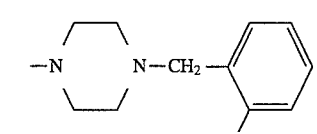 |
| 535 | 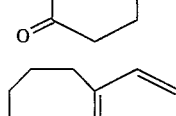 | 2 | 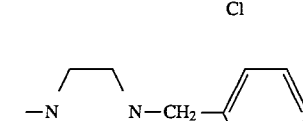 |

TABLE 44

| No. | Ar | n | Y |
|---|---|---|---|
| 536 | (tricyclic lactam) | 2 | piperazine-CH₂-(2-methylphenyl) |
| 537 | (tricyclic lactam) | 2 | piperazine-CH₂-(3-methylphenyl) |
| 538 | (tricyclic lactam) | 2 | piperazine-CH₂-(4-methylphenyl) |
| 539 | (tricyclic lactam) | 2 | piperazine-CH₂-(2,5-dimethylphenyl) |
| 540 | (tricyclic lactam) | 2 | piperazine-CH₂-(2,4-dimethylphenyl) |
| 541 | (tricyclic lactam) | 2 | piperazine-CH₂-(3,4-dimethylphenyl) |
| 542 | (tricyclic lactam) | 2 | piperazine-CH₂-(2,6-dimethylphenyl) |
| 543 | (tricyclic lactam) | 2 | piperazine-CH₂-(indanyl) |
| 544 | (tricyclic lactam) | 2 | piperazine-CH₂-(2-ethylphenyl) |

TABLE 44-continued

| No. | Ar | n | Y |
|---|---|---|---|
| 545 | (tricyclic lactam) | 2 | piperazine-N-CH₂-(3-Et-phenyl) |
| 546 | (tricyclic lactam) | 2 | piperazine-N-CH₂-(4-Et-phenyl) |
| 547 | (tricyclic lactam) | 2 | piperazine-N-CH₂-(2-F-phenyl) |

TABLE 45

| No. | Ar | n | Y |
|---|---|---|---|
| 548 | (tricyclic lactam) | 2 | piperazine-N-CH₂-(3-F-phenyl) |
| 549 | (tricyclic lactam) | 2 | piperazine-N-CH₂-(4-F-phenyl) |
| 550 | (tricyclic lactam) | 2 | piperazine-N-CH₂-(2-Cl-phenyl) |
| 551 | (tricyclic lactam) | 2 | piperazine-N-CH₂-(3-Cl-phenyl) |
| 552 | (tricyclic lactam) | 2 | piperazine-N-CH₂-(4-Cl-phenyl) |

TABLE 45-continued

| No. | Ar | n | Y |
|---|---|---|---|
| 553 | (tricyclic lactam) | 2 | piperidine-N-CH₂-(2-methylphenyl) |
| 554 | (tricyclic lactam) | 2 | piperidine-N-CH₂-(3-methylphenyl) |
| 555 | (tricyclic lactam) | 2 | piperidine-N-CH₂-(4-methylphenyl) |
| 556 | (tricyclic lactam) | 2 | piperidine-N-CH₂-(2,5-dimethylphenyl) |
| 557 | (tricyclic lactam) | 2 | piperidine-N-CH₂-(2,4-dimethylphenyl) |
| 558 | (tricyclic lactam) | 2 | piperidine-N-CH₂-(3,4-dimethylphenyl) |
| 559 | (tricyclic lactam) | 2 | piperidine-N-CH₂-(2,6-dimethylphenyl) |

TABLE 46

| No. | Ar | n | Y |
|---|---|---|---|
| 560 | (tricyclic lactam) | 2 | piperidine-N-CH₂-(indanyl) |

TABLE 46-continued
| No. | Ar | n | Y |
|---|---|---|---|
| 561 | 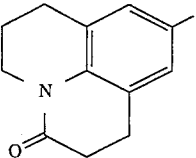 | 2 | 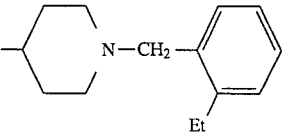 |
| 562 | 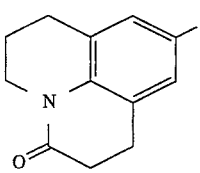 | 2 | 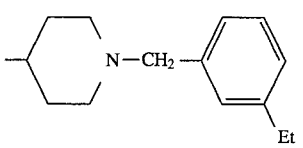 |
| 563 | 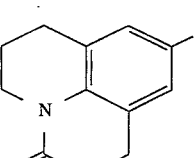 | 2 | 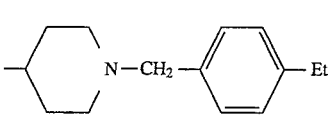 |
| 564 | 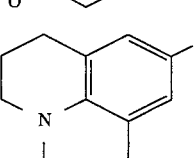 | 2 | 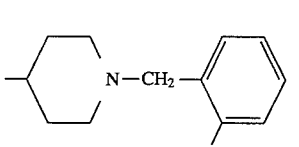 |
| 565 | 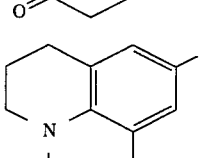 | 2 | 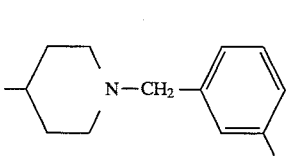 |
| 566 | 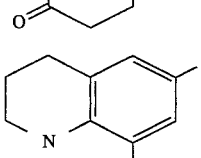 | 2 | 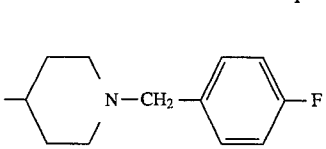 |
| 567 | 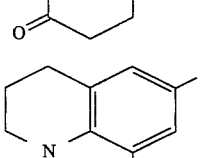 | 2 | 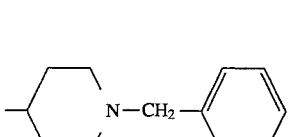 |
| 568 | 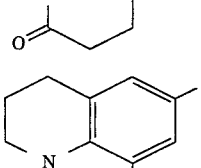 | 2 | 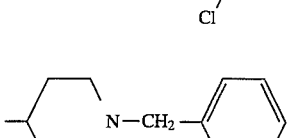 |
| 569 | 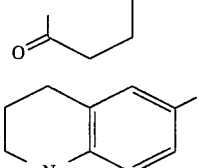 | 2 | 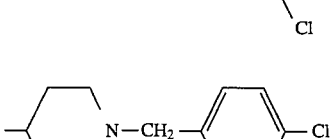 |

TABLE 46-continued

| No. | Ar | n | Y |
|---|---|---|---|
| 570 | (fused bicyclic with N, C=O) | 2 | piperidine-N-CH₂-(2-methylphenyl) |
| 571 | (fused bicyclic with N, C=O) | 2 | piperidine-N-CH₂-(3-methylphenyl) |

TABLE 47

| No. | Ar | n | Y |
|---|---|---|---|
| 572 | (fused bicyclic with N, C=O) | 2 | piperidine-N-CH₂-(4-methylphenyl) |
| 573 | (fused bicyclic with N, C=O) | 2 | piperidine-N-CH₂-(2,5-dimethylphenyl) |
| 574 | (fused bicyclic with N, C=O) | 2 | piperidine-N-CH₂-(2,4-dimethylphenyl) |
| 575 | (fused bicyclic with N, C=O) | 2 | piperidine-N-CH₂-(3,4-dimethylphenyl) |
| 576 | (fused bicyclic with N, C=O) | 2 | piperidine-N-CH₂-(2,6-dimethylphenyl) |
| 577 | (fused bicyclic with N, C=O) | 2 | piperidine-N-CH₂-(indanyl) |

TABLE 47-continued

| No. | Ar | n | Y |
|---|---|---|---|
| 578 | [benzazepinone] | 2 | piperidine-N-CH₂-(2-Et-phenyl) |
| 579 | [benzazepinone] | 2 | piperidine-N-CH₂-(3-Et-phenyl) |
| 580 | [benzazepinone] | 2 | piperidine-N-CH₂-(4-Et-phenyl) |
| 581 | [benzazepinone] | 2 | piperidine-N-CH₂-(2-F-phenyl) |
| 582 | [benzazepinone] | 2 | piperidine-N-CH₂-(3-F-phenyl) |
| 583 | [benzazepinone] | 2 | piperidine-N-CH₂-(4-F-phenyl) |

TABLE 48

| No. | Ar | n | Y |
|---|---|---|---|
| 584 | [benzazepinone] | 2 | piperidine-N-CH₂-(2-Cl-phenyl) |
| 585 | [benzazepinone] | 2 | piperidine-N-CH₂-(3-Cl-phenyl) |

TABLE 48-continued
| No. | Ar | n | Y |
|---|---|---|---|
| 586 | 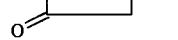 | 2 |  |
| 587 |  | 2 |  |
| 588 | 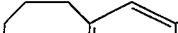 | 2 |  |
| 589 | 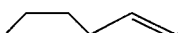 | 2 |  |
| 590 |  | 2 |  |
| 591 |  | 2 |  |
| 592 | 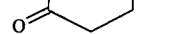 | 2 |  |
| 593 |  | 2 |  |
| 594 |  | 2 |  |

TABLE 48-continued

| No. | Ar | n | Y |
|---|---|---|---|
| 595 | (tricyclic lactam) | 2 | piperidine-N-CH2-(2-Et-phenyl) |

TABLE 49

| No. | Ar | n | Y |
|---|---|---|---|
| 596 | (tricyclic lactam) | 2 | piperidine-N-CH2-(3-Et-phenyl) |
| 597 | (tricyclic lactam) | 2 | piperidine-N-CH2-(4-Et-phenyl) |
| 598 | (tricyclic lactam) | 2 | piperidine-N-CH2-(2-F-phenyl) |
| 599 | (tricyclic lactam) | 2 | piperidine-N-CH2-(3-F-phenyl) |
| 600 | (tricyclic lactam) | 2 | piperidine-N-CH2-(4-F-phenyl) |
| 601 | (tricyclic lactam) | 2 | piperidine-N-CH2-(2-Cl-phenyl) |
| 602 | (tricyclic lactam) | 2 | piperidine-N-CH2-(3-Cl-phenyl) |

TABLE 49-continued
| No. | Ar | n | Y |
|---|---|---|---|
| 603 | 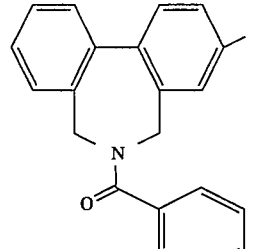 | 2 | 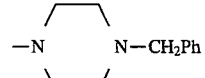 |
| 604 | 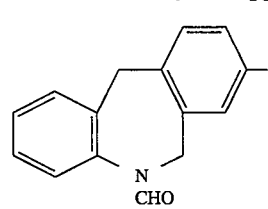 | 2 | —N⟨piperazine⟩N—CH₂Ph |
| 605 | (biphenyl-N-CH₂-C₆H₄-OCH₃) | 2 | —N⟨piperazine⟩N—CH₂Ph |
| 606 | (biphenyl-N-C(O)Ph) | 2 | —N⟨piperazine⟩N—CH₂Ph |
TABLE 50
| No. | Ar | n | Y |
|---|---|---|---|
| 607 | 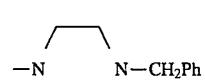 | 2 | —N⟨piperazine⟩N—CH₂Ph |
| 608 | (dibenzazepine-N-CHO) | 2 | —N⟨piperazine⟩N—CH₂Ph |

TABLE 50-continued

| No. | Ar | n | Y |
|---|---|---|---|
| 609 | (dibenzazepine-CH₂NH) | 2 | —N(piperazine)N—CH₂Ph |
| 610 | (dibenzazepine-CH₂NH) | 2 | —(piperidine)N—CH₂Ph |
| 611 | (phenoxy-aniline-CHO) | 2 | —N(piperazine)N—CH₂Ph |
| 612 | (phenoxy-aniline-NH) | 2 | —N(piperazine)N—CH₂Ph |
| 613 | (phenoxy-aniline-NH) | 2 | —(piperidine)N—CH₂Ph |
| 614 | (tetrahydronaphthalene-CH₂NH, H wedge) | 2 | —(piperidine)N—CH₂Ph |
| 615 | (tetrahydronaphthalene-CH₂NH, H dash) | 2 | —(piperidine)N—CH₂Ph |

TABLE 51

| No. | Ar | n | Y |
|---|---|---|---|
| 616 | (perimidine-type bicyclic aromatic with HN-CH2 bridge) | 2 | -N(piperazine)N-CH2Ph |
| 617 | (perimidine-type bicyclic aromatic with HN-CH2 bridge) | 2 | -(piperidin-4-yl)-N-CH2Ph |
| 618 | (perimidine-type bicyclic aromatic with N-CH2Ph bridge) | 2 | -(piperidin-4-yl)-N-CH2Ph |
| 619 | 2,3,4,4a,9,9a-hexahydro-1H-carbazole (NH) | 2 | -N(piperazine)N-CH2Ph |
| 620 | 2,3,4,4a,9,9a-hexahydro-1H-carbazole (NH) | 2 | -(piperidin-4-yl)-N-CH2Ph |
| 621 | 2,3,4,4a,9,9a-hexahydro-1H-carbazole (N-benzyl) | 2 | -(piperidin-4-yl)-N-CH2Ph |
| 622 | dibenzazepine-type (N-CHO) | 2 | -N(piperazine)N-CH2Ph |
| 623 | dibenzazepine-type (NH) | 2 | -N(piperazine)N-CH2Ph |
| 624 | dibenzazepine-type (NH) | 2 | -(piperidin-4-yl)-N-CH2Ph |
| 625 | dibenzazepine-type (N-CH3) | 2 | -(piperidin-4-yl)-N-CH2Ph |

TABLE 51-continued

| No. | Ar | n | Y |
|---|---|---|---|
| 626 |  | 2 | 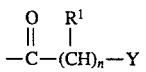 |

In the above tables, Ac represents an acetyl group; Et represents an ethyl group; Ph represents a phenyl group.

It is preferable that salts of the compound (I') be physiologically acceptable acid adduct salts. Such salts include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

When having an acidic group such as —COOH, the compound (I') may form a salt with an inorganic base (e.g., sodium, potassium, calcium, magnesium, ammonia) or an organic base (e.g., triethylamine). Such salts are also included in the scope of the present invention.

A method of producing the compound (I') or a salt thereof is hereinafter described in detail.

Although the following description of the production process is applicable not only to the compound (I') itself but also to the above-described salt thereof, the salt is also referred to as the compound (I') in the description below.

The compound (I') can be produced by reacting a compound represented by the formula:

$$\text{Ar—H} \qquad (II)$$

wherein the symbols have the same definitions as above or a salt thereof, and a compound (or salt thereof) represented by the formula:

wherein $Z^1$ represents a leaving group; the other symbols have the same definitions as above or a salt thereof.

The leaving group for $Z^1$ is exemplified by halogen atoms (e.g., chlorine, bromine and iodine), $C_{1-6}$ alkylsulfonyloxy groups (e.g., methanesulfonyloxy, ethanesulfonyloxy) and $C_{6-10}$ arylsulfonyloxy groups (e.g., benzenesulfonyloxy, p-toluenesulfonyloxy), with preference given to halogen atoms (e.g., chlorine) and others.

The compound (II) or a salt thereof can be produced by known methods or modifications thereof such as the methods described in the Journal of Chemical Society, 1381 (1949), the Canadian Journal of Chemistry, 42, 2904 (1964), the Journal of Organic Chemistry, 28, 3058 (1963), the Journal of American Chemical Society, 76, 3194 (1954), 87, 1397 (1965), 88, 4061 (1966) and Japanese Patent Unexamined Publication No. 41539/1974.

The compound (III) or a salt thereof can be produced by known methods or modifications thereof such as the methods described in the Chemical Pharmaceutical Bulletin, 34, 3747–3761 (1986) and EP-A-0,378,207.

Salts of the compounds (II) and (III) include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). When having an acidic group such as —COOH, the compounds (II) and (III) may form a salt with an inorganic base (e.g., alkali metal or alkaline earth metal such as sodium, potassium, calcium or magnesium, or ammonia) or an organic base (e.g., tri-$C_{1-3}$ alkylamine such as triethylamine).

The reaction between the compound (III) or a salt thereof and the compound (II) or a salt thereof can be carried out by, for example, reacting them in the absence of a solvent or in a solvent as necessary. Any solvent for ordinary chemical represents can be used for this reaction, as long as the reaction is not interfered with. Such solvents include organic solvents such as hydrocarbon solvents (e.g., pentane, hexane, benzene, toluene, nitrobenzene), halogenated hydrocarbon solvents (e.g., dichloromethane, chloroform, 1,2-dichloroethane, carbon tetrachloride), ether solvents (e.g., ethyl ether, tetrahydrofuran, dioxane, dimethoxyethane), nitroalkanes (e.g., nitromethane, propionitrile), and carbon disulfide, with preference given to dichloromethane, 1,2-dichloroethane, nitrobenzene, carbon disulfide and others. The amount of solvent used is normally 0.5 to 100 ml, preferably 5 to 20 ml per mmol of the compound (III) or a salt thereof. Reaction temperature is normally about −30° to 150° C., preferably about 20° to 100° C. Reaction time is normally 0.5 to 72 hours, preferably 1 to 16 hours.

Lewis acids for this reaction include aluminum chloride, aluminum bromide, zinc chloride, titanium chloride, tin (IV) chloride, boron trifluoride, iron (II) chloride, iron (III) chloride, antimony (V) pentachloride, bismuth (III) chloride, mercury (II) chloride, hydrogen fluoride, sulfuric acid and polyphosphoric acid, with preference given to aluminum chloride and others. The amount of Lewis acid used is normally 1 to 10 mol, preferably 2 to 10 mol per mol of the compound (III) or a salt thereof. The amount of the compound (II) or a salt thereof used is normally about 1 to 20 mol, preferably about 1 to 5 mol per mol of the compound (III) or a salt thereof.

In the above reaction, the position at which the following group:

$$\underset{\phantom{X}}{\overset{O}{\|}}\,\underset{\phantom{X}}{\overset{R^1}{|}}$$
$$-C-(CH)_n-Y$$

in the compound (III) or a salt thereof is introduced to the compound (II) or a salt thereof may be any one of the possible positions of substitution in ring A. However, when the compound (II) or a salt thereof has a 1,2,2a,3,4,5-hexahydrobenz[cd]indole skeleton (provided that ring A has no substituent), it is introduced mainly at the 6-position.

However, compounds having an introduction at other positions (7- and 8-positions) may be produced and separated.

Also, by reacting a compound represented by the formula:

$$Ar-\overset{O}{\overset{\|}{C}}-(CH)_n-\overset{R^1}{\overset{|}{}}-Z^2 \qquad (IV)$$

wherein the symbols have the same definitions as above or a salt thereof, and a compound represented by the formula:

$$Z^3-Y'' \qquad (V)$$

wherein the symbols have the same definitions as above or a salt thereof, a compound represented by the formula:

$$Ar-\overset{O}{\overset{\|}{C}}-(CH)_n-\overset{R^1}{\overset{|}{}}-Y'' \qquad (VI)$$

wherein the symbols have the same definitions as above or a salt thereof, can be produced.

$Z^2$ and $Z^3$ independently represent a group capable of splitting off upon reaction therebetween.

The leaving group for $Z^2$ is exemplified by halogen atoms (e.g., chlorine, bromine and iodine), $C_{1-6}$ alkylsulfonyloxy groups (e.g., methanesulfonyloxy, ethanesulfonyloxy) and $C_{6-10}$ arylsulfonyloxy groups (e.g., benzenesulfonyloxy, p-toluenesulfonyloxy), with preference given to halogen atoms. More specifically, $Z^2$ is preferably a halogen atom such as an atom of chlorine or bromine.

The leaving group for $Z^3$ is exemplified by hydrogen atom, trialkylsilyl groups (e.g., trimethylsilyl, triethylsilyl, t-butyldimethylsilyl) and metal atoms (e.g., atoms of sodium, potassium and lithium). A hydrogen atom, in particular, is often used.

Salts of the compound (VI) are exemplified by the same salts as specified for the compound (I').

Salts of the compounds (IV) and (V) include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). When having an acidic group such as —COOH, the compounds (IV) and (V) may form a salt with an inorganic base (e.g., alkali metal or alkaline earth metal such as sodium, potassium, calcium or magnesium, or ammonia) or an organic base (e.g., tri-$C_{1-3}$ alkylamine such as triethylamine).

The amount of the compound (V) or a salt thereof used for this reaction is normally 1.0 to 50.0 mol, preferably 1.0 to 10.0 mol per mol of the compound (IV) or a salt thereof. This reaction can be carried out under cooling or heating conditions (0° to 120° C.). Reaction time is normally 10 minutes to 48 hours, preferably 2 to 16 hours.

Although this reaction can be carried out in the absence of a solvent, it may be carried out in a solvent as necessary. Any solvent can be used for this reaction, as long as the reaction is not interfered with. Such solvents include lower alcohols such as methanol, ethanol, propanol, isopropanol, n-butanol and t-butanol, ethers such as dioxane, ether and tetrahydrofuran, aromatic hydrocarbons such as toluene, benzene and xylene, halogenated hydrocarbons such as dichloromethane, 1,2-dichloroethane, amides such as dimethylformamide, dimethylacetamide and hexamethylphosphonotriamide, and esters such as ethyl acetate and butyl acetate. The amount of solvent used is normally 0.5 to 100 ml, preferably 5 to 20 ml per mmol of the compound (IV-a) or a salt thereof.

This reaction can be carried out in the presence of a base as necessary. Bases for this purpose include inorganic bases such as sodium carbonate, potassium carbonate, lithium carbonate, sodium hydroxide, potassium hydroxide, sodium methoxide, sodium ethoxide and sodium hydride, and organic bases such as pyridine, 4-dimethylaminopyridine and triethylamine. The amount of base used is normally 1 mol or more, preferably 1.0 to 5.0 mol per mol of the compound (V) or a salt thereof.

Also, this reaction may be accelerated as appropriate in the presence of an iodide (e.g., sodium iodide, potassium iodide, lithium iodide). In this case, the amount of iodide used is normally 1 to 5 mol, preferably 1.0 to 1.5 mol per mol of the compound (IV) or a salt thereof.

The starting material compound (IV) or a salt thereof can be produced by, for example, reacting a compound represented by the formula:

$$Ar-H \qquad (II)$$

wherein the symbols have the same definitions as above or a salt thereof, and a compound represented by the formula:

$$Z^4-\overset{O}{\overset{\|}{C}}-(CH)_n-\overset{R^1}{\overset{|}{}}-Z^2 \qquad (VIII)$$

wherein $Z^4$ represents a leaving group; the other symbols have the same definitions as above or a salt thereof.

The leaving group for $Z^4$ is exemplified by halogen atoms (e.g., atoms of chlorine, bromine and iodine), $C_{1-6}$ alkylsulfonyloxy groups (e.g., methanesulfonyloxy, ethanesulfonyloxy) and $C_{6-10}$ arylsulfonyloxy groups (e.g., benzenesulfonyloxy, p-toluenesulfonyloxy), with preference given to halogen atoms (e.g., chlorine atom) etc.

The compound (VIII) can be produced by known methods or modifications thereof.

The reaction between the compound (II) or a salt thereof and the compound (VIII) or a salt thereof can be carried out under, for example, the same conditions as for the reaction between the compound (II) or a salt thereof and the compound (III) or a salt thereof.

In the above reaction, the position at which the following group:

$$-\overset{O}{\overset{\|}{C}}-(CH)_n-\overset{R^1}{\overset{|}{}}-Z^2$$

in the compound (VIII) is introduced to the compound (II) or a salt thereof may be any one of the possible positions of substitution in ring A. However, when the compound (II) or a salt thereof has a 1,2,2a,3,4,5-hexahydrobenz[cd]indole skeleton (provided that ring A has no substituent), it is introduced mainly at the 6-position. However, compounds having an introduction at other positions (7- and 8-positions) may be produced and separated.

The compound (IV) or a salt thereof thus obtained may be isolated and purified by known means such as concentration, liquid property conversion, redissolution, solvent extraction, fractional distillation, distillation, crystallization, recrystallization and chromatography, or may be used in the form of a reaction mixture as such, without isolation, as a starting material for the next process.

The starting material compound (V) or a salt thereof can be produced by known methods or modifications thereof.

Also, the compound (I') wherein n is 2 and Y is a 1-piperazinyl group or 4-benzyl-1-piperidinyl group, i.e., a compound or a salt thereof represented by the formula:

$$Ar-\overset{O}{\overset{\|}{C}}-\overset{R^4}{\overset{|}{CH}}-\overset{R^5}{\overset{|}{CH}}-Y'' \qquad (IX)$$

wherein $R^4$ and $R^5$ independently represent a hydrogen atom or an optionally substituted hydrocarbon group; the symbols have the same definitions as above, can be produced by, for example, reacting a compound represented by the formula:

$$Ar-\overset{O}{\underset{\|}{C}}-(CH_2)-R^4 \quad (X)$$

wherein the symbols have the same definitions as above or a salt thereof, a compound represented by the formula:

$$R^5-CHO \quad (XI)$$

wherein $R^5$ has the same definition as above, and a compound represented by the formula:

$$Z^3-Y'' \quad (V)$$

wherein the symbols have the same definitions as above.

The optionally substituted hydrocarbon group for $R^4$ or $R^5$ is exemplified by the same optionally substituted hydrocarbon groups which may have a substituent as specified for $R^1$ above.

Salts of compound (IX) may be the same salts as specified for the compound (I').

Salts of compound (X) include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). When having an acidic group such as —COOH, the compound (X) may form a salt with an inorganic base (e.g., alkali metal or alkaline earth metal such as sodium, potassium, calcium or magnesium, or ammonia) or an organic base (e.g., tri-$C_{1-3}$ alkylamine such as triethylamine).

This reaction can, for example, be carried out in the same manner as the procedure for the Mannich reaction described in Organic Reaction, Vol. 1, pp. 303–341, and other publications. Specifically, the desired product can be produced by reacting the compound (XI) and the compound (V) or a salt thereof with the compound (X) or a salt thereof in a molar ratio of normally 0.9 to 10 mol, preferably 1.0 to 3.0 mol of the former per mol of the latter. Although this reaction can be normally carried out at room temperature or under heating conditions (10° to 150° C.), it is preferable to carry out the reaction at 80° to 120° C. Reaction time is normally 1 to 48 hours, preferably 2 to 24 hours. Although this reaction is normally carried out in the absence of a solvent, it may be carried out in a solvent as necessary. Any ordinary solvent for the Mannich reaction can be used for this reaction, as long as the reaction is not interfered with. Such solvents include alcohol solvents such as ethanol. The amount of solvent used is normally 0.5 to 200 ml, preferably 5 to 40 ml per mmol of the compound (X) or a salt thereof. This reaction can be carried out in the presence of an inorganic acid such as hydrochloric acid as necessary. The amount of such acid used is normally catalytic for the compound (IV) or a salt thereof (0.001 to 0.05 mol per mol of the compound (X)). However, when the compound (V) or (X) for the reaction has not formed a salt, it is preferable to use acid in an amount exceeding the minimum amount required for these compounds to form a salt.

The compound (X) or a salt thereof can be produced by reacting the compound (II) or a salt thereof with a compound represented by the formula:

$$Z^5-CO-CH_2-R^4 \quad (XII)$$

wherein $R^5$ represents a leaving group; the other symbols have the same definitions as above. This reaction can be carried out under, for example, the same conditions as for the above-described reaction between the compound (II) or a salt thereof and the compound (VIII).

The compound (XI) can be produced by known methods or modifications thereof.

With respect to the above reactions, provided that the starting material compound has an amino group, a carboxyl group, a hydroxyl group or another group as a substituent therefor, such substituent may have a protecting group in common use in peptide chemistry etc. as introduced therein. The desired compound can be obtained by removing the protecting group as necessary upon completion of the reaction.

Protecting groups for the amino group include $C_{1-6}$ alkyl-carbonyl groups which may have a substituent (e.g., formyl, acetyl, ethylcarbonyl), benzoyl, $C_{1-6}$ alkyl-oxycarbonyl groups (e.g., methoxycarbonyl, ethoxycarbonyl), phenyloxycarbonyl groups (e.g., phenoxycarbonyl), $C_{7-15}$ aralkyloxy-carbonyl groups (e.g., benzyloxycarbonyl, fluorenyloxycarbonyl), trityl and phthaloyl. Substituents for these protecting groups include halogen atoms (e.g., fluorine, chlorine, bromine and iodine), $C_{1-6}$ alkyl-carbonyl groups (e.g., methylcarbonyl, ethylcarbonyl, butylcarbonyl) and nitro group, the number of substituents being about 1 to 3. Protecting groups for the carboxyl group include $C_{1-6}$ alkyl groups which may have a substituent (e.g., methyl, ethyl, n-propyl, isopropyl, n-butyl, tert-butyl), phenyl, trityl and silyl. Substituents for these protecting groups include halogen atoms (e.g., fluorine, chlorine, bromine and iodine), $C_{1-6}$ alkyl-carbonyl groups (e.g., formyl, methylcarbonyl, ethylcarbonyl, butylcarbonyl) and nitro group, the number of substituents being about 1 to 3.

Protecting groups for the hydroxyl group include $C_{1-6}$ alkyl groups which may have a substituent (e.g., methyl, ethyl, n-propyl, isopropyl, n-butyl, tert-butyl), phenyl, $C_{7-10}$ aralkyl groups (e.g., benzyl), $C_{1-6}$ alkylcarbonyl groups (e.g., formyl, acetyl, ethylcarbonyl), phenyloxycarbonyl groups (e.g., phenoxycarbonyl), $C_{7-10}$ aralkyl-carbonyl groups (e.g., benzyloxycarbonyl), pyranyl, furanyl and silyl. Substituents for these protecting groups include halogen atoms (e.g., fluorine, chlorine, bromine and iodine), $C_{1-6}$ alkyl groups, phenyl, $C_{7-10}$ aralkyl groups and nitro group, the number of substituents being about 1 to 4.

These protecting groups can be removed by known methods or modifications thereof, including treatments with acid, base, reducing agents, ultraviolet rays, hydrazine, phenylhydrazine, sodium N-methyldithiocarbamate, tetrabutylammonium fluoride and palladium acetate.

When the compound (I'), (VI) or (IX) or a salt thereof thus obtained has an acylamino group which may have a substituent, it can be converted to a compound or a salt thereof having a primary or secondary amino group by deacylation. The starting material compound (I'), (VI) or (IX) or a salt thereof having an acylamino group which may have a substituent may be as isolated and purified by known means such as concentration, liquid property conversion, redissolution, solvent extraction, fractional distillation, distillation, crystallization, recrystallization and chromatography, or may be used in the form of a reaction mixture as such, without isolation, as a starting material. Accordingly, the compound (I'), (VI) or (IX) or a salt thereof having an acylamino group which may have a substituent is kept at a temperature of normally 10° to 150° C., preferably 50° to 100° C., in an aqueous solution of an acid such as a mineral acid (e.g., nitric acid, hydrochloric acid, hydrobromic acid, iodic acid, sulfuric acid) or a base such as an alkali metal hydroxide (e.g., sodium hydroxide, potassium hydroxide, barium hydroxide, lithium hydroxide). The amount of such acid or base used is normally 1 to 100 mol, preferably 1 to 40 mol per mol of the compound (XII) or a salt thereof. The strength of acid or base is normally about 0.1 to 10N, preferably 2 to 10N. Although varying depending on reaction temperature, reaction time is normally about 1 to 24 hours, preferably about 2 to 10 hours.

Thus-obtained compound (I'), (VI) or (IX) or a salt thereof having a primary or secondary amino group which may have a substituent may have a hydrocarbon group which may have a substituent introduced to the primary or secondary amino group thereof, to yield the compound (I'), (VI) or (IX) or a salt thereof having an amino group substituted for by a hydrocarbon group which may have a substituent. The starting material compound (I'), (VI) or (IX) or a salt thereof having an primary or secondary amino group may be used after isolation and purification by known means such as concentration, liquid property conversion, redissolution, solvent extraction, fractional distillation, distillation, crystallization, recrystallization and chromatography, or may be used in the form of a reaction mixture as such, without isolation, as a starting material. Accordingly, the compound (I'), (VI) or (IX) or a salt thereof having an amino group substituted for by a hydrocarbon group which may have a substituent can also be produced by reaction between the compound (I'), (VI) or (IX) or a salt thereof having a primary or secondary amino group and a compound represented by the formula:

$$R^7—Z^3 \quad (XIII)$$

wherein $R^7$ represents an optionally substituted hydrocarbon group; $Z^3$ represents a leaving group.

The optionally substituted hydrocarbon group for $R^7$ is exemplified by the same optionally substituted hydrocarbon groups as specified for $R^2$, $R^3$ or $R^6$ above.

The leaving group for $Z^3$ is exemplified by halogen atoms (e.g., chlorine, bromine and iodine), $C_{1-6}$ alkylsulfonyloxy groups (e.g., methanesulfonyloxy, ethanesulfonyloxy) and $C_{6-10}$ arylsulfonyloxy groups (e.g., benzenesulfonyloxy and p-toluenesulfonyloxy), with preference given to halogen atoms (e.g., chlorine).

This reaction can be carried out in the presence or absence of a solvent, with a base added as necessary. Bases for this purpose include inorganic bases such as sodium carbonate, potassium carbonate, lithium carbonate, sodium hydroxide, potassium hydroxide, sodium methoxide, sodium ethoxide and sodium hydride, and organic bases such as pyridine, 4-dimethylaminopyridine and triethylamine. Any solvent can be used, as long as it does not interfere with the reaction, such solvents include lower alcohols such as methanol, ethanol, propanol, isopropanol, n-butanol and t-butanol, ethers such as dioxane, ether and tetrahydrofuran, aromatic hydrocarbons such as toluene, benzene and xylene, halogenated hydrocarbons such dichloromethane, 1,2-dichloroethane, amides such as dimethylformamide, dimethylacetamide and hexamethylphosphonotriamide, and esters such as ethyl acetate and butyl acetate. This reaction can be carried out under cooling conditions (about 0° to 10° C.), at room temperature (about 10° to 40° C.) or under heating conditions (about 40° to 120° C.). Reaction time is normally 10 minutes to 48 hours, preferably 2 to 16 hours. The amount of compound (XIII) used is preferably 0.3 to 5.0 mol per mol of the compound (I'), (VI) or (IX) or a salt thereof having a primary or secondary amino group. The amount of base used is normally about 1 or more mol, preferably 1.1 to 5 mol per mol of the compound (I'), (VI) or (IX) or a salt thereof having a primary or secondary amino group.

Also, this reaction may be accelerated as appropriate in the presence of an iodide such as sodium iodide, potassium iodide or lithium iodide. In this case, the amount of iodide used is normally 1 to 5 mol, preferably 1.1 to 1.5 mol per mol of the compound (XI).

The compound (XIII) can be produced by known method or modifications thereof.

The novel compound (I) or a salt thereof can be produced by the same method as used to produce the compound (I') or a salt thereof above.

The compound (I) or (I') thus obtained can be converted to a salt by a conventional method when it is in a free form, and can be converted to a free form or another salt by a conventional method when it is in a salt form. The compound (I) or (I') or a salt thereof can be isolated and purified by known methods as described above. Also, the compound (I) or (I') or a salt thereof involves steric isomers based on the presence of asymmetric carbon atoms. These isomers can also be isolated and purified by known methods as described above or other methods such as fractional recrystallization, and chromatography using optically active columns.

The compound (I) or (I') or a salt thereof acts on the central nervous system of mammals, potently inhibits cholinesterase and exhibit excellent antiamnestic effects on various amnesia inducing actions in humans or animals (e.g., mice). Further, the compound (I) or (I') or salts thereof has monoamine (e.g. norepinephirine, serotonin, etc.) reuptake inhibitory activity, and exhibit excellent antidepressant activity, etc. in humans or animals (e.g. mice).

The compound (I) or (I') or a salt thereof is remarkably excellent in separation of effects on central nervous system from those on peripheral nervous system, as compared with physostigmine and, at the anti-amnestic and antidepressant dose level, do not cause peripheral nervous system effects such as spasm, salivation, diarrhea, etc., with prolonged duration of action and with low toxicity, and they exhibit marked effect in oral administration. The acute toxicity ($LD_{50}$) of the compound (I) or (I') or a salt thereof exceeds 100 mg/kg.

For these reasons, the compound of the present invention serves well as a safe brain function improving drug in mammals, including humans.

Diseases against which the compound of the present invention is effective include senile dementia, Alzheimer's disease, Huntington's chorea, hyperkinesis and mania. The inventive compound can be used to prevent or treat these diseases.

The compound of the present invention can be orally or non-orally administered to mammals, including humans, normally in the form of a pharmaceutical preparation with a pharmaceutically acceptable carrier or excipient.

Acceptable dosage forms are oral preparations (e.g., powders, tablets, granules, capsules) and non-oral preparations (e.g., suppositories, injectable preparations). These preparations can be prepared by known methods. Although varying depending on type of disease, symptoms and other factors, ordinary daily dose for oral administration is about 0.01 mg to 50 mg, preferably 0.1 to 30 mg, more preferably 0.5 to 10 mg for an adult weighing 70 kg.

The present invention is hereinafter described in more detail by means of the following working examples, reference examples, formulation examples and an experimental example, but the scope of the invention is not limited to these examples.

Elution in column chromatography in the experimental and reference examples was conducted with observation by TLC (thin layer chromatography), unless otherwise stated. In the TLC observations, TLC was conducted on a TLC plate of Merck 60F$_{254}$, in which the developing solvent was the same as the column chromatography eluent and the detector was a UV detector. Also, 48% HBr was sprayed over the spot on the TLC plate, followed by thermal hydrolysis, after which the ninhydrin reagent was sprayed, followed by heating. When the response is positive, a red to red-purple color should develop. Using this phenomenon in combination with UV detection, the eluted fraction containing the desired product was confirmed and collected. The column packing silica gel was Merck Kiesel Gel 60 (70–230 mesh), unless otherwise stated.

"Normal temperature" or "room temperature" is generally defined to be between about 5° C. and 40° C., "normal pressure" meaning a pressure of about 1 atm. Also, % is percent by weight unless otherwise stated, and C₄H₄O₄ indicates fumaric acid.

REFERENCE EXAMPLE 1

1-Formyl-1,2,2a,3,4,5-hexahydrobenz[cd]indole

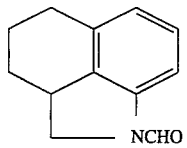

(1) A mixture of 5.0 g of 1-benzoyl-1,2,2a,3,4,5-hexahydrobenz[cd]indol-5-one, 2.7 g of potassium hydroxide, 2 ml of hydrazine hydrate and 20 ml of ethylene glycol was heated at 120° C. for 2 hours and then at 190° C. for 3 hours. After mixture cooling, water was added, and the reaction product was extracted with dichloromethane. After the extract was dried over magnesium sulfate, the solvent was distilled off under reduced pressure. The residue was purified by silica gel column chromatography (developing solvent: dichloromethane-ethyl acetate=10:1 (v/v)) to yield 1.9 g of 1,2,2a,3,4,5-hexahydrobenz[cd]indole as a colorless crystal having a melting point of 58° to 59° C.

Elemental analysis (for $C_{11}H_{13}N$): Calculated: C, 82.97; H, 8.23; N, 8.80. Found: C, 83.02; H, 8.18; N, 8.80.

(2) To 18 ml of formic acid, 6 ml of acetic anhydride was added dropwise, followed by stirring at room temperature for 20 minutes. After a solution of 1.6 g of 1,2,2a,3,4,5-hexahydrobenz[cd]indole as obtained in (1) above in 2 ml of dichloromethane was added, the mixture was stirred at room temperature for 30 minutes. After water was added to the reaction mixture, the reaction product was extracted with dichloromethane. The extract was washed by sequential additions of a 5% aqueous sodium hydroxide solution and water, after which the solvent was distilled off under reduced pressure. The resulting crystal was recrystallized from dichloromethane-ether to yield the title compound as a colorless crystal having a melting point of 93° to 94° C.

Elemental analysis (for $C_{12}H_{13}NO$): Calculated: C, 76.98; H, 7.00; N, 7.48. Found: C, 76.94; H, 7.01; N, 7.52.

REFERENCE EXAMPLE 2

3-Chloro-(1-formyl-1,2,2a,3,4,5-hexahydrobenz[cd]indol-6-yl)-1-propanone

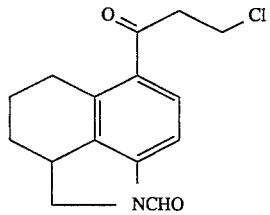

To a 10 ml solution of 0.8 g of 1-formyl-1,2,2a,3,4,5-hexahydrobenz[cd]indole as obtained in Reference Example 1 and 0.55 g of 3-chloropropionyl chloride in 10 ml of 1,2-dichloroethane, 1.4 g of aluminum chloride was added portionwise, followed by stirring at room temperature for 4 hours. The reaction mixture was poured over ice water, and the reaction product was extracted with dichloromethane. After the extract was dried over anhydrous sodium sulfate, the solvent was distilled off under reduced pressure. The residue was purified by silica gel column chromatography (developing solvent: hexane-ethyl acetate-dichloromethane=10:3:1 (v/v)) to yield 0.7 g of the title compound as a colorless crystal having a melting point of 82° to 85° C.

Elemental analysis (for $C_{15}H_{16}ClNO_2$): Calculated: C, 64.87; H, 5.81; N, 5.04. Found: C, 64.98; H, 5.84; N, 4.99.

REFERENCE EXAMPLE 3

3-Chloro-1-(benzofuran-2-yl)-1-propanone

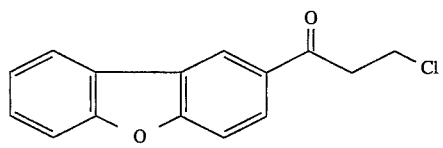

Using dibenzofuran and 3-chloropropionyl chloride, the same procedure as in Reference Example 2 was followed, to yield the title compound as a colorless crystal having a melting point of 116° to 118° C.

Elemental analysis (for $C_{15}H_{11}ClO_2$): Calculated: C, 69.64; H, 4.29. Found: C, 69.80; H, 4.25.

REFERENCE EXAMPLE 4

3-Chloro-1-(2-oxo-1,2,2a,3,4,5-hexahydrobenz[cd]indol-6-yl)-1-propanone

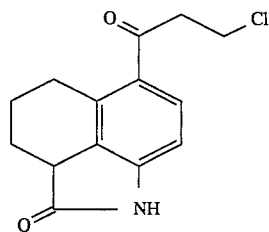

Using 2a,3,4,5-tetrahydrobenz[cd]indol-2(1H)-one and 3-chloropropionyl chloride, the same procedure as in Reference Example 2 was followed, to yield the title compound as a colorless needle crystal having a melting point of 175° to 178° C.

Elemental analysis (for $C_{14}H_{14}ClNO_2$): Calculated: C, 63.76; H, 5.35; N, 5.31. Found: C, 63.58; H, 5.29; N, 5.33.

REFERENCE EXAMPLE 5

3-Chloro-1-(3-carbazolyl)-1-propanone

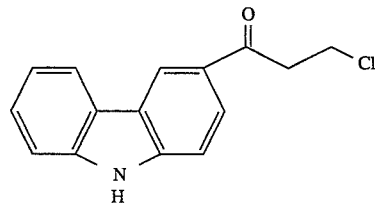

To a 90 ml solution of 5.0 g of carbazole and 4.2 g of 3-chloropropionyl chloride in nitromethane, 4.8 g of aluminum chloride was added portionwise, followed by stirring at 45° C. for 1 hour. The reaction mixture was poured over 100 ml of ice water, and the organic layer was separated and then washed by sequential additions of a 50 ml saturated aqueous sodium hydrogen carbonate solution and 50 ml of distilled water. After the mixture was dried over anhydrous sodium sulfate, the solvent was distilled off to yield a crystalline residue. The residue was collected by filtration and dried under reduced pressure to yield 4.8 g of the title compound as a light red crystal having a melting point of 148° to 151° C.

Elemental analysis (for $C_{15}H_{12}ClNO$): Calculated: C, 69.91; H, 4.69; N, 5.43. Found: C, 69.82; H, 4.76; N, 5.44.

REFERENCE EXAMPLE 6

Using known tricyclic condensed heterocyclic rings and 3-chloropropionyl chloride, the same procedure as in Reference Example 2 was followed, to yield the compounds listed in Table 52.

TABLE 52

$$Ar-\overset{\overset{O}{\|}}{C}-CH_2CH_2Cl$$

| Comp. No. | Ar | Melting Point (°C.) | Molecular Formula | Elemental Analysis Calculated (Found) | | |
|---|---|---|---|---|---|---|
| | | | | C | H | N |
| 1 | | 169–170 | $C_{14}H_{14}ClNO_2$ | 63.76 (63.68 | 5.35 5.20 | 5.31 5.33) |
| 2 | | 138–139 | $C_{14}H_{14}ClNO_2$ | 63.76 (63.81 | 5.35 5.31 | 5.31 5.40) |
| 3 | | 123–125 | $C_{15}H_{16}ClNO_2$ | 64.87 (64.64 | 5.81 5.77 | 5.04 5.03) |
| 4 | | 146–148 | $C_{15}H_{16}ClNO_2$ | 64.87 (64.59 | 5.81 5.73 | 5.04 4.98) |
| 5 | | 142–144 | $C_{15}H_{16}ClNO_2$ | 64.87 (64.90 | 5.81 5.76 | 5.04 5.01) |
| 6 | | 127–129 | $C_{18}H_{16}ClNO_2$ | 68.90 (68.93 | 5.14 5.04 | 4.46 4.37) |

TABLE 52-continued

Ar—C(=O)—CH$_2$CH$_2$Cl

| Comp. No. | Ar | Melting Point (°C.) | Molecular Formula | Elemental Analysis Calculated (Found) | | |
|---|---|---|---|---|---|---|
| | | | | C | H | N |
| 7 | (2-benzyl-phenyl with N-CHO, methyl-substituted) | 132–134 | C$_{18}$H$_{16}$ClNO$_2$ | 68.90 (68.72 | 5.14 4.98 | 4.46 4.51) |
| 8 | (diphenyl ether with N-CHO, methyl-substituted) | 136–138 | C$_{17}$H$_{14}$ClNO$_3$ | 64.66 (64.61 | 4.47 4.49 | 4.43 4.32) |
| 9 | (tricyclic benzazocinone, methyl-substituted) | 137–140 | C$_{16}$H$_{18}$ClNO$_2$ | 65.86 (65.79 | 6.22 6.24 | 4.80 4.83) |

REFERENCE EXAMPLE 7

3-(1-Methoxycarbonyl-4-piperidinyl)propionic Acid

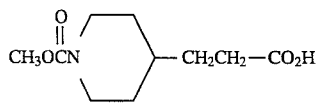

In 208 ml of conc. hydrochloric acid, 99.63 g of 3-(1-acetyl-4-piperidinyl)propionic acid was suspended; the suspension was stirred under refluxing conditions for six hours. The reaction mixture was then concentrated to half under reduced pressure and allowed to stand at 0° C. overnight. The crystalline precipitate was collected by filtration and washed with cold ethanol. After drying, 77.9 g of 3-(4-piperidinyl)propionic acid was obtained. Of this product, 77.5 g was dissolved in a mixture of 360 ml of dichloromethane and 400 ml of 3N sodium hydroxide aqueous solution. To the mixture, 34 ml of methyl chlorocarbonate was added dropwise at 0° C., and stirred at room temperature for five hours. After the pH of the aqueous layer was adjusted to 8 by addition of a 50% sodium hydroxide aqueous solution, the organic layer was separated and dried over anhydrous sodium sulfate. The solvent was then evaporated under reduced pressure. To the residue, isopropyl ether-hexane was added to yield 76.5 g of the title compound as colorless crystals having a melting point of 88°–90° C.

Elemental analysis (for C$_{10}$H$_{17}$NO$_4$). Calculated: C, 55.80; H, 7.96; N, 6.51. Found: C, 55.69; H, 8.01; N, 6.47

REFERENCE EXAMPLE 8

8-(4-Chlorobutylyl)-1,2,5,6-tetrahydro-4H-pyroro[3,2,1-ij]quinolin-4-one

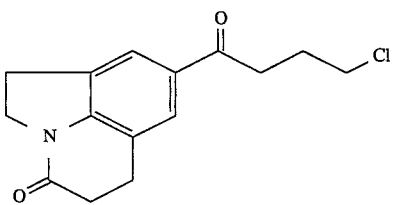

By the same procedure as used in Example 2, 5 g of 1,2,5,6-tetrahydro-4H-pyroro[3,2,1-ij]quinolin-4-one and 4.15 g of 4-chlorobutylyl chloride were reacted to yield 6.4 g of the title compound as colorless needles having a melting point of 130°–131° C.

Elemental analysis (for C$_{15}$H$_{16}$ClNO$_2$). Calculated: C, 64.87; H, 5.81; N, 5.04. Found: C, 64.71; H, 5.88; N, 4.99.

EXAMPLE 1

1-(1-Formyl-1,2,2a,3,4,5-hexahydrobenz[cd]indol-6-yl)-3-[1-(phenylmethyl)piperazin-4-yl]-1-propanone

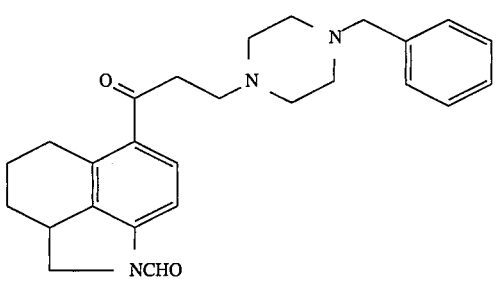

To a suspension of 0.65 g of 3-chloro-(1-formyl-1,2,2a, 3,4,5-hexahydrobenz[cd]indol-6-yl)-1 -propanone as obtained in Reference Example 2 and 0.42 g of potassium carbonate in 20 ml of dichloromethane, a 5 ml solution of 0.41 g of 1-(phenylmethyl)piperazine in methanol was added, followed by stirring at room temperature for 30 minutes. After the solvent was distilled off under reduced pressure, water was added to the residue, and the reaction product was extracted with dichloromethane. After the extract was dried over anhydrous sodium sulfate, the solvent was distilled off under reduced pressure. The resulting oily substance was purified by silica gel column chromatography (developing solvent: ethyl acetate-methanol=10:1 (v/v)) to yield 0.6 g of the title compound as a colorless oily substance.

Elemental analysis (for $C_{26}H_{31}N_3O_2$): Calculated: C, 74.79; H, 7.48; N, 10.06. Found: C, 74.59; H, 7.52; N, 10.03

EXAMPLE 2

1-(1,2,2a,3,4,5-Hexahydrobenz[cd]indol-6-yl)3-[1-(phenylmethyl)piperazin-4-yl]-1 -propanone Trihydrochloride

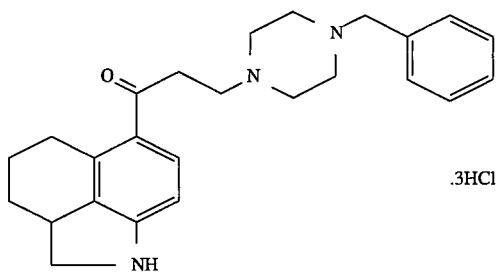

To a 10 ml solution of 0.4 g of 1-(1-formyl-1,2,2a,3,4,5-hexahydrobenz[cd]indol-6-yl)-3 -[1-(phenylmethyl)piperazin-4-yl]-1-propanone as obtained in Example 1 in methanol, 10 ml of 3N hydrochloric acid was added, followed by stirring at room temperature for 30 minutes. After the methanol was distilled off under reduced pressure, a 10% aqueous sodium hydroxide solution was added to obtain a solution pH of about 10, and the reaction product was extracted with dichloromethane. After the product was dried over anhydrous sodium sulfate, 0.8 ml of 4N methanol-hydrochloric acid was added. The solvent was distilled off under reduced pressure, and the resulting solid was crystallized from methanol-ether to yield 0.46 g of the title compound as a colorless crystal having a melting point of 207° to 211° C. (decomposed).

Elemental analysis (for $C_{25}H_{31}N_3O \cdot 3HCl$): Calculated: C, 60.18; H, 6.87; N, 8.42. Found: C, 59.98; H, 7.01; N, 8.22

EXAMPLE 3

3-(1-Acetylpiperidin-4-yl)-1-(1-formyl-1,2,2a,3, 4,5-hexahydrobenz[cd]indol-6 -yl)-1-propanone

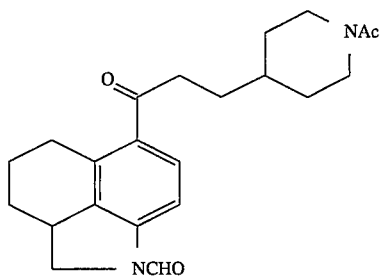

To a 10 ml solution of 0.8 g of 1-formyl-1,2,2a,3,4,5-hexahydrobenz[cd]indole as obtained in Reference Example 1 and 1.2 g of 3-(1-acetylpiperidin-4-yl)propionyl chloride in 1,2-dichloroethane, 2.0 g of aluminum chloride was added portionwise, followed by heating and refluxing for 2 hours. The reaction mixture was poured over ice water, and the reaction product was extracted with dichloromethane. After the extract was dried over anhydrous sodium sulfate, the solvent was distilled off under reduced pressure. The resulting residue was purified by silica gel column chromatography (developing solvent: ethyl acetate-methanol=20:1 (v/v)) to yield 1.0 g of the title compound as a viscous oily substance.

Elemental analysis (for $C_{22}H_{28}N_2O_3$): Calculated: C, 71.71; H, 7.66; N, 7.60. Found: C, 71.47; H, 7.58; N, 7.57

EXAMPLE 4

1-(1,2,2a,3,4,5-Hexahydrobenz[cd]indol-6-yl)-3-[1-(phenylmethyl) piperidin-4-yl]-1-propanone Dihydrochloride

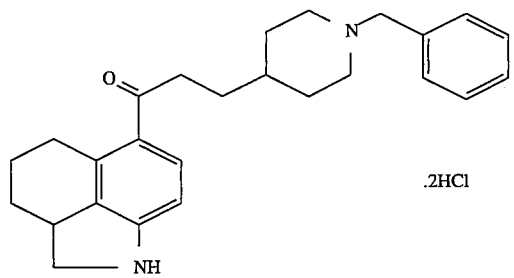

A mixture of 0.4 g of 3-(1-acetylpiperidin-4-yl)-1-(1-formyl-1,2,2a,3,4,5 -hexahydrobenz[cd]indol-6-yl)-1-propanone as obtained in Example 3 and 10 ml of concentrated hydrochloric acid was heated and refluxed for 8 hours. After the concentrate hydrochloric acid was distilled off under reduced pressure, the residue was dissolved in water, and a 10% aqueous sodium hydroxide solution was added to obtain a solution pH of about 11. The reaction product was extracted with dichloromethane. After the product was dried over anhydrous sodium sulfate, the solvent was distilled off under reduced pressure. The resulting oily substance was dissolved in 10 ml of ethanol, after which 0.2 g of potassium carbonate was added, followed by drop by drop addition of a 2 ml ethanol solution of 0.17 g of benzyl bromide. After the mixture was stirred at room temperature for 1 hour, the solvent was distilled off under reduced pressure. After water was added to the residue, the reaction product was extracted with dichloromethane. After the extract was dried over anhydrous sodium sulfate, the solvent was distilled off under reduced pressure. The resulting oily substance was purified by silica gel column chromatography (developing solvent: dichloromethane-ethyl acetate=2:1 (v/v)) to yield a free base form of the title compound as a colorless oily substance. After 0.6 ml of 4N methanol-hydrochloric acid was added to the oily substance, the solvent was distilled off, to yield 0.36 g of the title compound as an amorphous powder.

Elemental analysis (for $C_{26}H_{32}N_2O \cdot 2HCl$): Calculated: C, 67.67; H, 7.43; N, 6.07. Found: C, 67.43; H, 7.44; N, 6.02

EXAMPLE 5

1-(Dibenzofuran-2-yl)-3-[1-(phenylmethyl)piperazin-4-yl]-1-propanone

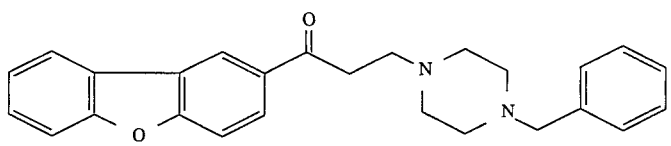

Using 3-chloro-1-(dibenzofuran-2-yl)-1-propanone as obtained in Reference Example 3 and 1-(phenylmethyl)piperazine, the same procedure as in Example 1 was followed, to yield the title compound as a colorless crystal having a melting point of 135° to 136° C.

Elemental analysis (for $C_{26}H_{26}N_2O_2$): Calculated: C, 78.36; H, 6.58; N, 7.03. Found: C, 78.21; H, 6.60; N, 6.99

EXAMPLE 6

1-[1-(Phenylmethyl)-1,2,2a,3,4,5-hexahydrobenz[cd]indol-6-yl]-3-[1-(phenylmethyl)piperidin-4-yl]-1-propanone Fumarate

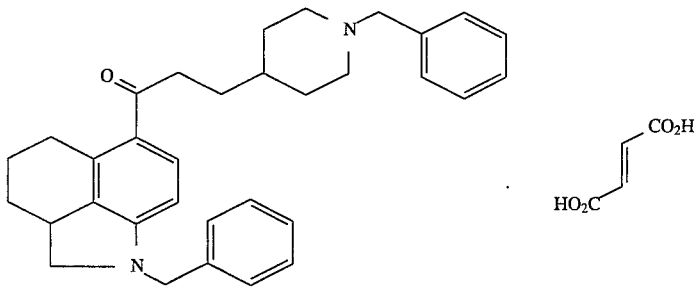

To a 10 ml solution of 0.5 g of 1-(1,2,2a,3,4,5-hexahydrobenz[cd]indol-6-yl)-3-[1-(phenylmethyl)piperidin-4-yl]-1-propanone in ethanol, 0.23 g of potassium carbonate was added, followed by dropwise addition of a 2 ml ethanol solution of 0.22 g of benzyl bromide. After the mixture was stirred at room temperature for 1 hour, the solvent was distilled off under reduced pressure. After water was added to the residue, the reaction product was extracted with dichloromethane. After the extract was dried over anhydrous sodium sulfate, the solvent was distilled off under reduced pressure. The resulting oily substance was purified by silica gel column chromatography (developing solvent: ethyl acetate-methanol=40:1 (v/v)) to yield 0.47 g of a free base form of the title compound as a colorless crystal having a melting point of 143° to 146° C.

Elemental analysis (for $C_{33}H_{38}N_2O$): Calculated: C, 82.80; H, 8.00; N, 5.85. Found: C, 82.71; H, 8.02; N, 5.74

To a 5 ml solution of the resulting crystal in dichloromethane, a solution of 114 mg of fumaric acid in 5 ml of methanol was added, after which the solvent was distilled off under reduced pressure, to yield 0.53 g of the title compound as a colorless crystal having a melting point of 164° to 166° C.

Elemental analysis (for $C_{33}H_{38}N_2O \cdot C_4H_4O_4 \cdot 1/2H_2O$): Calculated: C, 73.61; H, 7.18; N, 4.64. Found: C, 73.43; H, 7.04; N, 4.71

EXAMPLE 7

The same procedure as in Example 6 was followed to yield the compounds listed in Table 53.

TABLE 53

[Structure diagram of compound with piperidine-benzyl group, tetrahydro-benzindole core with N-R]

| Compound No. | R | Melting Point (°C.) | Molecular Formula | Elemental Analysis Calculated (Found) | | |
|---|---|---|---|---|---|---|
| | | | | C | H | N |
| 1 | CH$_2$—C$_6$H$_4$—OCH$_3$ | 115–117 | C$_{34}$H$_{40}$N$_2$O$_2$ | 80.28 (80.11 | 7.93 7.96 | 5.51 5.38) |
| 2 | CH$_2$—C$_6$H$_4$—OCH$_3$ | 110–114 | C$_{34}$H$_{40}$N$_2$O$_2$· C$_4$H$_4$O$_4$ | 73.05 (72.93 | 7.10 7.15 | 4.48 4.31) |

EXAMPLE 8

1-(1-Acetyl-1,2,2a,3,4,5-hexahydrobenz[cd]indol-6-yl)-3-[1-(phenylmethyl)piperidin-4-yl]-1-propanone Fumarate

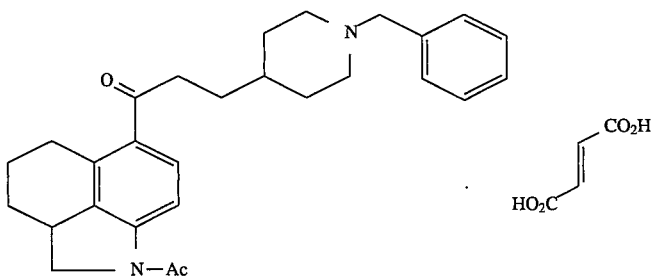

To a 10 ml solution of 0.5 g of 1-(1,2,2a,3,4,5-hexahydrobenz[cd]indol-6-yl)-3-[1 -(phenylmethyl)piperidin-4-yl]-1-propanone in dichloromethane, 0.14 g of acetic anhydride was added, followed by stirring at room temperature for 30 minutes. After 20 ml of a 5% aqueous sodium hydroxide solution was added to the reaction mixture, the reaction product was extracted with dichloromethane. After the extract was dried over anhydrous sodium sulfate, the solvent was distilled off under reduced pressure. The residue was purified by silica gel column chromatography (developing solvent: ethyl acetate-methanol=20:1 (v/v)) to yield 0.48 g of a free base form of the title compound as a colorless powder. To a 5 ml solution of the resulting powder in dichloromethane, a 5 ml solution of 0.13 g of fumaric acid in methanol was added, after which the solvent was distilled off under reduced pressure, to yield 0.54 g of the title compound as a colorless crystal having a melting point of 173° to 175° C.

Elemental analysis (for C$_{28}$H$_{34}$N$_2$O$_2$·C$_4$H$_4$O$_4$): Calculated: C, 70.31; H, 7.01; N, 5.12. Found: C, 70.11; H, 7.16; N, 5.13

EXAMPLE 9

1-(2-Oxo-2a,3,4,5-tetrahydro-1H-benz[cd]indol-6-yl)-3-[4-(phenylmethyl)piperazin-1-yl]-1-propanone Dihydrochloride

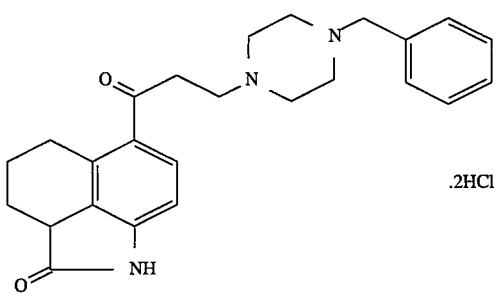

Using the compound obtained in Reference Example 4, the same procedure as in Example 1 was followed to yield a free base form of the title compound, which was converted to a dihydrochloride by the method described in Example 2 to yield the title compound as a colorless crystal having a melting point of 185° to 188° C.

Elemental analysis (for $C_{25}H_{29}N_3O_2 \cdot 2HCl$): Calculated: C, 63.02; H, 6.56; N, 8.82. Found: C, 62.88; H, 6.57; N, 8.75

EXAMPLE 10

1-(3-Carbazolyl)-3-(4-benzylpiperazin-1-yl)-1-propanone Dihydrochloride

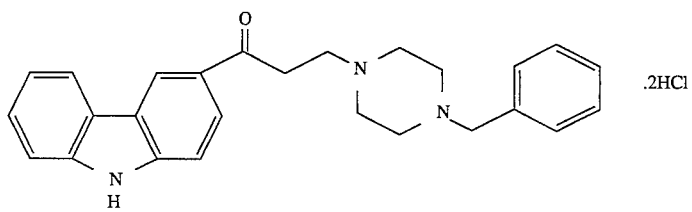

.2HCl 2.1 g of 3-chloro-1-(3-carbazolyl)-1-propanone as obtained in Reference Example 5 was dissolved in 50 ml of dichloromethane, and 1.7 g of potassium carbonate and 4.4 g of 1-benzylpiperazine were added, followed by stirring at room temperature for 4 hours. After 30 ml of distilled water was added, the organic layer was separated and then washed with 50 ml of distilled water. After the mixture was dried over anhydrous sodium sulfate, the solvent was distilled off to yield a crystalline residue. The residue was dried under reduced pressure to yield 3.0 g of a free form of the title compound as a colorless crystal having a melting point of 124° to 126° C. The 3.0 g of free compound was dissolved in methanol, and 4.0 ml of 4N methanol-hydrochloric acid was added, after which the solvent was distilled off under reduced pressure, to yield a solid, which was then washed with methanol, to yield 2.8 g of the title compound as a light red crystal having a melting point of 206° to 208° C.

Elemental analysis (for $C_{26}H_{27}N_3O \cdot 2HCl \cdot 1/2H_2O$): Calculated: C, 65.13; H, 6.31; N, 8.76. Found: C, 65.13; H, 6.23; N, 8.72

EXAMPLE 11

1-(3-Carbazolyl)-3-(1-acetylpiperidin-4-yl)-1-propanone

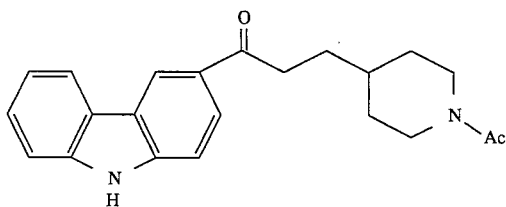

To a 90 ml solution of 5.0 g of carbazole and 7.2 g of 3-(1-acetylpiperidin-4-yl)propionyl chloride in nitromethane, 9.3 g of aluminum chloride was added little by little, followed by stirring at 70° C. for 11 hours. The reaction mixture was poured over 100 ml of ice water, and the organic layer was separated and then washed by sequential additions of a 50 ml saturated aqueous sodium hydrogen carbonate solution and 50 ml of distilled water. After the mixture was dried over anhydrous sodium sulfate, the solvent was distilled off to yield an oily residue. The residue was purified by silica gel column chromatography (developing solvent: ethyl acetate-methanol=20:1 (v/v)) to yield 2.6 g of the title compound as a light yellow powder.

Elemental analysis (for $C_{22}H_{24}N_2O_2$): Calculated: C, 75.83; H, 6.94; N, 8.04. Found: C, 75.77; H, 6.98; N, 7.96

EXAMPLE 12

1-(3-Carbazolyl )-3-(4-piperidinyl)-1-propanone

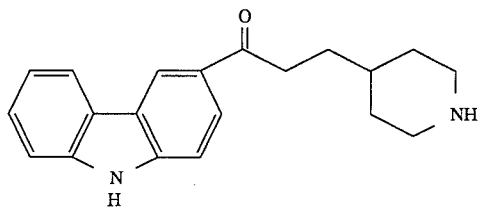

A solution of 2.1 g of 1-(3-carbazolyl)-3-(1-acetylpiperidin-4-yl)-1-propanone as obtained in Example 11 in concentrated hydrochloric acid was stirred under refluxing conditions for 19 hours. The solvent was distilled off to yield a crystalline residue. A portion (about 0.25 g) of the residue was collected by filtration and dried under reduced pressure to yield 0.24 g of a monohydrochloride of the title compound as a light blue crystal having a melting point of 243° to 247° C. (decomposed).

Elemental analysis (for $C_{20}H_{22}N_2O \cdot HCl \cdot 1/2H_2O$): Calculated: C, 68.27; H, 6.87; N, 7.96. Found: C, 68.56; H, 6.60; N, 7.99

The remaining portion of the residue was dissolved in 20 ml of distilled water. After 10 ml of a 10% aqueous sodium hydroxide solution and 20 ml of dichloromethane were added to the solution, the organic layer was separated and washed with 30 ml of distilled water and then dried over anhydrous sodium sulfate, after which the solvent was distilled to yield a crystal, which was dried under reduced pressure to yield 1.2 g of the title compound as a light yellow crystal having a melting point of 206° to 209° C.

Elemental analysis (for $C_{20}H_{22}N_2O$): Calculated: C, 78.40; H, 7.24; N, 9.14. Found: C, 78.35; H, 7.31; N, 9.08

EXAMPLE 13

1-(3-Carbazolyl)-3-[1-(phenylmethyl)piperidin-4-yl]-1-propanone Hydrochloride

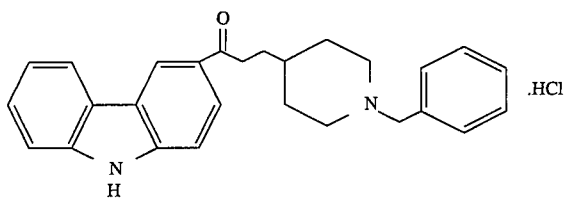

To a solution of 0.7 g of 1-(3-carbazolyl)-3-(piperidin-4-yl)-1-propanone as obtained in Example 12 in a mixture of N,N-dimethylformamide-dichloromethane (3/1 (v/v)), 0.41 g of potassium carbonate was added, followed by stirring at 15° C. for 15 minutes. Then, a solution of 0.37 g of benzyl bromide in 3 ml of dichloromethane was added dropwise, followed by stirring at room temperature for 2.5 hours. After the solvent was distilled off, 30 ml of distilled water and 30 ml of dichloromethane were added, and the organic layer was separated, washed with 50 ml of distilled water and then dried over anhydrous sodium sulfate. The solvent was distilled off to yield a crystal, which was dried under reduced pressure to yield 0.69 g of a free base form of the title compound as a colorless crystal having a melting point of 155° to 158° C. A 0.55 g portion of this free base form was dissolved in methanol, and 0.5 ml of 4N methanol-hydrochloric acid was added, after which the solvent was distilled off under reduced pressure, to yield a solid, which was washed with ethanol, to yield 0.52 g of the title compound as a light blue crystal having a melting point of 206° to 208° C.

Elemental analysis (for $C_{27}H_{28}N_2O \cdot HCl \cdot 1/2H_2O$): Calculated: C, 73.37; H, 6.84; N, 6.34. Found: C, 73.46; H, 6.77; N, 6.46

EXAMPLE 14

3-(1-Acetylpiperidin-4-yl)-1-(1,2,2a,3,4,5-hexahydrobenz[cd]indol-6-yl)-1-propanone

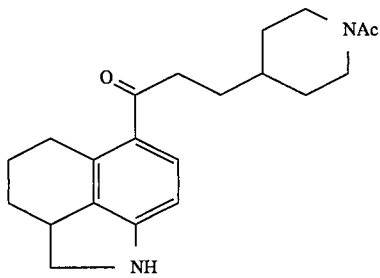

1) Using 17 g of 1-formyl-1,2,2a,3,4,5-hexahydrobenz[cd]indole (compound of Reference Example 1), the same procedure as in Example 3 was followed to yield 20 g of 3-(1-acetylpiperidin-4-yl)-1-(1-formyl-1,2,2a,3,4,5-hexahydrobenz[cd]indol-6-yl)-1-propanone.

2) A mixture of a 150 ml methanol solution of 20 g of the compound obtained in 1) above and 150 ml of 10% hydrochloric acid was stirred at room temperature for 30 minutes. After the methanol was distilled off under reduced pressure, a 10% aqueous sodium hydroxide solution was added to obtain a solution pH of about 10. The reaction product was extracted with dichloromethane. After the product was dried over anhydrous sodium sulfate, the solvent was distilled off under reduced pressure to yield a 17 g crude crystal of the title compound, which was recrystallized from dichloromethane-ether to yield a 9.8 g colorless crystal having a melting point of 167° to 169° C.

Elemental analysis (for $C_{21}H_{28}N_2O_2$): Calculated: C, 74.08; H, 8.29; N, 8.23. Found: C, 73.79; H, 8.33; N, 8.12

EXAMPLE 15

1-(1-Ethyl-1,2,2a,3,4,5-hexahydrobenz[cd]indol-6-yl)-3-[1-(phenylmethyl)piperidin-4-yl]-1-propanone Fumarate

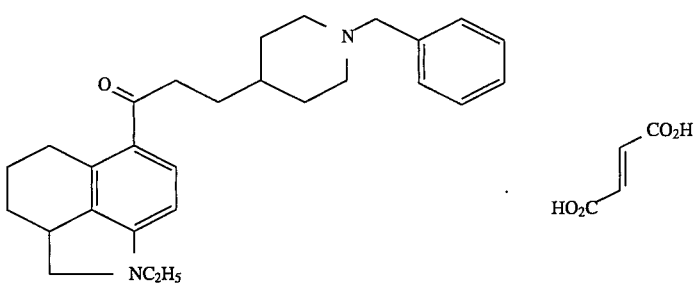

1) A 10 ml suspension of 1.0 g of 3-(1-acetylpiperidin-4-yl)-1-(1,2,2a,3,4,5-hexahydrobenz[cd]indol-6-yl)-1-propanone, 2.3 g of ethyl iodide and 0.53 g of potassium carbonate in ethanol was stirred at 60° to 70° C. for 12 hours. After the solvent was distilled off under reduced pressure, water was added to the residue, after which the reaction product was extracted with dichloromethane. After the extract was dried over anhydrous sodium sulfate, the solvent was distilled off under reduced pressure. The residue was purified by silica gel column chromatography (developing solvent: ethyl acetate) to yield 0.82 g of 3-(1-acetylpiperidin-4-yl)-1-(1-ethyl-1,2,2a,3,4,5-hexahydrobenz[cd]indol-6-yl)-1-propanone as a colorless oily substance.

Elemental analysis (for $C_{23}H_{32}N_2O_2$): Calculated: C, 74.96; H, 8.75; N, 7.60. Found: C, 74.88; H, 8.74; N, 7.62

2) Using 0.75 g of the compound obtained in 1) above, the same procedure as in Example 4 was followed to yield 0.65 g of a free base form of the title compound. To a 5 ml solution of the resulting 0.65 g of free base form in dichloromethane, a 5 ml solution of 0.18 g of fumaric acid in methanol was added, after which the solvent was distilled off under reduced pressure, to yield a crystal, which was recrystallized from ethanol, to yield 0.68 g of the title compound as a colorless crystal having a melting point of 177° to 178° C.

Elemental analysis (for $C_{28}H_{36}N_2O \cdot C_4H_4O_4 \cdot 3/2H_2O$): Calculated: C, 68.67; H, 7.74; N, 5.01. Found: C, 69.05; H, 7.50; N, 5.26

EXAMPLE 16

Using the compound obtained in Example 14, the same procedure as in Example 15 was followed to yield the compounds listed in Table 54.

TABLE 54

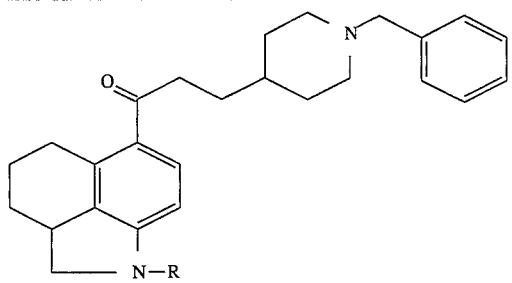

| Comp. No. | R | Melting Point (°C.) | Molecular Formula | Elemental Analysis Calculated (Found) | | |
|---|---|---|---|---|---|---|
| | | | | C | H | N |
| 1 | $CH_3$ | 160–162 | $C_{27}H_{34}N_2O \cdot C_4H_4O_4 \cdot \tfrac{1}{2}H_2O$ | 70.56 (70.46) | 7.45 7.27 | 5.31 5.44) |
| 2 | $(CH_2)_2CH_3$ | 200–204 | $C_{29}H_{38}N_2O \cdot C_4H_4O_4$ | 72.50 (72.24 | 7.74 7.73 | 5.12 5.27) |
| 3 | $CH(CH_3)_2$ | 149–153 | $C_{29}H_{38}N_2O \cdot C_4H_4O_4$ | 72.50 (72.47 | 7.74 7.67 | 5.12 5.28) |
| 4 | $(CH_2)_3CH_3$ | 189–193 | $C_{30}H_{40}N_2O \cdot C_4H_4O_4 \cdot \tfrac{1}{4}H_2O$ | 72.25 (72.19 | 7.94 7.91 | 4.96 5.19) |
| 5 | $CH_2CH(CH_3)_2$ | 180–181 | $C_{30}H_{40}N_2O \cdot C_4H_4O_4$ | 72.83 (72.64 | 7.91 7.87 | 5.00 4.76) |
| 6 | $(CH_2)_4CH_3$ | 179–181 | $C_{31}H_{42}N_2O \cdot C_4H_4O_4 \cdot \tfrac{1}{4}H_2O$ | 72.57 (72.64 | 8.09 8.03 | 4.84 5.07) |

EXAMPLE 17

Using the compound obtained in Reference Example 6, the same procedure as in Example 1 was followed to yield the compounds listed in Table 55.

TABLE 55

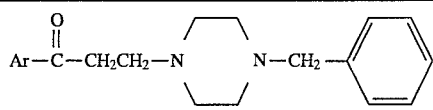

| Comp. No. | Ar | Melting Point (°C.) | Molecular Formula | Elemental Analysis Calculated (Found) | | |
|---|---|---|---|---|---|---|
| | | | | C | H | N |
| 1 | (tetrahydroquinoline structure) | 246–248 | $C_{25}H_{29}N_3O_2 \cdot$ 2HCl | 63.02 (62.78 | 6.56 6.60 | 8.82 8.77) |
| 2 | (tetrahydroquinoline structure) | 224–227 (decomp.) | $C_{25}H_{29}N_3O_2 \cdot$ $2HCl \cdot 1/2H_2O$ | 61.85 (61.57 | 6.64 6.47 | 8.66 8.36) |

TABLE 55-continued

Ar—C(=O)—CH₂CH₂—N(piperazine)N—CH₂—phenyl

| Comp. No. | Ar | Melting Point (°C.) | Molecular Formula | Elemental Analysis Calculated (Found) | | |
|---|---|---|---|---|---|---|
| | | | | C | H | N |
| 3 | (benzazepinone, methyl-substituted) | 224–228 (decomp.) | $C_{26}H_{31}N_3O_2 \cdot 2HCl \cdot H_2O$ | 61.41 (61.36 | 6.94 6.69 | 8.26 8.26) |
| 4 | (dihydroindole, methyl-substituted, with CH₃ branch) | 227–230 | $C_{26}H_{31}N_3O_2 \cdot 2HCl \cdot 1/2H_2O$ | 62.52 (62.77 | 6.86 6.68 | 8.41 8.45) |
| 5 | (dibenzazepine with CHO, methyl-substituted) | 168–172 (decomp.) | $C_{29}H_{31}N_3O_2 \cdot 2HCl \cdot 3H_2O$ | 60.00 (59.78 | 6.77 6.82 | 7.24 7.27) |
| 6 | (tetrahydroquinolinone, methyl-substituted) | 240–242 | $C_{26}H_{31}N_3O_2 \cdot 2HCl \cdot H_2O$ | 61.41 (61.35 | 6.94 6.82 | 8.26 8.29) |
| 7 | (diphenylmethane with N-CHO, methyl-substituted) | 197–200 | $C_{29}H_{31}N_3O_2 \cdot 2HCl$ | 66.15 (65.91 | 6.32 6.42 | 7.98 7.93) |
| 8 | (diphenyl ether with N-CHO, dimethyl-substituted) | 188–191 | $C_{28}H_{29}N_3O_3 \cdot 2HCl \cdot 1/2H_2O$ | 62.57 (62.87 | 6.00 5.88 | 7.82 7.85) |
| 9 | (benzazepinone, ethyl-linked, methyl-substituted) | 210–215 (decomp.) | $C_{27}H_{33}N_3O_2 \cdot 2HCl \cdot 3/2H_2O$ | 61.01 (61.16 | 7.21 7.03 | 7.91 7.71) |

TABLE 55-continued $$Ar-\overset{O}{\underset{\|}{C}}-CH_2CH_2-N\diagup\diagdown N-CH_2-\diagup\!\!\!\diagdown$$

| Comp. No. | Ar | Melting Point (°C.) | Molecular Formula | Elemental Analysis Calculated (Found) | | |
|---|---|---|---|---|---|---|
| | | | | C | H | N |
| 10 | (structure: tricyclic with N-CHO and methyl) | 188–191 | $C_{30}H_{33}N_3O_2$·2HCl·H$_2$O | 64.51 (64.69 | 6.68 6.74 | 7.52 7.62) |

EXAMPLE 18

1-(2-Oxo-1H-benz[cd]indol-6-yl)-3-[4-(phenylmethyl)piperazin-1-yl]-1-propanone Dihydrochloride

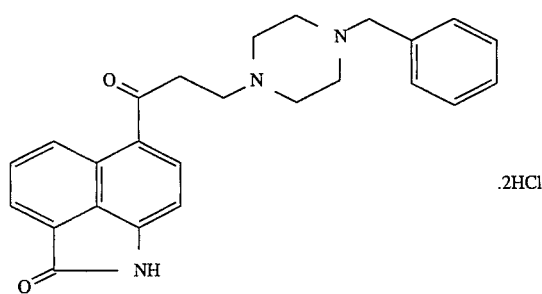

.2HCl

1) Using 7.5 g of benz[cd]indol-2(1H)-one and 6.2 g of 3-chloropropionyl chloride, the same procedure as in Reference Example 2 was followed to yield 4.8 g of an about 1:1 mixture of 3-chloro-1-(2-oxo-1H-benz[cd]indol-6 -yl)-1-propanone and unreacted benz[cd]indol-2(1H)-one.

2) To a solution of 1.0 g of the mixture obtained in 1) above in a mixture of dimethylformamide-dichloromethane (2 ml/20 ml), 0.68 g of 1-benzylpiperazine and 0.34 g of potassium carbonate were added, followed by stirring at room temperature for 1 hour. After the solvent was distilled off under reduced pressure, water was added to the residue, after which the reaction product was extracted with dichloromethane. After the extract was dried over anhydrous sodium sulfate, the solvent was distilled off. The residue was purified by silica gel column chromatography [developing solvent: ethyl acetate-methanol=10:1 (v/v)] to yield a fraction containing the desired product. The solvent was distilled off under reduced pressure to yield 0.52 g of a free base form of the title compound as a colorless powder having a melting point of 208° to 210° C., which was then converted to a dihydrochloride by the method described in Example 2 to yield 0.51 g of the title compound as a colorless crystal having a melting point of 166° to 170° C.

Elemental analysis (for $C_{25}H_{26}N_3O_2$·2HCl·3/2H$_2$O): Calculated: C, 60.12; H, 6.05; N, 8.41. Found: C, 60.17; H, 6.25; N, 8.19

EXAMPLE 19

The same procedure as in Example 18 was followed to yield the compounds listed in Table 56.

TABLE 56

$$Ar-\overset{O}{\underset{\|}{C}}-CH_2CH_2-N\diagup\diagdown N-CH_2-\text{Ph}$$

| Compound No. | R | Melting Point (°C.) | Molecular Formula | Elemental Analysis Calculated (Found) | | |
|---|---|---|---|---|---|---|
| | | | | C | H | N |
| 1 | 1,2,3,4-tetrahydrocarbazol-6-yl (NH) | 165–167 | $C_{26}H_{33}N_3O \cdot 2C_4H_4O_4$ | 64.24 (64.07 | 6.50 6.57 | 6.61 6.40) |
| 2 | 2-(N-acetyl-N-(2,5-dimethylbenzyl)amino)phenoxy | 231–233 (decomp.) | $C_{29}H_{31}N_3O_3 \cdot 2HCl$ | 64.21 (64.08 | 6.13 5.98 | 7.75 7.69) |
| 3 | 2-(N-benzoyl-N-(2,5-dimethylbenzyl)amino)phenoxy | 208–211 | $C_{34}H_{33}N_3O_3 \cdot 2HCl$ | 67.55 (67.23 | 5.84 5.85 | 6.95 6.82) |

EXAMPLE 20

Using 1-(1,2,2a,3,4,5-hexahydrobenz[cd]indol6-yl)-3-[1-(phenylmethyl)piperizin-4-yl]-1-propanone as obtained in Example 4, the same procedure as in Example 8 was followed to yield the compounds listed in Table 57.

EXAMPLE 21

8-[3-(4-Formyl-1-piperazinyl)-1-oxopropyl]-5,6-dihydro-4H-pyroro[3,2,1-ij]quinolin-2(1H)-one

TABLE 57

(structure: tetrahydronaphthalenone with piperidine-N-benzyl side chain, N–R substituent)

| Comp. No. | R | Melting Point (°C.) | Molecular Formula | Elemental Analysis Calculated (Found) | | |
|---|---|---|---|---|---|---|
| | | | | C | H | N |
| 1 | COCH₂CH₃ | 140–142 | $C_{29}H_{36}N_2O_2 \cdot C_4H_4O_4$ | 70.69 (70.46 | 7.19 7.21 | 5.00 4.97) |
| 2 | COPh | Amorphous | $C_{33}H_{36}N_2O_2 \cdot C_4H_4O_4$ | 73.00 (72.95 | 6.62 6.64 | 4.60 4.53) |

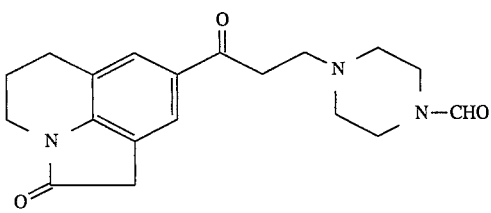

By the same procedure as used in Example 1, 13.8 g of 8-(3-chloropropyonyl)-5,6-dihydro-4 H-pyroro[3,2,1-ij]quinolin-2(1H)-one described as compound 2 in Reference Example 6, and 7.8 g of 1-piperazine-carboxyaldehyde were reacted to yield 11.0 g of the title compound as a colorless powder having a melting point of 143°–147° C.

Elemental analysis (for $C_{19}H_{23}N_3O_3$). Calculated: C, 66.84; H, 6.79; N, 12.31. Found: C, 66.69; H, 6.79; N, 12.07

EXAMPLE 22

8-[3-(1-Piperazinyl)-1-oxopropyl]-5,6-dihydro-4H-pyroro[3,2,1-ij]quinolin-2(1H)-one

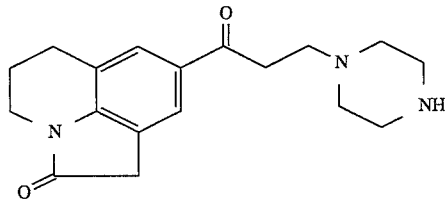

To 30 ml of methanol containing 9.0 g of 8-[3-(4-formyl-1-piperazinyl)-1-oxopropyl]-5,6-dihydro-4H-pyroro[3,2,1-ij]quinolin-2(1H)-one obtained in Example 21, 10 ml of conc. hydrochloric acid was added and stirred at room temperature for 14 hours. The solvent was evaporated under reduced pressure. The residual aqueous solution was washed with ethyl acetate, and adjusted to about pH 11 by addition of a sodium hydroxide aqueous solution for extraction with dichloromethane. The extract was dried over anhydrous sodium sulfate, and the solvent was evaporated under reduced pressure to yield 6.3 g of the title compound as an amorphous powder.

Elemental analysis (for $C_{18}H_{23}N_3O_2$). Calculated: C, 68.98; H, 7.40; N, 13.41. Found: C, 69.02; H, 7.38; N, 13.25

EXAMPLE 23

8-[3-[4-[(2-Methylphenyl)methyl]-1-piperazinyl]-1-oxopropyl]-5,6-dihydro-4 H-pyroro[3,2,1-ij]quinolin-2(1H)-one Dihydrochloride

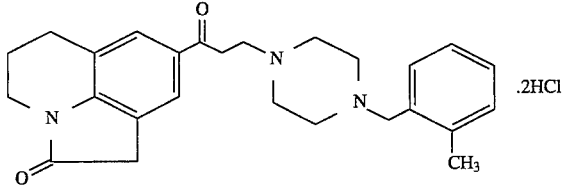

In 10 ml of dichloromethane, 0.34 g of 8-[3-(1-piperazinyl)-1-oxopropyl]-5,6-dihydro-4 H-pyroro[3,2,1-ij]quinolin-2(1H)-one obtained in Example 22 and 0.19 mg of 2-methylbenzyl bromide were suspended; the suspension was stirred at room temperature for six hours. After evaporation of the solvent, the residue was dissolved in a 10% hydrochloric acid aqueous solution and washed with ethyl acetate. The aqueous phase was adjusted to pH 11 by addition of a sodium hydroxide aqueous solution for extraction with dichloromethane. The extract was dried over anhydrous sodium sulfate, and the solvent was evaporated under reduced pressure. The residue was then purified by silica gel column chromatography (developing solvent: ethyl acetate-methanol=10:1 (v/v)) to yield 0.32 g of the colorless oily title compound in a free form. To this oily substance, 0.5 ml of 4N methanolic hydrochloric acid was added, followed by evaporation of the solvent. The title compound (as dihydrochloride) was thus obtained, in a yield of 0.34 g, as colorless crystals having a melting point of 205°–208° C.

Elemental analysis (for $C_{26}H_{31}N_3O_2 \cdot 2HCl \cdot H_2O$). Calculated: C, 61.41; H, 6.94; N, 8.26. Found: C, 61.64; H, 6.76; N, 8.25

EXAMPLE 24

8-[3-(4-Formyl-1-piperazinyl)-1-oxopropyl]-1,2,5,6-tetrahydro-4H-pyroro[3,2,1-ij]quinolin-4-one

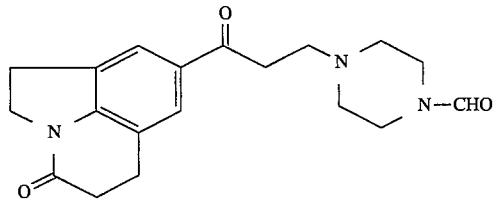

By the same procedure as used in Example 1, 20.0 g of 8-(3-chloropropionyl)-1,2,5,6-tetrahydro-4 H-pyroro[3,2,1-ij]quinolin-4-one, described as compound 1 in Example 6, and 11.4 g of 1-piperazine carboxyaldehyde were reacted to yield 20.4 g of the title compound as a colorless powder.

Elemental analysis (for $C_{19}H_{23}N_3O_3$). Calculated: C, 66.84; H, 6.79; N, 12.31. Found: C, 66.79; H, 6.58; N, 12.05

EXAMPLE 25

8-[3-(1-Piperazinyl)-1-oxopropyl]-1,2,5,6-tetrahydro-4H-pyroro[3,2,1-ij]quinolin-4-one

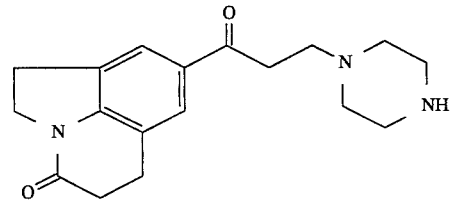

Of 8-[3-(4-formyl-1-piperazinyl)-1-oxopropyl]-1,2,5,6-tetrahydro-4H-pyroro[3,2,1-ij]quinolin-4-one obtained in Example 24, 20 g was reacted by the same procedure as used in Example 22 to yield 14.0 g of the title compound as a colorless powder.

Elemental analysis (for $C_{18}H_{23}N_3O_2$). Calculated: C, 68.98; H, 7.40; N, 13.41. Found: C, 68.69; H, 7.29; N, 13.27

EXAMPLE 26

8-[3-(1-Methoxycarbonyl-4-piperidinyl)-1-oxo-propyl]-1,2,5,6-tetrahydro-4 H-pyroro[3,2,1-ij]quinolin-4-one

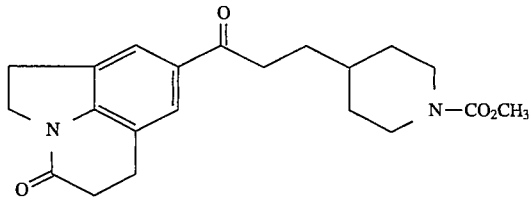

To 109 ml of thionyl chloride, 65.6 g of 3-(1-methoxycarbonyl-4-piperidinyl)propionic acid obtained in Example 7 was added in small portions at 0°–5° C. The obtained solution was stirred at 0°–5° C. for 20 minutes. After the thionyl chloride was evaporated under reduced pressure, the residue and 43.3 g of 1,2,5,6-tetrahydro-4H-pyroro[3,2,1-ij]quinolin-4-one were reacted by the same procedure as in Example 2 to yield 34.0 g of the title compound as colorless crystals having a melting point of 139°–140° C.

Elemental analysis (for $C_{21}H_{26}N_2O_4$). Calculated: C, 68.09; H, 7.07; N, 7.56. Found: C, 68.21; H, 7.01; N, 7.29

EXAMPLE 27

8-[3-(4-Piperidinyl)-1-oxopropyl]-1,2,5,6-tetrahydro-4H-pyroro[3,2,1-ij]quinolin-4-one

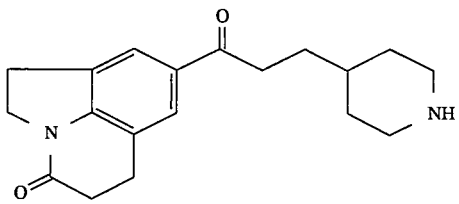

In a mixture of 200 ml of methanol and 400 ml of conc. hydrochloric acid, 34.0 g of 8-[3-(1-methoxycarbonyl-4-piperidinyl)-1-oxopropyl]-1,2,5,6-tetrahydro-4 H-pyroro[3,2,1-ij]quinolin-4-one obtained in Example 26 was dissolved; the solution was stirred for 16 hours under refluxing conditions. After cooling, the methanol was evaporated under reduced pressure. The residue, adjusted to pH 8–9 by addition of a 50% sodium hydroxide aqueous solution, was extracted twice with 500 ml of dichloromethane each time. The extracts were dried over anhydrous sodium sulfate, and the solvent was evaporated under reduced pressure. The obtained residue was crystallized from diethyl ether-ethyl acetate to yield 28.3 g of the title compound as colorless crystals having a melting point of 114°–116° C.

Elemental analysis (for $C_{19}H_{24}N_2O_2$). Calculated: C, 73.05; H, 7.74; N, 8.97. Found: C, 73.21; H, 7.65; N, 8.99

EXAMPLE 28

8-[3-(1-Methoxycarbonyl-4-piperidinyl)-1-oxo-propyl]-5,6-dihydro-4H-pyroro[3,2,1-ij]quinolin-2(1H)-one

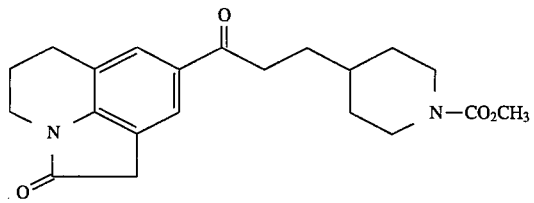

By the same procedure as in Example 26, 3-(1-methoxycarbonyl-4-piperidinyl)propionic acid obtained in Example 7 and well-known 5,6-dihydro-4H-pyroro[3,2,1-ij]quinolin-2(1H)-one were reacted to yield the title compound as colorless crystals having a melting point of 140°–141° C.

Elemental analysis (for $C_{21}H_{26}N_2O_4$). Calculated: C, 68.09; H, 7.07; N, 7.56. Found: C, 68.00; H, 7.12; N, 7.73

EXAMPLE 29

8-[3-(4-Piperidinyl)-1-oxopropyl]-5,6-dihydro-4H-pyroro[3,2,1-ij]quinolin-2 (1H)-one

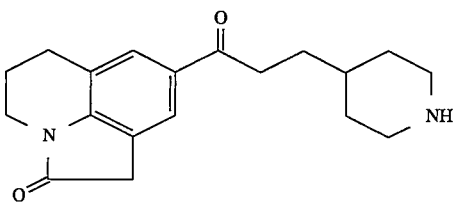

By the same procedure as in Example 27, 8-[3-(1-methoxycarbonyl-4-piperidinyl)-1-oxopropyl]-5,6-dihydro-4H-pyroro[3,2,1-ij]quinolin-2(1H)-one obtained in Example 28 was reacted to yield the title compound as a colorless oily substance.

Elemental analysis (for $C_{19}H_{24}N_2O_2$). Calculated: C, 73.05; H, 7.74; N, 8.97. Found: C, 73.10; H, 7.58; N, 8.73

EXAMPLE 30

Using the compound as obtained in Example 22 or 25, the same procedure as in Example 23 was followed to yield the compounds listed in Table 58–Table 63, Table 67 and Table 68 (method A). Using the compound as obtained in Example 27 or 29, the same procedure as in Example 13 was followed to yield the compounds listed in Table 62–Table 69 (method B).

TABLE 58

Ar—C(=O)—CH₂CH₂—Z[N(CH₂CH₂)₂]N—CH₂—C₆H₄—X

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 1 | A | 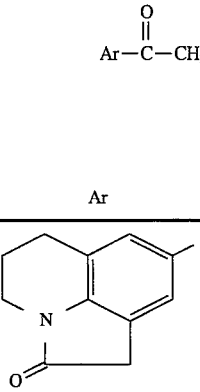 | N | 3-$CH_3$ | 210–214 | $C_{26}H_{31}N_3O_2$·2HCl·$H_2O$ | 61.41 (61.63 | 6.94 6.83 | 8.26 8.43) |
| 2 | A | 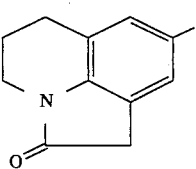 | N | 4-$CH_3$ | 216–218 | $C_{26}H_{31}N_3O_2$·2HCl·1/2$H_2O$ | 62.52 (62.25 | 6.86 6.66 | 8.41 8.12) |
| 3 | A | 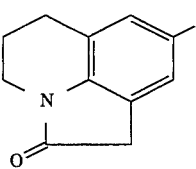 | N | 2-Cl | 218–220 | $C_{25}H_{28}ClN_3O_2$·2HCl·2$H_2O$ | 54.90 (55.08 | 6.27 6.20 | 7.68 7.56) |
| 4 | A | 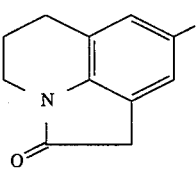 | N | 3-Cl | 215–217 | $C_{25}H_{28}ClN_3O_2$·2HCl·$H_2O$ | 56.77 (56.73 | 6.10 5.97 | 7.94 7.87) |
| 5 | A | 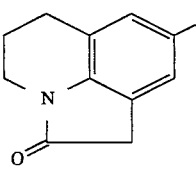 | N | 4-Cl | 209–213 | $C_{25}H_{28}ClN_3O_2$·2HCl·$H_2O$ | 56.77 (57.07 | 6.10 5.94 | 7.94 7.69) |
| 6 | A | 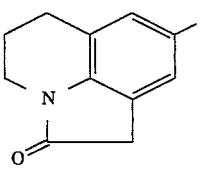 | N | 2-$C_2H_5$ | 217–220 | $C_{27}H_{33}N_3O_2$·2HCl·$H_2O$ | 62.06 (62.16 | 7.14 6.91 | 8.04 8.00) |

TABLE 59

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 7 | A | 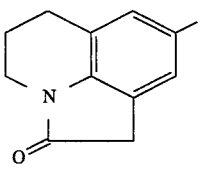 | N | 4-$C_2H_5$ | 205–209 | $C_{27}H_{33}N_3O_2$·2HCl·$H_2O$ | 62.06 (62.30 | 7.14 7.01 | 8.04 8.22) |

TABLE 59-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 8 | A | 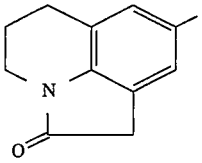 | N | 3,4-(CH₃)₂ | 207–209 | C₂₇H₃₃N₃O₂. 2HCl.H₂O | 62.06 (61.85 | 7.14 6.92 | 8.04 7.90) |
| 9 | A | 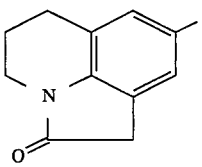 | N | 2,5-(CH₃)₂ | 185–190 | C₂₇H₃₃N₃O₂. 2HCl.H₂O | 62.06 (62.14 | 7.14 7.05 | 8.04 7.92) |
| 10 | A | 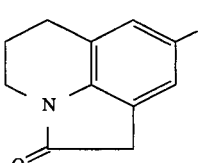 | N | 2-F | 215–217 | C₂₅H₂₈FN₃O₂. 2HCl.1/2H₂O | 59.64 (59.41 | 6.21 6.23 | 8.35 8.06) |
| 11 | A | 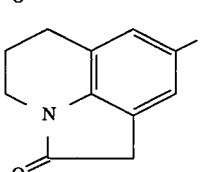 | N | 3-F | 228–230 | C₂₅H₂₈FN₃O₂. 2HCl.1/2H₂O | 59.64 (59.85 | 6.21 6.11 | 8.35 8.23) |
| 12 | A | 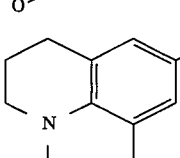 | N | 4-F | 220–223 | C₂₅H₂₈FN₃O₂. 2HCl.1/2H₂O | 59.64 (59.45 | 6.21 6.10 | 8.35 8.11) |
| 13 | A | 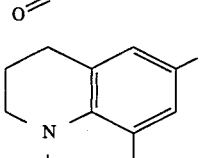 | N | 2-OCH₃ | 222–225 | C₂₆H₃₁N₃O₃. 2HCl.3/2H₂O | 58.54 (58.35 | 6.80 6.54 | 7.88 7.66) |

TABLE 60

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 14 | A | 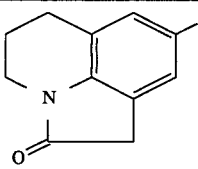 | N | 3-OCH₃ | 203–207 | C₂₆H₃₁N₃O₃. 2HCl.H₂O | 59.54 (59.69 | 6.73 6.66 | 8.01 7.89) |
| 15 | A | 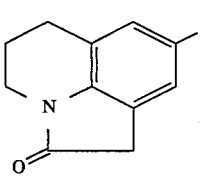 | N | 4-OCH₃ | 209–212 | C₂₆H₃₁N₃O₃. 2HCl.1/2H₂O | 60.58 (60.38 | 6.65 6.47 | 8.15 7.99) |

TABLE 60-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 16 | A | 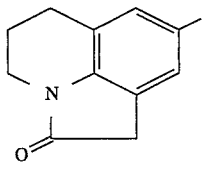 | N | 2-OH | 188–190 | $C_{25}H_{29}N_3O_3 \cdot 2HCl \cdot H_2O$ | 58.82 (58.97 | 6.52 6.62 | 8.23 8.04) |
| 17 | A | 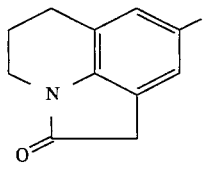 | N | 4-OCH$_2$Ph | 134–138 | $C_{32}H_{35}N_3O_3$ | 75.41 (75.37 | 6.92 6.99 | 8.25 7.98) |
| 18 | A | 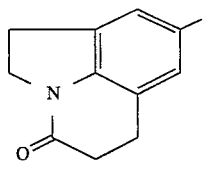 | N | 2-CH$_3$ | 220–222 | $C_{26}H_{31}N_3O_2 \cdot 2HCl \cdot 4H_2O$ | 55.51 (55.31 | 7.35 7.10 | 7.47 7.28) |
| 19 | A | 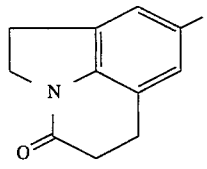 | N | 3-CH$_3$ | 232–238 | $C_{26}H_{31}N_3O_2 \cdot 2HCl \cdot 1/2H_2O$ | 62.52 (62.25 | 6.86 6.71 | 8.41 8.21) |
| 20 | A | 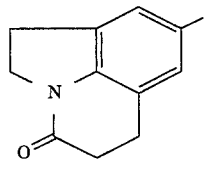 | N | 4-CH$_3$ | 243–244 | $C_{26}H_{31}N_3O_2 \cdot 2HCl \cdot H_2O$ | 61.41 (61.36 | 6.94 6.84 | 8.26 8.07) |

TABLE 61

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 21 | A | 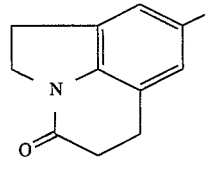 | N | 2-Cl | 226–230 | $C_{25}H_{28}ClN_3O_2 \cdot 2HCl \cdot 5/2H_2O$ | 54.01 (53.88 | 6.35 6.09 | 7.56 7.51) |
| 22 | A | 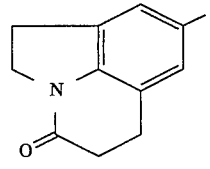 | N | 3-Cl | 227–234 | $C_{25}H_{28}ClN_3O_2 \cdot 2HCl \cdot 1/2H_2O$ | 57.76 (57.87 | 6.01 6.23 | 8.08 7.85) |

TABLE 61-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 23 | A | 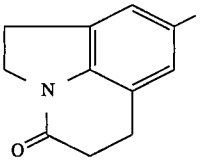 | N | 4-Cl | 228–231 | $C_{25}H_{28}ClN_3O_2$·2HCl·3/2H$_2$O | 55.82 (55.96 | 6.18 5.91 | 7.81 8.01) |
| 24 | A | 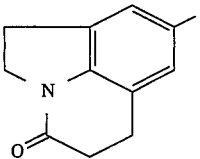 | N | 2-F | 232–233 | $C_{25}H_{28}FN_3O_2$·2HCl·H$_2$O | 58.60 (58.48 | 6.29 6.20 | 8.20 8.04) |
| 25 | A | 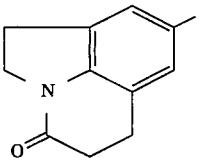 | N | 3-F | 234–238 | $C_{25}H_{28}FN_3O_2$·2HCl·1/2H$_2$O | 59.64 (59.72 | 6.21 6.09 | 8.35 8.39) |
| 26 | A | 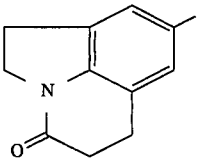 | N | 4-F | 228–232 | $C_{25}H_{28}FN_3O_2$·2HCl·H$_2$O | 58.60 (58.72 | 6.29 6.04 | 8.20 8.00) |
| 27 | A | 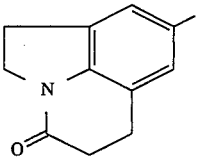 | N | 2,5-(CH$_3$)$_2$ | 223–225 | $C_{27}H_{33}N_3O_2$·2HCl·1/2H$_2$O | 63.15 (62.97 | 7.07 6.89 | 8.18 7.97) |

TABLE 62

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 28 | A | | N | 3,4-(CH$_3$)$_2$ | 244–246 | $C_{27}H_{33}N_3O_2$·2HCl·1/2H$_2$O | 63.15 (62.99 | 7.07 7.04 | 8.18 7.93) |
| 29 | A | | N | 3-NO$_2$ | 202–203 | $C_{25}H_{28}N_4O_4$·2HCl | 57.59 (57.47 | 5.80 6.01 | 10.74 10.62) |
| 30 | A | | N | 4-NO$_2$ | 158–160 | $C_{25}H_{28}N_4O_4$·2HCl·3H$_2$O | 52.18 (52.31 | 6.31 6.19 | 9.74 9.59) |

TABLE 62-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 31 | A | (tricyclic Ar) | N | 3-OCH$_3$ | 221.5–223 | C$_{26}$H$_{31}$N$_3$O$_3$·2HCl·1/2H$_2$O | 60.58 (60.44 | 6.65 6.59 | 8.15 8.03) |
| 32 | A | (tricyclic Ar) | N | 2-OCH$_3$ | 203–207 | C$_{26}$H$_{31}$N$_3$O$_3$·2HCl·H$_2$O | 59.54 (59.70 | 6.73 6.57 | 8.01 7.85) |
| 33 | A | (tricyclic Ar) | N | 4-OCH$_3$ | 219–222 | C$_{26}$H$_{31}$N$_3$O$_3$·2HCl·1/4H$_2$O | 61.12 (61.01 | 6.61 6.60 | 8.22 8.24) |
| 34 | B | (tricyclic Ar) | CH | — | 244–246 | C$_{26}$H$_{30}$N$_2$O$_2$·HCl·1/2H$_2$O | 69.71 (69.70 | 6.97 7.09 | 6.25 6.11) |

TABLE 63

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 35 | A | (tricyclic Ar) | N | 3-NO$_2$ | 198–200 | C$_{25}$H$_{28}$N$_4$O$_4$·2HCl·H$_2$O | 55.66 (55.39 | 5.98 6.01 | 10.39 10.22) |
| 36 | A | (tricyclic Ar) | N | 4-NO$_2$ | 207–211 | C$_{25}$H$_{28}$N$_4$O$_4$·2HCl·1/4H$_2$O | 57.09 (56.95 | 5.84 5.92 | 10.65 10.44) |
| 37 | B | (tricyclic Ar) | CH | 3,4-OCH$_2$O— | amorphous powder | C$_{27}$H$_{30}$N$_2$O$_4$·HCl·3/2H$_2$O | 63.58 (63.56 | 6.72 6.60 | 5.49 5.23) |

TABLE 63-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 38 | B | (tricyclic Ar with N-C(=O)) | CH | — | amorphous powder | $C_{26}H_{30}N_2O_2$·HCl·1/4$H_2O$ | 70.41 (70.16 | 7.15 7.16 | 6.31 6.10) |
| 39 | B | (tricyclic Ar with N-C(=O)) | CH | 2-F | amorphous powder | $C_{26}H_{29}FN_2O_2$·HCl·5/2$H_2O$ | 62.21 (62.17 | 7.03 6.73 | 5.58 5.40) |
| 40 | B | (tricyclic Ar with N-C(=O)) | CH | 3-F | amorphous powder | $C_{26}H_{29}FN_2O_2$·HCl·5/2$H_2O$ | 62.21 (61.72 | 7.03 6.53 | 5.58 5.57) |

TABLE 64

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 41 | B | (tricyclic Ar with N-C(=O)) | CH | 4-F | amorphous powder | $C_{26}H_{29}FN_2O_2$·HCl·2$H_2O$ | 63.34 (63.23 | 6.95 6.51 | 5.68 5.71) |
| 42 | B | (tricyclic Ar with N-C(=O)) | CH | 2-Cl | amorphous powder | $C_{26}H_{29}ClN_2O_2$·HCl·5/2$H_2O$ | 60.23 (60.62 | 6.80 6.45 | 5.40 5.38) |
| 43 | B | (tricyclic Ar with N-C(=O)) | CH | 3-Cl | amorphous powder | $C_{26}H_{29}ClN_2O_2$·HCl·3/2$H_2O$ | 62.40 (62.22 | 6.65 6.58 | 5.60 5.31) |
| 44 | B | (tricyclic Ar with N-C(=O)) | CH | 4-Cl | amorphous powder | $C_{26}H_{29}ClN_2O_2$·HCl·$H_2O$ | 63.54 (63.26 | 6.56 6.53 | 5.70 5.54) |
| 45 | B | (tricyclic Ar with N-C(=O)) | CH | 2-$CH_3$ | amorphous powder | $C_{27}H_{32}N_2O_2$·HCl·3/2$H_2O$ | 67.56 (67.59 | 7.56 7.78 | 5.84 5.85) |

TABLE 64-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 46 | B | 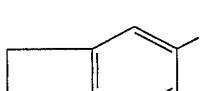 | CH | 3-CH$_3$ | amorphous powder | C$_{27}$H$_{32}$N$_2$O$_2$. HCl.3/2H$_2$O | 67.56 (67.79 | 7.56 7.60 | 5.84 5.65) |
| 47 | B | 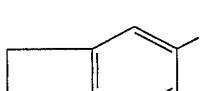 | CH | 4-CH$_3$ | amorphous powder | C$_{27}$N$_{32}$N$_2$O$_2$. HCl.3/2H$_2$O | 67.56 (67.74 | 7.56 7.56 | 5.84 5.78) |

TABLE 65

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 48 | B | 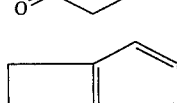 | CH | 2-OCH$_3$ | amorphous powder | C$_{27}$H$_{32}$N$_2$O$_3$. HCl | 69.14 (69.02) | 7.09 6.89 | 5.97 6.01) |
| 49 | B | 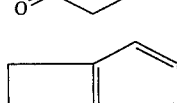 | CH | 3-OCH$_3$ | amorphous powder | C$_{27}$H$_{32}$N$_2$O$_3$. HCl.3/2H$_2$O | 65.38 (65.01 | 7.32 7.39 | 5.65 5.51) |
| 50 | B | 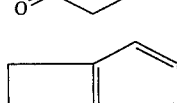 | CH | 4-OCH$_3$ | amorphous powder | C$_{27}$H$_{32}$N$_2$O$_3$. HCl.2H$_2$O | 64.21 (63.98 | 7.38 7.42 | 5.55 5.50) |
| 51 | B | 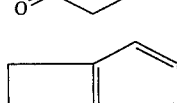 | CH | 2-NO$_2$ | amorphous powder | C$_{26}$H$_{29}$N$_3$O$_4$. HCl.5/2H$_2$O | 59.03 (58.88 | 6.67 6.75 | 7.94 8.01) |
| 52 | B | 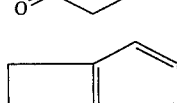 | CH | 3-NO$_2$ | amorphous powder | C$_{26}$H$_{29}$N$_3$O$_4$. HCl.2H$_2$O | 60.17 (60.20 | 6.41 6.17 | 8.10 7.96) |

TABLE 65-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 53 | B | 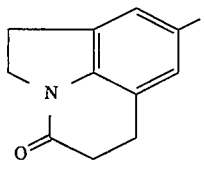 | CH | 4-$NO_2$ | amorphous powder | $C_{26}H_{29}N_3O_4$·HCl | 64.66 (64.52 | 6.05 5.97 | 8.70 8.64) |
| 54 | B | 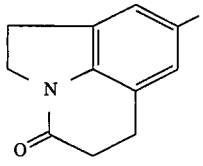 | CH | 2,4-$(CH_3)_2$ | amorphous powder | $C_{28}H_{34}N_2O_2$·HCl·1/2$H_2O$ | 70.64 (70.30 | 7.83 7.62 | 5.88 6.09) |

TABLE 66

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 55 | B | 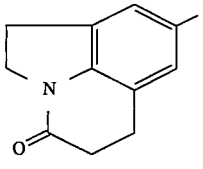 | CH | 3,5-$(CH_3)_2$ | amorphous powder | $C_{28}H_{34}N_2O_2$·HCl·$H_2O$ | 69.33 (69.38 | 7.69 7.77 | 5.78 5.82) |
| 56 | B | 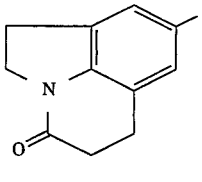 | CH | 2,5-$(CH_3)_2$ | amorphous powder | $C_{28}H_{34}N_2O_2$·HCl·2$H_2O$ | 66.85 (67.14 | 7.81 7.46 | 5.57 5.43) |
| 57 | B | 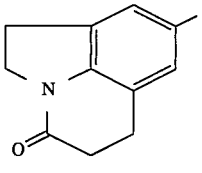 | CH | 4-$C_2H_5$ | amorphous powder | $C_{28}H_{34}N_2O_2$·HCl·$H_2O$ | 69.33 (69.23 | 7.69 7.60 | 5.78 5.49) |
| 58 | B | 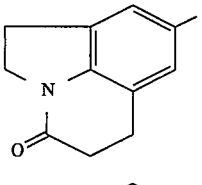 | CH | 2-OH | amorphous powder | $C_{26}H_{30}N_2O_3$·HCl·$H_2O$ | 66.02 (65.97 | 7.03 6.91 | 5.92 5.72) |
| 59 | B | 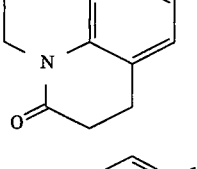 | CH | 3-OH | amorphous powder | $C_{26}H_{30}N_2O_3$·HCl·3/2$H_2O$ | 64.79 (64.67 | 7.11 6.82 | 5.81 5.65) |
| 60 | B | 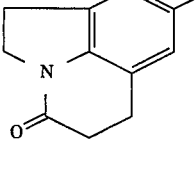 | CH | 4-OH | amorphous powder | $C_{26}H_{30}N_2O_3$·HCl·2$H_2O$ | 63.60 (63.56 | 7.18 7.03 | 5.71 5.91) |

TABLE 66-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 61 | B | (pyrrolo-quinolinone) | CH | 2-CN | amorphous powder | $C_{27}H_{29}N_3O_2 \cdot$ HCl.5/2H$_2$O | 63.71 (64.00 | 6.73 6.54 | 8.25 8.23) |

TABLE 67

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 62 | B | (pyrrolo-quinolinone) | CH | 3-CN | amorphous powder | $C_{27}H_{29}N_3O_2 \cdot$ HCl.2H$_2$O | 64.85 (64.92 | 6.85 6.88 | 8.40 8.17) |
| 63 | B | (pyrrolo-quinolinone) | CH | 4-CN | amorphous powder | $C_{27}H_{29}N_3O_2 \cdot$ HCl.H$_2$O | 67.28 (67.31 | 6.69 6.78 | 8.72 8.80) |
| 64 | B | (pyrrolo-quinolinone) | CH | 3,4-(OCH$_3$)$_2$ | amorphous powder | $C_{28}H_{34}N_2O_4 \cdot$ HCl | 67.39 (67.14 | 7.07 7.10 | 5.61 5.54) |
| 65 | B | (pyrrolo-quinolinone) | CH | 2,3-(OCH$_3$)$_2$ | amorphous powder | $C_{28}H_{34}N_2O_4 \cdot$ HCl.3/2H$_2$O | 63.93 63.79 | 7.28 7.21 | 5.33 5.35) |
| 66 | A | (pyrrolo-quinolinone) | N | 2,3-Cl$_2$ | 229–230 | $C_{25}H_{27}Cl_2N_3O_2 \cdot$ 2HCl.H$_2$O | 53.30 (53.08 | 5.55 5.44 | 7.46 7.49) |
| 67 | A | (pyrrolo-quinolinone) | N | 2,4-Cl$_2$ | 219–221 | $C_{25}H_{27}Cl_2N_3O_2 \cdot$ 2HCl.H$_2$O | 53.30 (53.03 | 5.55 5.49 | 7.46 7.33) |

TABLE 67-continued

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 68 | A | (structure) | N | 2,6-$Cl_2$ | 209–213 | $C_{25}H_{27}Cl_2N_3O_2$·2HCl·2$H_2O$ | 51.65 (51.52 | 5.72 5.63 | 7.23 7.07) |

TABLE 68

| Comp. No. | Method | Ar | Z | X | m.p. (°C.) | Molecular Formula | Elemental Analysis Calcd. (Found) | | |
|---|---|---|---|---|---|---|---|---|---|
| | | | | | | | C | H | N |
| 69 | A | (structure) | N | 3,4-$Cl_2$ | 222–224 | $C_{25}H_{27}Cl_2N_3O_2$·2HCl·1/2$H_2O$ | 54.17 (54.46 | 5.45 5.52 | 7.58 7.55) |
| 70 | A | (structure) | N | 2-$NO_2$ | 216–221 | $C_{25}H_{28}N_4O_4$·2HCl·3/2$H_2O$ | 54.75 (54.89 | 6.06 5.92 | 10.22 10.00) |
| 71 | A | (structure) | N | 2-OH | 229–231 | $C_{25}H_{29}N_3O_3$·2HCl·3$H_2O$ | 54.95 (55.02 | 6.82 6.13 | 7.69 7.57) |
| 72 | B | (structure) | CH | 3-$OCH_3$ | amorphous powder | $C_{27}H_{32}N_2O_3$·HCl·1/2$H_2O$ | 67.84 (67.56 | 7.17 7.05 | 5.86 5.80) |
| 73 | B | (structure) | CH | 4-$OCH_3$ | amorphous powder | $C_{27}H_{32}N_2O_3$·HCl·3/4$H_2O$ | 67.21 (67.11 | 7.21 6.95 | 5.81 5.95) |
| 74 | B | (structure) | CH | 3,4-$(OCH_3)_2$ | amorphous powder | $C_{28}H_{34}N_2O_4$·HCl·2$H_2O$ | 62.85 (62.77 | 7.35 7.61 | 5.24 5.31) |

TABLE 68-continued

| Comp. No. | Method | Ar | Z | X | m.p. (°C.) | Molecular Formula | Elemental Analysis Calcd. (Found) C | H | N |
|---|---|---|---|---|---|---|---|---|---|
| 75 | B | (tricyclic structure) | CH | 4-$C_2H_5$ | amorphous powder | $C_{28}H_{34}N_2O_2 \cdot HCl \cdot H_2O$ | 69.33 (69.50 | 7.69 7.48 | 5.78 5.80) |

TABLE 69

| Comp. No. | Method | Ar | Z | X | m.p. (°C.) | Molecular Formula | Elemental Analysis Calcd. (Found) C | H | N |
|---|---|---|---|---|---|---|---|---|---|
| 76 | B | (tricyclic structure) | CH | 3,5-$(CH_3)_2$ | amorphous powder | $C_{28}H_{34}N_2O_2 \cdot HCl \cdot 2H_2O$ | 66.85 (66.79 | 7.81 7.58 | 5.57 5.53) |

EXAMPLE 31

Using the compound as obtained in Reference Example 6 or 8, the same procedure as in Example 1 was followed to yield the compounds listed in Table 70 and Table 71.

TABLE 70

$$Ar-\overset{O}{\underset{\|}{C}}-(CH_2)_n-NR^1R^2$$

| Comp. No. | Ar | n | $NR^1R^2$ | m.p. (°C.) | Molecular Formula | Elemental Analysis Calcd. (Found) C | H | N |
|---|---|---|---|---|---|---|---|---|
| 1 | (tricyclic structure) | 2 | $-N\diagup\diagdown N-CH_2-$(benzodioxole) | 215–217 | $C_{26}H_{29}N_3O_4 \cdot 2HCl \cdot 1/2H_2O$ | 58.98 (59.18 | 6.09 6.03 | 7.94 7.95) |
| 2 | (tricyclic structure) | 2 | $-N\diagup\diagdown$-$CH_2Ph$ | 218–220 | $C_{26}H_{30}N_2O_2 \cdot HCl \cdot 1/2H_2O$ | 69.71 (69.97 | 7.20 7.10 | 6.23 6.30) |
| 3 | (tricyclic structure) | 2 | $-N\diagup\diagdown N-CH_2-$(benzodioxole) | 230–235 | $C_{26}H_{29}N_3O_4 \cdot 2HCl \cdot 3/4H_2O$ | 58.48 (58.36 | 6.13 6.08 | 7.87 7.80) |

TABLE 70-continued $$Ar-\overset{O}{\underset{\|}{C}}-(CH_2)_n-NR^1R^2$$

| Comp. No. | Ar | n | NR¹R² | m.p. (°C.) | Molecular Formula | Elemental Analysis Calcd. (Found) | | |
|---|---|---|---|---|---|---|---|---|
| | | | | | | C | H | N |
| 4 | [tricyclic structure with N, C=O, methyl] | 2 | −N⌐⌐−CH₂Ph (piperidinyl-CH₂Ph) | 241–243 | $C_{26}H_{30}N_2O_2 \cdot HCl \cdot 1/4H_2O$ | 70.41 (70.58 | 7.16 7.18 | 6.32 6.39) |
| 5 | [tricyclic structure with N, C=O, methyl] | 2 | −N⌐⌐−C(O)Ph (piperidinyl-C(O)Ph) | 236–237 | $C_{26}H_{28}N_2O_3 \cdot HCl \cdot 1/4H_2O$ | 68.26 (68.28 | 6.50 6.52 | 6.12 5.99) |
| 6 | [tricyclic structure with N, C=O, methyl] | 2 | −N⌐⌐N−C(O)Ph (piperazinyl-C(O)Ph) | 204–208 | $C_{25}H_{27}N_3O_3 \cdot HCl \cdot 1/2H_2O$ | 64.86 (64.65 | 6.31 6.50 | 9.08 8.80) |

TABLE 71

$$Ar-\overset{O}{\underset{\|}{C}}-(CH_2)_n-NR^1R^2$$

| Comp. No. | Ar | n | NR¹R² | m.p. (°C.) | Molecular Formula | Elemental Analysis Calcd. (Found) | | |
|---|---|---|---|---|---|---|---|---|
| | | | | | | C | H | N |
| 7 | [tricyclic structure with N, C=O, methyl] | 3 | −N⌐⌐N−CH₂Ph (piperazinyl-CH₂Ph) | 201–205 | $C_{26}H_{31}N_3O_2 \cdot 2HCl \cdot 3/2H_2O$ | 60.35 (60.66 | 7.01 7.03 | 8.12 8.12) |
| 8 | [tricyclic structure with N, C=O, methyl] | 3 | −N⌐⌐N−Ph (piperazinyl-Ph) | 234–236 | $C_{25}H_{29}N_3O_2 \cdot 2HCl \cdot 1/2H_2O$ | 61.85 (62.14 | 6.64 6.57 | 8.66 8.65) |
| 9 | [tricyclic structure with N, C=O, methyl] | 3 | −N⌐⌐N−cyclohexyl (piperazinyl-cyclohexyl) | 226–229 | $C_{25}H_{35}N_3O_2 \cdot 2HCl \cdot 3H_2O$ | 55.97 (56.02 | 8.08 8.10 | 7.83 7.84) |
| 10 | [tricyclic structure with N, C=O, methyl] | 3 | −N⌐⌐−Ph (piperidinyl-Ph) | 245–250 | $C_{26}H_{30}N_2O_2 \cdot HCl \cdot 1/2H_2O$ | 69.71 (69.66 | 7.20 7.18 | 6.25 6.12) |

TABLE 71-continued $$Ar-\overset{O}{\underset{\|}{C}}-(CH_2)_n-NR^1R^2$$

| Comp. No. | Ar | n | NR¹R² | m.p. (°C.) | Molecular Formula | Elemental Analysis Calcd. (Found) | | |
|---|---|---|---|---|---|---|---|---|
| | | | | | | C | H | N |
| 11 | (dibenzazepine with N-CHO) | 2 | -N(piperidine)-CH₂Ph | amorphous powder | $C_{30}H_{32}N_2O_2$·HCl·3/2H₂O | 69.82 (69.78 | 7.03 6.92 | 5.43 5.16) |

EXAMPLE 32

Using the compound as obtained in Example 17, the same procedure as in Example 2 was followed to yield the compounds listed in Table 72.

TABLE 72

$$Ar-\overset{O}{\underset{\|}{C}}-CH_2CH_2-N\diagup\diagdown N-CH_2-\text{Ph}$$

| Comp. No. | Ar | m.p. (°C.) | Molecular Formula | Elemental Analysis Calcd. (Found) | | |
|---|---|---|---|---|---|---|
| | | | | C | H | N |
| 1 | (biphenyl-CH₂-NH-CH₂-) | 184–187 | $C_{28}H_{31}N_3O$·3HCl·5/2H₂O | 57.98 (58.28 | 6.78 6.64 | 7.24 7.39) |
| 2 | (diphenylmethane-CH₂-NH-CH₂-) | 178–181 | $C_{28}H_{31}N_3O$·3HCl | 62.86 (62.61 | 6.41 6.45 | 7.86 7.78) |
| 3 | (diphenyl ether-CH₂-NH-CH₂-) | 178–183 | $C_{27}H_{29}N_3O_2$·3HCl·2H₂O | 56.60 (56.73 | 6.33 6.39 | 7.33 7.23) |
| 4 | (dibenzo-CH₂CH₂-NH-CH₂-) | amorphous powder | $C_{29}H_{33}N_3O$·3HCl·H₂O | 61.43 (61.54 | 6.76 6.61 | 7.41 7.14) |

EXAMPLE 33

1-(6,7-Dihydro-5H-dibenz[c,e]azepine-3-yl)-3-[4-(phenylmethyl)-1-piperidinyl]-1-propanone dihydrochloride

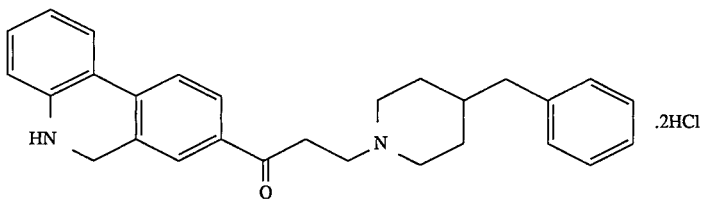

Using the compound No. 11 in Example 31, the same procedure as in Example 2 was followed to yield the title compound as an amorphous poweder.

Elemental analysis (for $C_{29}H_{32}N_2O \cdot 2HCl \cdot 2H_2O$): Calculated: C, 65.28; H, 7.18; N, 5.25. Found: C, 65.22; H, 7.08; N, 5.08

EXAMPLE 34

Using the compound as obtained in Example 32 or 33, the same procedure as in Example 6 (method A) or Example 8 (method B) was followed to yield the compounds listed in Table 73 and 74.

TABLE 73

$$Ar-\overset{O}{\underset{\|}{C}}-CH_2CH_2-NR^1R^2$$

| Comp. No. | Method | Ar | NR¹R² | m.p. (°C.) | Molecular Formula | Elemental Analysis Calcd. (Found) C | H | N |
|---|---|---|---|---|---|---|---|---|
| 1 | A | [dibenzazepine with N-CH₂Ph] | −N⌒N−CH₂Ph | 203–206 (decomp.) | $C_{35}H_{37}N_3O \cdot 3HCl \cdot 5/2H_2O$ | 62.73 (62.49 | 6.77 6.62 | 6.27 6.23) |
| 2 | A | [dibenzazepine with N-CH₂-C₆H₄-OCH₃] | −N⌒N−CH₂Ph | 193–196 (decomp.) | $C_{36}H_{39}N_3O_2 \cdot 3HCl$ | 66.00 (65.82 | 6.46 6.59 | 6.41 6.43) |
| 3 | B | [dibenzazepine with N-Ac] | −N⌒N−CH₂Ph | 149–152 | $C_{30}H_{33}N_3O_2 \cdot 2HCl \cdot 3H_2O$ | 60.60 (60.64 | 6.95 6.98 | 7.07 7.22) |

TABLE 73-continued $$Ar-\overset{\overset{O}{\|}}{C}-CH_2CH_2-NR^1R^2$$

| Comp. No. | Method | Ar | NR¹R² | m.p. (°C.) | Molecular Formula | Elemental Analysis Calcd. (Found) | | |
|---|---|---|---|---|---|---|---|---|
| | | | | | | C | H | N |
| 4 | B | [dibenzazepine with N-COPh] | −N⌒N−CH₂Ph | 151–161 | C₃₅H₃₅N₃O₂· 2HCl·2H₂O | 65.82 (66.11 | 6.47 6.46 | 6.58 6.28) |

TABLE 74

| Comp. No. | Method | Ar | NR¹R² | m.p. (°C.) | Molecular Formula | Elemental Analysis Calcd. (Found) | | |
|---|---|---|---|---|---|---|---|---|
| | | | | | | C | H | N |
| 5 | B | [dibenzazepine with N-CO-C₆H₄-OCH₃] | −N⌒N−CH₂Ph | 191–194 (decomp.) | C₃₆H₃₇N₃O₃· 2HCl | 68.35 (68.08 | 6.21 6.32 | 6.64 6.63) |
| 6 | B | [dibenzazepine with N-Ac] | −N⌒CH₂Ph | amorphous powder | C₃₁H₃₄N₂O₂· HCl | 74.01 (73.83 | 7.01 6.98 | 5.57 5.45) |
| 7 | A | [dibenzazepine with N-CH₂Ph] | −N⌒CH₂Ph | amorphous powder | C₃₆H₃₈N₂O· 2HCl | 71.39 (71.12 | 6.99 7.05 | 4.63 4.54) |
| 8 | B | [dibenzazepine with N-COPh] | −N⌒CH₂Ph | amorphous powder | C₃₆H₃₆N₂O₂· HCl·3/2H₂O | 73.02 (72.77 | 6.81 6.53 | 4.73 4.51) |

EXAMPLE 35

1-(10-Acetyl-10,11-dihydrodibenz[b,f][1,4]oxazepin-2-yl)-3[1-(phenylmethyl)-4-piperidinyl]-1-propanone Hydrochloride

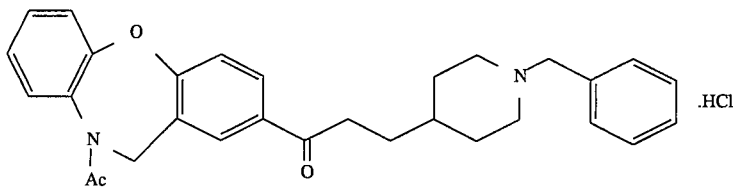

Using the known compound, 10-acetyl-10,11-dihydrodibenz[b,f][1,4]oxazepine, the same procedures as in Example 3 and then Example 4 were followed to yield the title compound as a colorless amorphous powder.

Elemental analysis (for $C_{30}H_{32}N_2O_3 \cdot HCl$): Calculated: C, 71.35; H, 6.59; N, 5.55. Found: C, 71.21; H, 6.63; N, 5.50

EXAMPLE 36

1-(10,11-Dihydrodibenz[b,f][1,4]oxazepin-2-yl)-3-[1-(phenylmethyl)-4-piperidinyl]-1-propanone Dihydrochloride

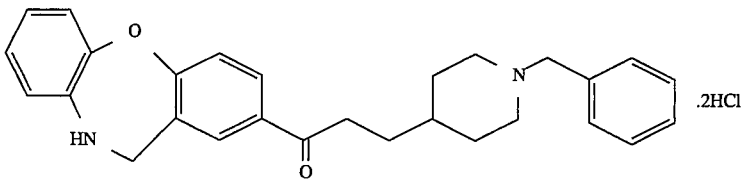

Using 1-(10-acetyl-10,11-dihydrodibenz[b,f][1,4]oxazepin-2-yl)-3-[1 -(phenylmethyl)-4-piperidinyl]-1-propanone hydrochloride obtained in Example 35, the same procedure as in Example 12 was followed to yield the title compound as colorless crystals having a melting point of 144°–147° C. (decomposition).

Elemental analysis (for $C_{28}H_{30}N_2O_2 \cdot 2HCl \cdot 3/2H_2O$): Calculated: C, 63.88; H, 6.70; N, 5.32. Found: C, 63.98; H, 6.48; N, 5.44

EXAMPLE 37

Using the known compounds, the same procedures as in Example 3 and then Example 6 were followed to yield the compounds listed in Table 75.

TABLE 75

$$Ar-\overset{O}{\underset{\|}{C}}-CH_2CH_2-\underset{\diagdown}{\diagup}\!\!\!\!\!\!\bigcirc\!\!\!\!\!\!\diagdown\!\!\!\!\!\!\diagup\!\!-N-CH_2-\bigcirc$$

| Comp. No. | Ar | m.p. (°C.) | Molecular Formula | Elemental Analysis Calcd. (Found) | | |
|---|---|---|---|---|---|---|
| | | | | C | H | N |
| 1 | (dibenzazepine with CH2Ph on N) | 171–173 | $C_{37}H_{40}N_2O \cdot C_4H_4O_4 \cdot 1/2H_2O$ | 75.32 (75.21 | 6.94 7.06 | 4.28 4.06) |
| 2 | (naphthalene bis-CH2 with PhCH2N) | amorphous powder | $C_{34}H_{36}N_2O \cdot 2C_4H_4O_4 \cdot H_2O$ | (68.28 (68.15 | 6.28 6.39 | 3.79 3.71) |

TABLE 75-continued

Ar—C(=O)—CH$_2$CH$_2$—[piperidine]—N—CH$_2$—[phenyl]

| Comp. No. | Ar | m.p. (°C.) | Molecular Formula | Elemental Analysis Calcd. (Found) C | H | N |
|---|---|---|---|---|---|---|
| 3 | [1,2,2a,3,4,5-hexahydrobenz[cd]indol-6-yl, NH] | amorphous powder | $C_{27}H_{34}N_2O \cdot 2C_4H_4O_4$ | 66.23 (66.18) | 6.67 (6.70) | 4.41 (4.40) |
| 4 | [1,2,2a,3,4,5-hexahydrobenz[cd]indol-6-yl, N-CH$_3$] | amorphous powder | $C_{28}H_{36}N_2O \cdot 2C_4H_4O_4$ | 66.65 (66.41) | 6.84 (6.59) | 4.32 (4.24) |
| 5 | [dibenzazepine/NH] | amorphous powder | $C_{30}H_{34}N_2O \cdot 2HCl \cdot H_2O$ | 68.04 (68.42) | 7.23 (7.62) | 5.29 (4.99) |

FORMULATION EXAMPLE 1

| | |
|---|---|
| (1) 1-(1,2,2a,3,4,5-hexahydrobenz[cd]indol-6-yl)-3-[1-(phenylmethyl)piperidin-4-yl]-1-propanone dihydrochloride (compound of Example 4) | 1 g |
| (2) Lactose | 197 g |
| (3) Corn starch | 50 g |
| (4) Magnesium stearate | 2 g |

1 g of compound (1), 197 g of lactose (2) and 20 g of corn starch (3) were uniformly mixed and granulated with a paste prepared from 15 g of corn starch and 25 ml of water. After 15 g of corn starch and 2 g of magnesium stearate (4) were added, the granules were tableted, using a compressive tableting machine, to yield 2000 tablets containing 0.5 mg of compound (1) per tablet and having a diameter of 3 mm.

FORMULATION EXAMPLE 2

| | |
|---|---|
| (1) 1-(1,2,2a,3,4,5-hexahydrobenz[cd]indol-6-yl)-3-[1-(phenylmethyl)piperidin-4-yl]-1-propanone dihydrochloride (compound of Example 4) | 2 g |
| (2) Lactose | 197 g |
| (3) Corn starch | 50 g |
| (4) Magnesium stearate | 2 g |

2 g of compound (1), 197 g of lactose (2) and 20 g of corn starch (3) were uniformly mixed and granulated with a paste prepared from 15 g of corn starch and 25 ml of water. After 15 g of corn starch and 2 g of magnesium stearate (4) were added, the granules were tableted, using a compressive tableting machine, to yield 2000 tablets containing 1.0 mg of compound (1) per tablet and having a diameter of 3 mm.

EXPERIMENTAL EXAMPLE 1

The cholinesterase inhibitory activity of the compound of the present invention was tested, using (acetyl-[$^3$H])-acetylcholine. Using the $S_1$ fraction of a male Wistar rat cerebral cortex homogenate as a source of cholinesterase, (acetyl-[$^3$H])-acetylcholine, as a substrate, and the test compound, as a sample, were incubated for 30 minutes. After the reaction was terminated, a toluene scintillator was added and the reaction mixture was shaken to migrate the [$^3$H]-acetic acid resulting from the reaction to the toluene layer, where radioactivity was counted using a liquid scintillation counter to determine the cholinesterase inhibitory activity.

The sample's cholinesterase inhibitory activity was expressed by 50% inhibitory concentration ($IC_{50}$). The cholinesterase inhibitory activity of physostigmine was determined by the same method.

The results are given in Table 76.

TABLE 76

| Compound (Example No.) | Acetylcholinesterase Inhibitory Activity $IC_{50}$ (μM) |
|---|---|
| 4 | 0.0918 |
| 16-1 | 0.154 |
| 17-1 | 0.0030 |
| 17-2 | 0.0076 |
| 17-3 | 0.0172 |
| 17-4 | 0.0095 |
| 17-5 | 0.0454 |
| 17-6 | 0.0151 |
| 17-7 | 0.0330 |
| 17-8 | 0.0470 |
| 17-9 | 0.0240 |
| 17-10 | 0.0968 |
| 20-1 | 0.182 |
| 23 | 0.0614 |
| 30-1 | 0.0287 |

TABLE 76-continued

| Compound (Example No.) | Acetylcholinesterase Inhibitory Activity IC$_{50}$ (μM) |
| --- | --- |
| 30-3 | 0.0109 |
| 30-4 | 0.0430 |
| 30-10 | 0.0189 |
| 30-11 | 0.0169 |
| 30-12 | 0.0239 |
| 30-13 | 0.1297 |
| 30-16 | 0.0058 |
| 30-18 | 0.0249 |
| 30-19 | 0.0119 |
| 30-21 | 0.0036 |
| 30-22 | 0.0062 |
| 30-24 | 0.0015 |
| 30-25 | 0.000098 |
| 30-26 | 0.0044 |
| 30-27 | 0.188 |
| 30-29 | 0.0293 |
| 30-32 | 0.0911 |
| 30-34 | 0.0005 |
| 30-35 | 0.0679 |
| 30-38 | 0.00018 |
| 30-39 | 0.00050 |
| 30-40 | 0.000092 |
| 30-41 | 0.00047 |
| 30-42 | 0.00054 |
| 30-43 | 0.000065 |
| 30-44 | 0.0599 |
| 30-45 | 0.000304 |
| 30-46 | 0.000200 |
| 30-47 | 0.0195 |
| 30-48 | 0.0171 |
| 30-52 | 0.00036 |
| 30-53 | 0.0254 |
| 30-54 | 0.0609 |
| 30-56 | 0.0183 |
| 30-58 | 0.00012 |
| 30-59 | 0.00112 |
| 30-60 | 0.000078 |
| 30-61 | 0.0156 |
| 31-4 | 0.188 |
| 32-1 | 0.0024 |
| 32-2 | 0.115 |
| 32-3 | 0.0590 |
| 34-1 | 0.0393 |
| 34-2 | 0.0200 |
| 34-3 | 0.171 |
| 34-5 | 0.0316 |
| 37-2 | 0.184 |
| 37-4 | 0.136 |
| 37-5 | 0.081 |
| Physostigmine | 0.220 |

From Table 76, it is seen that the compound of the present invention is more potent than physostigmine in acetylcholinesterase inhibition.

EXPERIMENTAL EXAMPLE 2

Effects of the compound of this invention on monoamine uptake were investigated using [$^3$H]-norepinephirine(NE) and [$^3$H]-serotonin (5-HT). Rats were sacrificed by decapitation. The cerebral cortex and hippocampus were removed and homogenized in 10–15 volumes (W/V) of an ice-cold medium containing 0.32M sucrose. Crude synaptosomal preparations (P2) were isolated after differential centrifugation at 1000×g for 10 min and 20,000×g for 30 min at 4° C. Synaptosomal membranes were suspended in Krebs-Ringer bicarbonate (KRB) solution (116 mM NaCl, 4.8 mM KCl, 1.3 mM CaCl$_2$, 1.2 mM MgSO$_4$, 1.2 mM NaH$_2$PO$_4$, 25 mM NaHCO$_3$, 0.1 mM EDTA-2Na, 11.1 mM D-glucose, 0.11 mM L-ascorbic acid, 0.01 mM pargyline). Synaptosomal membrane suspension (900 μl) was preincubated with the test compound dissolved in DMSO solution at 37° C. for 5 min. The reaction was initiated by addition of 100 μl of [$^3$H]-NE (11 nM in final concentration) or [$^3$H]-HT (10 nM in final concentration). Five minutes later, the reaction was stopped by the addition of 4 ml of ice-cold KRB and the reaction mixture was filtered through Whatman CF/B. Filters were washed twice with 4 ml of KRB and the radioactivity bound was counted with liquid scintillant. Imipramine was used as positive control. All compounds were tested at $10^{-8}$, $10^{-7}$, $10^{-6}$ and $10^{-5}$M. The results are shown in Table 77.

TABLE 77

| Compound (Example No.) | Monoamine Reuptake Inhibitory Activity IC$_{50}$ (μM) | |
| --- | --- | --- |
| | NE | 5-HT |
| 2 | 0.420 | 0.594 |
| 4 | 0.347 | 0.601 |
| 19-1 | 0.328 | 1.67 |
| 23 | 2.43 | 0.0668 |
| 30-1 | 4.6 | 0.0956 |
| 30-6 | 5.96 | 0.0863 |
| 30-8 | 0.643 | 0.0607 |
| 30-19 | 2.82 | 0.066 |
| 30-21 | 1.54 | 0.0882 |
| 30-22 | 0.795 | 0.0601 |
| 30-25 | 1.31 | 0.0117 |
| 30-27 | 0.559 | 0.0798 |
| 30-28 | 2.81 | 0.0615 |
| 30-36 | 7.48 | 0.0468 |
| 31-1 | 6.183 | 0.0463 |
| 31-2 | 0.0738 | 0.00879 |
| 31-4 | 0.16 | 0.0207 |
| 31-11 | 0.515 | 0.0695 |
| 34-4 | 0.456 | 0.969 |
| 34-6 | 0.481 | 0.0806 |
| 34-8 | 0.197 | 0.363 |
| Imipramine | 1.12 | 0.063 |

From Table 77, it is seen that the compounds of the present invention are as potent as imipramine in monoamine reuptake inhibition.

What is claimed is:

1. A compound of the formula:

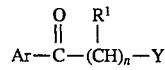

wherein

Ar is 5, 6-dihydro-2(1H)-oxo-4H-pyrrolo[3,2,1-ij]quinolin-8-yl or 4-oxo-1,2,5,6-tetrahydro-4H-pyrrolo[3,2,1-ij]quinolin-8-yl;

n is an integer from 2 to 10;

R$^1$ is a hydrogen atom;

Y is a 4-piperidinyl or 1-piperazinyl group which may be substituted by 1 to 5 substituents selected from the group consisting of (a) a straight chain or branched C$_{1-11}$ alkyl, C$_{2-6}$ alkenyl, C$_{2-6}$ alkynyl group, C$_{3-7}$ monocyclic cycloalkyl or C$_{8-14}$ bridge ring saturated hydrocarbon group which may be substituted by 1 to 5 substituents selected from the group consisting of halogen, nitro, cyane, hydroxy, C$_{1-4}$ alkoxy, C$_{1-4}$ alkylthio, amino, mono- or di-C$_{1-4}$ alkylamino, 5 to 7-membered cyclic amino, C$_{1-4}$ alkyl-carbonylamino, C$_{1-4}$ alkylsulfonylamino, C$_{1-4}$ alkoxy-carbonyl, carboxyl, C$_{1-6}$ alkyl-carbonyl, carbamoyl, mono- or di-C$_{1-4}$ alkylcarbamoyl and C$_{1-6}$ alkylsulfonyl, (b) a C$_{6-14}$ aryl, C$_{7-18}$ aralkyl, C$_{6-14}$ aryl-C$_{2-12}$ alkenyl, C$_{6-14}$ aryl-C$_{2-12}$ alkynyl or C$_{3-7}$ cycloalkyl-C$_{1-6}$ alkyl group which may be substituted by 1 to 5 substituents selected from the group consisting of $C_{1-4}$ alkyl, halogen, nitro, cyano, hydroxy, $C_{1-4}$ alkoxy, $C_{1-4}$ alkylthio, amino, mono- or di-$C_{1-4}$ alkylamino, 5 to 7-membered cyclic amino, $C_{1-4}$ alkyl-carbonylamino, aminocarbonyloxy, mono- or di-$C_{1-4}$ alkylamino-carbonyloxy, $C_{1-4}$ alkylsulfonylamino, $C_{1-4}$ alkoxy-carbonyl, carboxyl, $C_{1-6}$ alkyl-carbonyl, $C_{3-7}$ cycloalkyl-carbonyl, carbamoyl, mono- or di-$C_{1-4}$ alkyl-carbamoyl, $C_{1-6}$ alkylsulfonyl, $C_{3-7}$ cycloalkylsulfonyl and a phenyl, naphthyl, mono- or di-phenyl-$C_{1-3}$ alkyl, phenoxy, benzoyl, phenoxycarbonyl, benzylcarbonyl, phenyl-$C_{1-4}$ alkylcarbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfonyl, phenyl-$C_{1-4}$ alkylsulfonylamino or phenylsulfonylamino group which may be substituted by 1 to 5 substituents selected from the group consisting of $C_{1-4}$ alkyl, $C_{1-4}$ alkoxy, halogen, hydroxy, benzoyloxy, amino, mono- or di-$C_{1-4}$ alkylamino, nitro, $C_{1-6}$ alkyl-carbonyl and benzoyl, (c) an acyl group which may be substituted by 1 to 3 substituents selected from the group consisting of halogen, nitro, hydroxy, amino, mono- or di-$C_{1-6}$ alkylamino and $C_{1-4}$ alkoxy, (d) halogen atom, (e) nitro group, (f) cyano group, (g) oxo group, (h) hydroxyl group, (i) $C_{1-4}$ alkoxy group, j) $C_{1-4}$ alkylthio group, (k) amino group, (l) mono or di-$C_{1-4}$ alkylamino group, (m) 5 to 7-membered cyclic amino, (n) $C_{1-4}$ alkyl-carbonylamino group, (o) $C_{1-4}$ alkylsulfonylamino group, (p) $C_{1-4}$ alkoxy-carbonyl group, (q) phenyl-$C_{1-4}$ alkoxycarbonyl group, (r) carboxyl group, (s) $C_{1-6}$ alkyl-carbonyl group, (t) benzoyl group which may be substituted by 1 to 3 substituents selected from the group consisting of $C_{1-4}$ alkyl, halogen, $C_{1-4}$ alkoxy, mono- or di-$C_{1-4}$ alkylamino, 5 to 7-membered cyclic amino group, nitro and hydroxy, (u) carbamoyl (v) mono or di-$C_{1-4}$ alkyl-carbamoyl group and (w) $C_{1-6}$ alkylsulfonyl group or a pharmaceutically acceptable salt thereof.

2. A compound as claimed in claim 1, wherein n is an integer from 2 to 6.

3. A compound as claimed in claim 1 selected from

8-[3-[(3 -methylphenyl)methyl]-1-piperazinyl]-1-oxopropyl]-1,2,5,6-tetrahydro-4 H-pyrrolo[3,2,1-ij]quinolin-4-one or a pharmaceutically acceptable salt thereof, 8-[3-[4-[(3-chlorophenyl)methyl]-1-piperazinyl]-1-oxopropyl]-1,2,5,6 -tetrahydro-4H-pyrrolo[3,2,1-ij]quinolin-4-one or a pharmaceutically acceptable salt thereof, 8-[3-[4-[(2-methylphenyl)methyl]-1-piperazinyl]-1-oxopropyl]-5,6-dihydro-4 H-pyrrolo[3,2,1-ij]quinolin-2(1H)-one or a pharmaceutically acceptable salt thereof, 8-[3-[4-[(3-chlorophenyl)methyl]-1-piperazinyl]-1-oxopropyl]-5,6-dihydro-4 H-pyrrolo[3,2,1-ij]quinolin-2(1H)-one or a pharmaceutically acceptable salt thereof, 8-[3-[1-(phenylmethyl)-4-piperidinyl]-1-oxopropyl]-1,2,5,6-tetrahydro-4 H-pyrrolo[3,2,1-ij]quinolin-4-one or a pharmaceutically acceptable salt thereof, 8-[3-[1-[(4-methylphenyl)methyl]-4-piperidinyl]-1-oxopropyl]-1,2,5,6 -tetrahydro-4H-pyrrolo[3,2,1-ij]quinolin-4-one or a pharmaceutically acceptable salt thereof, 8-[3-[1-[(3-methoxyphenyl)methyl]-4-piperidinyl]-1-oxopropyl]-1,2,5,6 -tetrahydro-4H-pyrrolo[3,2,1-ij]quinolin-4-one or pharmaceutically acceptable thereof, 8-[3-[1-[(2,4-dimethylphenyl)methyl]-4-piperidinyl]-1-oxopropyl]-1,2,5,6 -tetrahydro-4H-pyrrolo[3,2,1-ij]quinolin-4-one or a pharmaceutically acceptable salt thereof, 8-[3-[1-[(2,5-dimethylphenyl)methyl]-4-piperidinyl]-1-oxopropyl]-1,2,5,6 -tetrahydro-4H-pyrrolo[3,2,1-ij]quinolin-4-one or a pharmaceutically acceptable salt thereof, 8-[3-[1-[(4-chlorophenyl)methyl]-4-piperidinyl]-1-oxopropyl]-1,2,5,6 -tetrahydro-4H-pyrrolo[3,2,1-ij]quinolin-4-one or pharmaceutically acceptable salt thereof, 8-[3-[1-(4-nitrophenyl)methyl]-4-piperidinyl]-1-oxopropyl]-1,2,5,6 -tetrahydro-4H-pyrrolo[3,2,1-ij]quinolin-4-one or a pharmaceutically acceptable salt thereof, 8-[3-[1-(phenylmethyl)methyl]-4-piperidinyl[-1-oxopropyl]-5,6-dihydro-4 H-pyrrolo[3,2,1-ij]quinolin-2(1H)-one or a pharmaceutically acceptable salt thereof, 8-[3-[1-[(3,methoxyphenyl)methyl]-4-piperidinyl]-1-oxopropyl]-5,6-dihydro-4 H-pyrrolo[3,2,1-ij]quinolin-2(1H)-one or a pharmaceutically acceptable salt thereof, 8-[3-[4-(phenylmethyl)-1-piperidinyl[-1-oxopropyl]-1,2,5, 6-tetrahydro-4 H-pyrrolo[3,2,1-ij]quinolin-4-one or a pharmaceutically acceptable salt thereof.

4. A cholinesterase inhibitory composition which contains an effective cholinesterase inhibiting amount of a compound of the formula (I) as claimed in claim 1 or a pharmaceutically acceptable salt thereof and a pharmacologically acceptable carrier.

5. A pharmaceutical composition as claimed in claim 4, in which the disease is senile dementia and/or Alzheimer's disease.

6. A method of treating senile dementia caused by increased cholinesterase activity which comprises administering an effective amount of the compound of the formula:

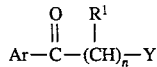

as claimed in claim 1, or a pharmaceutically acceptable salt thereof.

* * * * *